(12) United States Patent
Cowan et al.

(10) Patent No.: US 10,835,674 B2
(45) Date of Patent: Nov. 17, 2020

(54) NESTED SYRINGE ASSEMBLY

(71) Applicant: BAYER HEALTHCARE LLC, Whippany, NJ (US)

(72) Inventors: Kevin Cowan, Allison Park, PA (US); Damian Peter Francis Savio, Lane Cove (AU); Eric Siu, Strathfield (AU); Richard Sokolov, Earlwood (AU); Peter John Sprada, Croydon (AU)

(73) Assignee: BAYER HEALTHCARE LLC, Whippany, NJ (US)

( * ) Notice: Subject to any disclaimer, the term of this patent is extended or adjusted under 35 U.S.C. 154(b) by 144 days.

(21) Appl. No.: 15/774,037

(22) PCT Filed: Nov. 11, 2016

(86) PCT No.: PCT/US2016/061495
§ 371 (c)(1),
(2) Date: May 7, 2018

(87) PCT Pub. No.: WO2017/083622
PCT Pub. Date: May 18, 2017

(65) Prior Publication Data
US 2018/0318507 A1    Nov. 8, 2018

Related U.S. Application Data

(60) Provisional application No. 62/254,905, filed on Nov. 13, 2015.

(51) Int. Cl.
*A61M 5/19*    (2006.01)
*A61M 5/00*    (2006.01)
(Continued)

(52) U.S. Cl.
CPC .............. *A61M 5/19* (2013.01); *A61M 5/002* (2013.01); *A61M 5/007* (2013.01);
(Continued)

(58) Field of Classification Search
CPC .............. A61M 5/14546; A61M 5/007; A61M 5/14566; A61M 5/002; A61M 2209/06;
(Continued)

(56) References Cited

U.S. PATENT DOCUMENTS

| 1,711,594 A | * | 5/1929 | Gillespie | ............... | A61M 5/002 |
| | | | | | 206/365 |
| 1,988,480 A | | 1/1935 | Campkin | | |

(Continued)

FOREIGN PATENT DOCUMENTS

| CN | 205494564 U | 8/2016 |
| DE | 1292787 B | 4/1969 |

(Continued)

OTHER PUBLICATIONS

Translation of JP 10-174717 (Year: 1998).*

(Continued)

*Primary Examiner* — Emily L Schmidt
(74) *Attorney, Agent, or Firm* — Joseph L. Kent; David Schramm; James R. Stevenson

(57) ABSTRACT

Provided is an apparatus, system, and method for a nested syringe assembly. The nested syringe assembly (100) includes a first syringe (104) having a cylindrical body defining an inner diameter and a second syringe (102) having a cylindrical body defining an outer diameter. The outer diameter of the second syringe is less than the inner diameter of the first syringe. At least a portion of the cylindrical body of the second syringe is disposed within the cylindrical body of the first syringe.

18 Claims, 35 Drawing Sheets

(51) Int. Cl.
*A61M 5/145* (2006.01)
*A61M 5/31* (2006.01)
*A61M 5/315* (2006.01)
*A61M 5/32* (2006.01)
*A61M 5/50* (2006.01)
A61M 5/24 (2006.01)
A61M 5/38 (2006.01)
A61M 5/178 (2006.01)

(52) U.S. Cl.
CPC ...... *A61M 5/14546* (2013.01); *A61M 5/3146* (2013.01); *A61M 5/31513* (2013.01); *A61M 5/3202* (2013.01); *A61M 5/5086* (2013.01); A61M 5/2466 (2013.01); A61M 5/38 (2013.01); A61M 2005/1787 (2013.01); A61M 2005/3101 (2013.01); A61M 2005/31518 (2013.01); A61M 2005/31598 (2013.01); A61M 2205/0222 (2013.01); A61M 2207/00 (2013.01); A61M 2209/06 (2013.01)

(58) Field of Classification Search
CPC .............. A61M 5/284; A61M 5/31596; A61M 5/3294; A61M 2005/31598; A61M 5/2066; A61M 5/2448; A61M 2005/14553; A61M 2005/14573; A61M 5/1458; A61M 5/16827; A61J 1/00
See application file for complete search history.

(56) References Cited

U.S. PATENT DOCUMENTS

| | | |
|---|---|---|
| 2,627,720 A | 2/1953 | Williams et al. |
| 2,734,504 A | 2/1956 | Crescas et al. |
| 2,869,543 A * | 1/1959 | Ratcliff ............... A61M 5/19 604/90 |
| 2,946,331 A | 7/1960 | Jungst et al. |
| 2,956,563 A | 10/1960 | Sarnoff |
| 3,115,135 A | 12/1963 | Sarnoff |
| 3,348,545 A | 10/1967 | Sarnoff et al. |
| 3,395,704 A | 8/1968 | Frey et al. |
| 3,557,787 A | 1/1971 | Cohen |
| 3,631,847 A | 1/1972 | Hobbs |
| 3,701,345 A | 10/1972 | Heilman |
| 3,752,145 A | 8/1973 | Runnells et al. |
| 3,812,843 A | 5/1974 | Wootten et al. |
| 3,880,138 A | 4/1975 | Wootten et al. |
| 3,911,927 A * | 10/1975 | Rich ............... A61M 25/0119 604/271 |
| 4,006,736 A | 2/1977 | Kranys et al. |
| 4,150,672 A | 4/1979 | Martin et al. |
| 4,267,836 A | 5/1981 | Whitney et al. |
| 4,269,185 A | 5/1981 | Whitney et al. |
| 4,273,122 A | 6/1981 | Whitney et al. |
| 4,342,312 A | 8/1982 | Whitney et al. |
| 4,345,595 A | 8/1982 | Whitney et al. |
| 4,351,335 A | 9/1982 | Whitney et al. |
| 4,405,318 A | 9/1983 | Whitney et al. |
| 4,424,720 A | 1/1984 | Bucchianeri |
| 4,465,473 A | 8/1984 | Ruegg |
| 4,573,978 A | 3/1986 | Reilly |
| 4,581,016 A * | 4/1986 | Gettig ............... A61M 5/31596 604/88 |
| 4,634,431 A | 1/1987 | Whitney et al. |
| 4,636,198 A | 1/1987 | Stade |
| 4,677,980 A | 7/1987 | Reilly et al. |
| 4,695,271 A | 9/1987 | Goethel |
| 4,744,786 A | 5/1988 | Hooven |
| 4,854,324 A | 8/1989 | Hirschman et al. |
| 4,869,720 A | 9/1989 | Chernack |
| 4,936,833 A | 6/1990 | Sams |
| 4,966,601 A | 10/1990 | Draenert |
| 5,002,538 A | 3/1991 | Johnson |
| 5,007,904 A | 4/1991 | Densmore et al. |
| 5,098,386 A | 3/1992 | Smith |
| 5,178,609 A | 1/1993 | Ishikawa |
| 5,209,731 A | 5/1993 | Sterman et al. |
| 5,219,099 A | 6/1993 | Spence et al. |
| 5,269,762 A | 12/1993 | Armbruster et al. |
| 5,279,569 A | 1/1994 | Neer et al. |
| 5,300,031 A | 4/1994 | Neer et al. |
| 5,383,858 A | 1/1995 | Reilly et al. |
| 5,451,221 A | 9/1995 | Cho et al. |
| 5,456,669 A | 10/1995 | Neer et al. |
| 5,520,653 A | 5/1996 | Reilly et al. |
| 5,535,746 A | 7/1996 | Hoover et al. |
| 5,779,675 A | 7/1998 | Reilly et al. |
| 5,782,815 A | 7/1998 | Yanai et al. |
| 5,792,102 A | 8/1998 | Mueller-Spaeth |
| 5,858,000 A * | 1/1999 | Novacek ............... A61L 2/28 604/110 |
| 5,873,861 A | 2/1999 | Hitchins et al. |
| 5,944,694 A | 8/1999 | Hitchins et al. |
| 5,947,929 A | 9/1999 | Trull |
| 5,947,935 A | 9/1999 | Rhinehart et al. |
| 6,315,758 B1 | 11/2001 | Neer et al. |
| 6,336,913 B1 | 1/2002 | Spohn et al. |
| 6,368,307 B1 | 4/2002 | Ziemba et al. |
| 6,432,089 B1 | 8/2002 | Kakimi et al. |
| 6,520,930 B2 | 2/2003 | Critchlow et al. |
| 6,652,489 B2 | 11/2003 | Trocki et al. |
| 6,659,979 B2 | 12/2003 | Neer et al. |
| 6,716,195 B2 | 4/2004 | Nolan et al. |
| 6,733,477 B2 | 5/2004 | Cowan et al. |
| 6,743,202 B2 | 6/2004 | Hirschman et al. |
| 6,958,053 B1 | 10/2005 | Reilly |
| 7,273,477 B2 | 9/2007 | Spohn et al. |
| 7,361,156 B2 | 4/2008 | Joyce et al. |
| 7,393,341 B2 | 7/2008 | Nemoto |
| 7,419,478 B1 | 9/2008 | Reilly et al. |
| 7,462,166 B2 | 12/2008 | Kowan et al. |
| 7,497,843 B1 | 3/2009 | Castillo et al. |
| 7,553,294 B2 | 6/2009 | Lazzaro et al. |
| 7,563,249 B2 | 7/2009 | Schriver et al. |
| 7,666,169 B2 | 2/2010 | Cowan et al. |
| 7,674,244 B2 | 3/2010 | Kalafut et al. |
| 7,682,345 B2 | 3/2010 | Savage |
| 7,691,085 B2 | 4/2010 | Dedig et al. |
| 7,846,136 B2 | 12/2010 | Witowski |
| 8,012,125 B1 | 9/2011 | Fago et al. |
| 8,038,651 B2 | 10/2011 | Keller |
| 8,133,203 B2 | 3/2012 | Hack |
| 8,439,876 B2 | 5/2013 | Spohn et al. |
| 8,572,834 B2 | 11/2013 | Cude |
| 8,632,506 B2 | 1/2014 | Steenfeldt-Jensen et al. |
| 8,721,596 B2 | 5/2014 | Trocki et al. |
| 9,173,995 B1 | 11/2015 | Tucker et al. |
| 9,474,857 B2 | 10/2016 | Riley et al. |
| 2001/0047153 A1 | 11/2001 | Trocki et al. |
| 2002/0128607 A1 | 9/2002 | Haury et al. |
| 2004/0035743 A1 | 2/2004 | Tighe et al. |
| 2004/0064041 A1 | 4/2004 | Lazzaro et al. |
| 2007/0219508 A1* | 9/2007 | Bisegna ............ A61M 5/31513 604/218 |
| 2009/0112087 A1 | 4/2009 | Fago |
| 2009/0143746 A1* | 6/2009 | Mudd ................... A61M 5/347 604/243 |
| 2011/0106015 A1 | 5/2011 | Liscio et al. |
| 2011/0208123 A1 | 8/2011 | Gray et al. |
| 2011/0224642 A1* | 9/2011 | Fojtik ................... A61M 5/204 604/500 |
| 2011/0272310 A1* | 11/2011 | Tennican ............... A61J 1/2096 206/364 |
| 2012/0016234 A1 | 1/2012 | Nemoto et al. |
| 2012/0265143 A1 | 10/2012 | Krumme et al. |
| 2013/0110046 A1* | 5/2013 | Nowak ................. A61M 5/002 604/152 |
| 2013/0274655 A1 | 10/2013 | Jennings et al. |
| 2013/0281940 A1 | 10/2013 | Gelblum et al. |
| 2013/0340608 A1 | 12/2013 | Yamamoto |
| 2014/0228802 A1 | 8/2014 | Mackey et al. |

(56) References Cited

U.S. PATENT DOCUMENTS

2015/0080841 A1\* 3/2015 Bradley ............... A61M 5/19
604/500

FOREIGN PATENT DOCUMENTS

| | | |
|---|---|---|
| DE | 69507018 T2 | 8/1999 |
| DE | 69416686 T2 | 10/1999 |
| DE | 69527281 T2 | 1/2003 |
| DE | 202004005433 U1 | 7/2004 |
| DE | 102004032970 A1 | 2/2006 |
| EP | 0143895 A1 | 6/1985 |
| EP | 0346950 A2 | 12/1989 |
| EP | 0362484 A2 | 4/1990 |
| EP | 0482677 B1 | 4/1998 |
| EP | 0893133 B1 | 11/2002 |
| EP | 1416994 A1 | 5/2004 |
| EP | 1188669 B1 | 8/2004 |
| EP | 1465101 A2 | 10/2004 |
| EP | 1281408 B1 | 11/2004 |
| EP | 1484071 A1 | 12/2004 |
| EP | 1512423 A1 | 3/2005 |
| EP | 1531889 A1 | 5/2005 |
| EP | 1563859 A1 | 8/2005 |
| EP | 1588728 A1 | 10/2005 |
| EP | 1596908 A1 | 11/2005 |
| EP | 1642606 A1 | 4/2006 |
| EP | 1647291 A1 | 4/2006 |
| EP | 1681069 A1 | 7/2006 |
| EP | 1688157 A1 | 8/2006 |
| EP | 1703924 A1 | 9/2006 |
| EP | 1723977 A1 | 11/2006 |
| EP | 1732093 A1 | 12/2006 |
| EP | 1736189 A1 | 12/2006 |
| EP | 1767233 A1 | 3/2007 |
| EP | 1782853 A1 | 5/2007 |
| EP | 1820523 A1 | 8/2007 |
| EP | 1820524 A1 | 8/2007 |
| EP | 1825875 A1 | 8/2007 |
| EP | 1825876 A1 | 8/2007 |
| EP | 1825877 A1 | 8/2007 |
| EP | 1827535 A2 | 9/2007 |
| EP | 1896100 A2 | 3/2008 |
| EP | 1932556 A1 | 6/2008 |
| EP | 1888218 B1 | 12/2008 |
| EP | 1486219 B1 | 4/2009 |
| EP | 2043708 A1 | 4/2009 |
| EP | 2015800 A4 | 5/2009 |
| EP | 2055332 A1 | 5/2009 |
| EP | 1847285 B1 | 9/2009 |
| EP | 1670522 B1 | 11/2009 |
| EP | 2156857 A2 | 2/2010 |
| EP | 2187993 A1 | 5/2010 |
| EP | 2227274 A1 | 9/2010 |
| EP | 2227276 A1 | 9/2010 |
| EP | 2240219 A2 | 10/2010 |
| EP | 2244766 A1 | 11/2010 |
| EP | 2253348 A1 | 11/2010 |
| EP | 2315148 A1 | 4/2011 |
| EP | 2025356 B1 | 5/2011 |
| EP | 2318966 A2 | 5/2011 |
| EP | 2331175 A1 | 6/2011 |
| EP | 2341456 A1 | 7/2011 |
| EP | 2347359 A2 | 7/2011 |
| EP | 2353118 A1 | 8/2011 |
| EP | 2361647 A1 | 8/2011 |
| EP | 2362791 A2 | 9/2011 |
| EP | 2376146 A2 | 10/2011 |
| EP | 2384778 A1 | 11/2011 |
| EP | 2409720 A1 | 1/2012 |
| EP | 2411071 A1 | 2/2012 |
| EP | 2416821 A1 | 2/2012 |
| EP | 2427234 A1 | 3/2012 |
| EP | 2429614 A2 | 3/2012 |
| EP | 2227275 B1 | 6/2012 |
| EP | 2464402 A2 | 6/2012 |
| EP | 2337595 B1 | 7/2012 |
| EP | 2481430 A1 | 8/2012 |
| EP | 2485790 A1 | 8/2012 |
| EP | 2316509 B1 | 10/2012 |
| EP | 2363158 B1 | 11/2012 |
| EP | 2536449 A1 | 12/2012 |
| EP | 1938853 B1 | 1/2013 |
| EP | 2222358 B1 | 1/2013 |
| EP | 2275155 B1 | 4/2013 |
| EP | 2316507 B1 | 4/2013 |
| EP | 2316506 B1 | 5/2013 |
| EP | 2359883 B1 | 5/2013 |
| EP | 2229199 B1 | 6/2013 |
| EP | 2416824 B1 | 6/2013 |
| EP | 2618870 A2 | 7/2013 |
| EP | 2621553 A2 | 8/2013 |
| EP | 2628496 A1 | 8/2013 |
| EP | 2363160 B1 | 9/2013 |
| EP | 2251053 B1 | 10/2013 |
| EP | 2643035 A2 | 10/2013 |
| EP | 2654843 A1 | 10/2013 |
| EP | 2665501 A1 | 11/2013 |
| EP | 1716884 B1 | 12/2013 |
| EP | 2286855 B1 | 12/2013 |
| EP | 2520318 B1 | 12/2013 |
| EP | 2671603 A1 | 12/2013 |
| EP | 2686040 A1 | 1/2014 |
| EP | 2692375 A1 | 2/2014 |
| EP | 2185227 B1 | 3/2014 |
| EP | 2707824 A2 | 3/2014 |
| EP | 2732393 A2 | 5/2014 |
| EP | 2734253 A1 | 5/2014 |
| FR | 999475 A | 1/1952 |
| FR | 2850564 A1 | 8/2004 |
| GB | 848204 A | 9/1960 |
| GB | 1049263 A | 11/1966 |
| GB | 1576733 A | 10/1980 |
| GB | 2486690 A | 6/2012 |
| GB | 2501897 A | 11/2013 |
| JP | 10-174717 \* | 6/1998 ............ A61M 5/002 |
| JP | 2001269404 A | 10/2001 |
| JP | 2006512106 A | 4/2006 |
| JP | 2009540995 A | 11/2009 |
| JP | 2010214048 A | 9/2010 |
| JP | 4833984 B2 | 12/2011 |
| JP | 2012106029 A | 6/2012 |
| JP | 2012120934 A | 6/2012 |
| JP | 4965582 B2 | 7/2012 |
| JP | 2014004480 A | 1/2014 |
| JP | 5436897 B2 | 3/2014 |
| JP | 5518844 B2 | 6/2014 |
| WO | 0012157 A1 | 3/2000 |
| WO | 0012158 A1 | 3/2000 |
| WO | 0137903 A2 | 5/2001 |
| WO | 2004004812 A1 | 1/2004 |
| WO | 2007130061 A1 | 11/2007 |
| WO | 2008009645 A1 | 1/2008 |
| WO | 2009036496 A2 | 3/2009 |
| WO | 2009094345 A1 | 7/2009 |
| WO | 2011131783 A2 | 10/2011 |
| WO | 2012124028 A1 | 9/2012 |
| WO | 2012155035 A1 | 11/2012 |
| WO | 2017083622 A1 | 5/2017 |

OTHER PUBLICATIONS

European Search Report from EP15191888 dated Jan. 27, 2016.
European Search Report from EP15191984 dated Jan. 27, 2016.
"Extended European Search Report from EP Application No. 15853879", dated Sep. 26, 2018.
"Extended European Search Report from EP Application No. 15855844.5", dated Jun. 19, 2018.
"Extended European Search Report from EP Application No. 171919772", dated Jan. 15, 2018.
International Search Report and Written Opinion dated Mar. 10, 2016 from PCT/US2015/057747.

(56) References Cited

OTHER PUBLICATIONS

International Search Report and Written Opinion dated Jan. 27, 2016 from PCT/US2015/057706.
International Search Report and Written Opinion dated Jan. 28, 2016 from PCT/US2015/057709.
International Search Report and Written Opinion dated Mar. 4, 2016 from PCT/US2015/057751.
"International Search Report and Written Opinion from PCT Application No. PCT/US2016/061495", dated Mar. 3, 2017.
International Search Report dated Mar. 10, 2016 from PCT/US2015/057747.
International Search Report dated Jan. 20, 2016 from PCT/US2015/057709.
International Search Report dated Mar. 4, 2016 from PCT/US2015/057751.

* cited by examiner

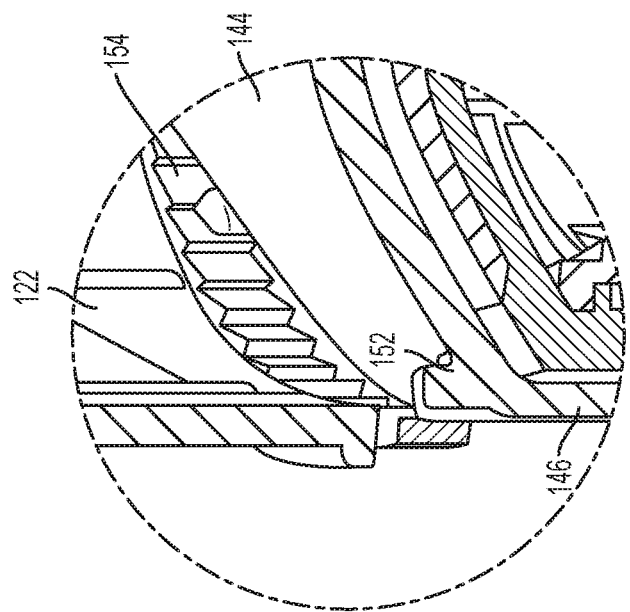
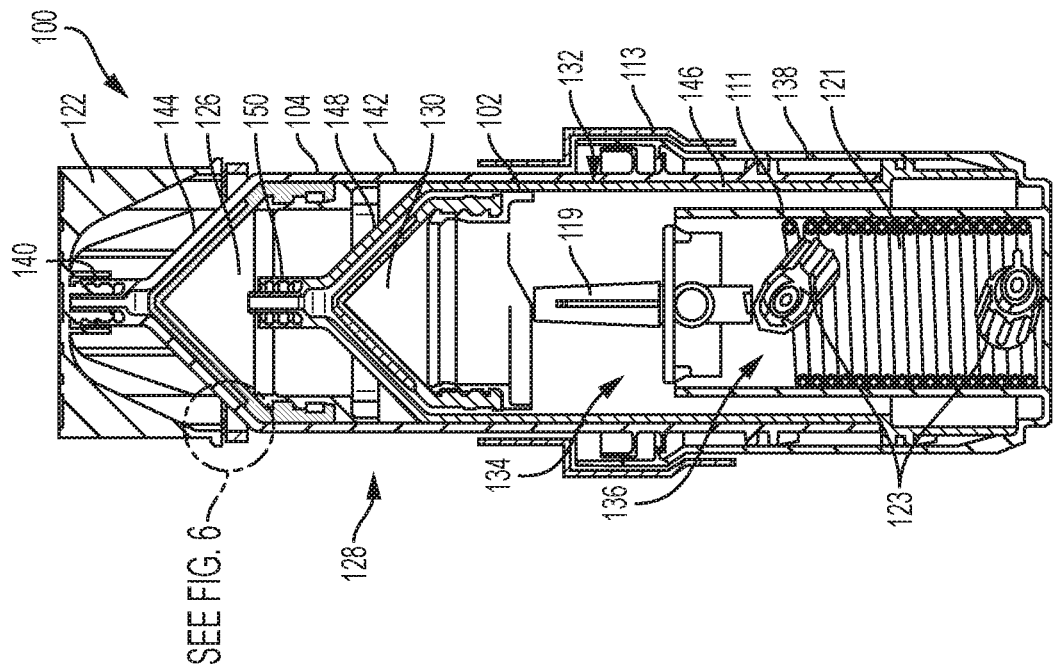

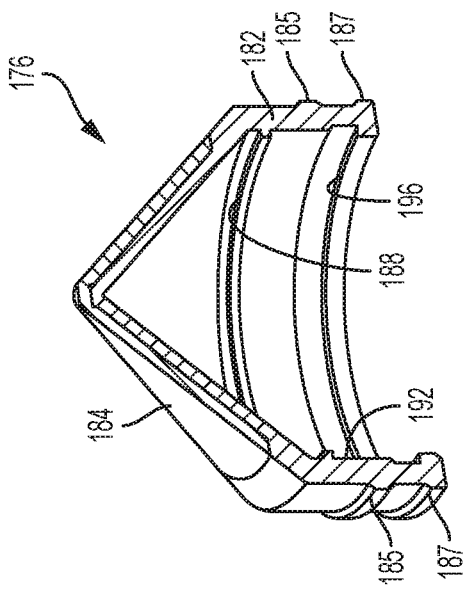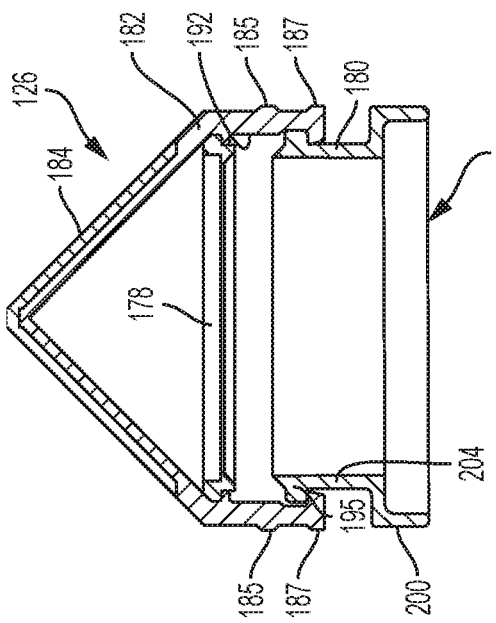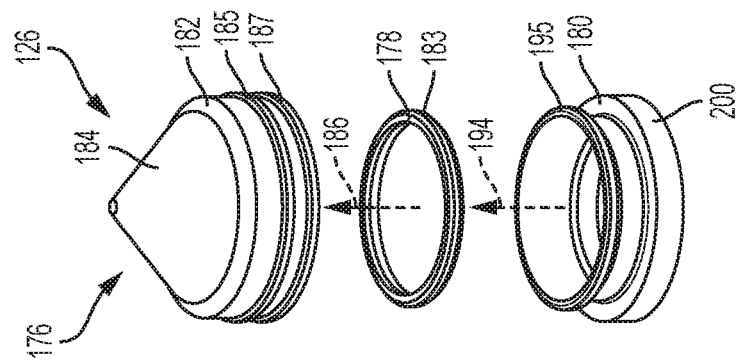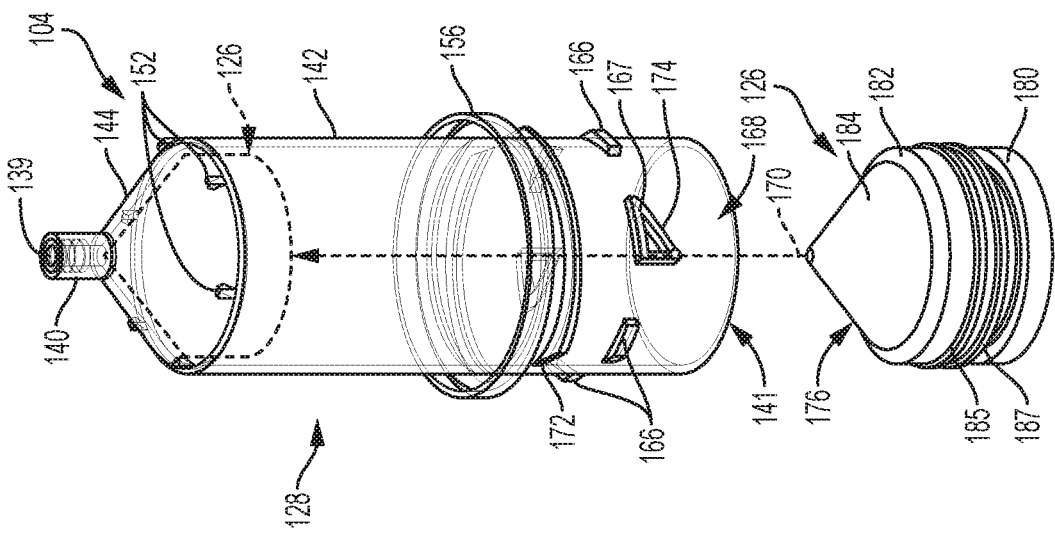

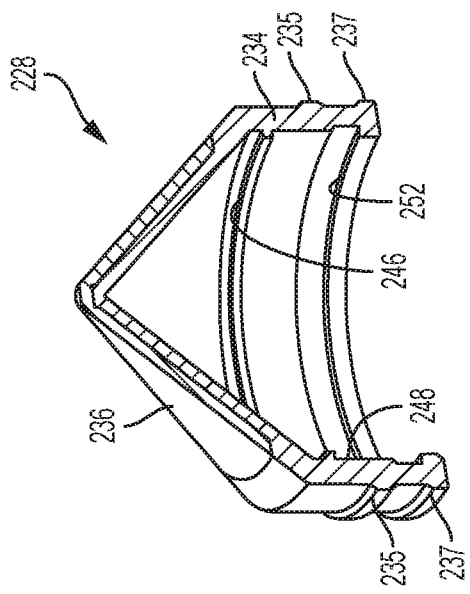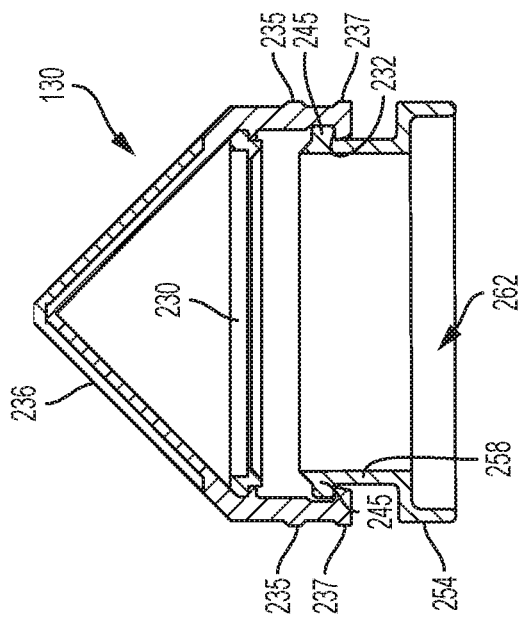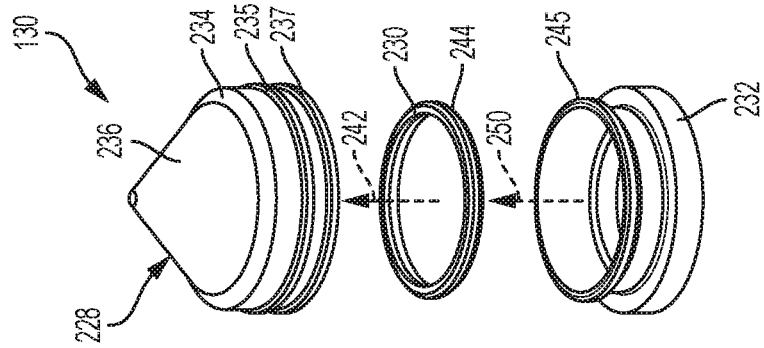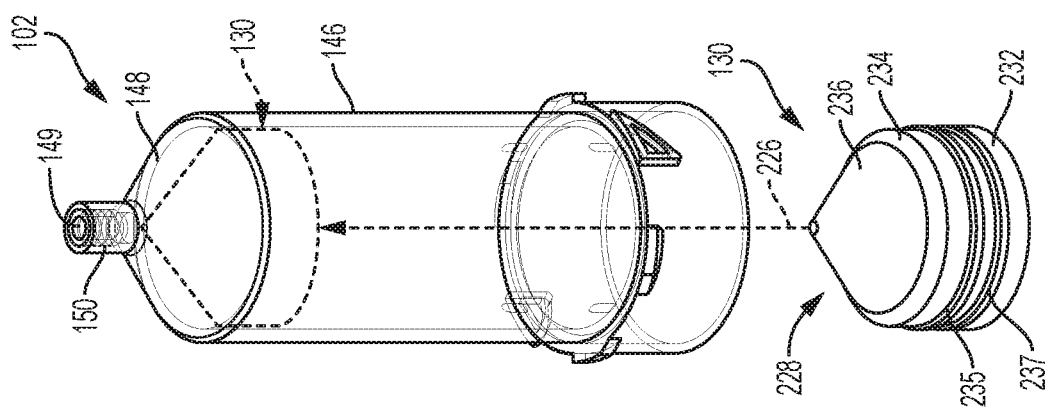

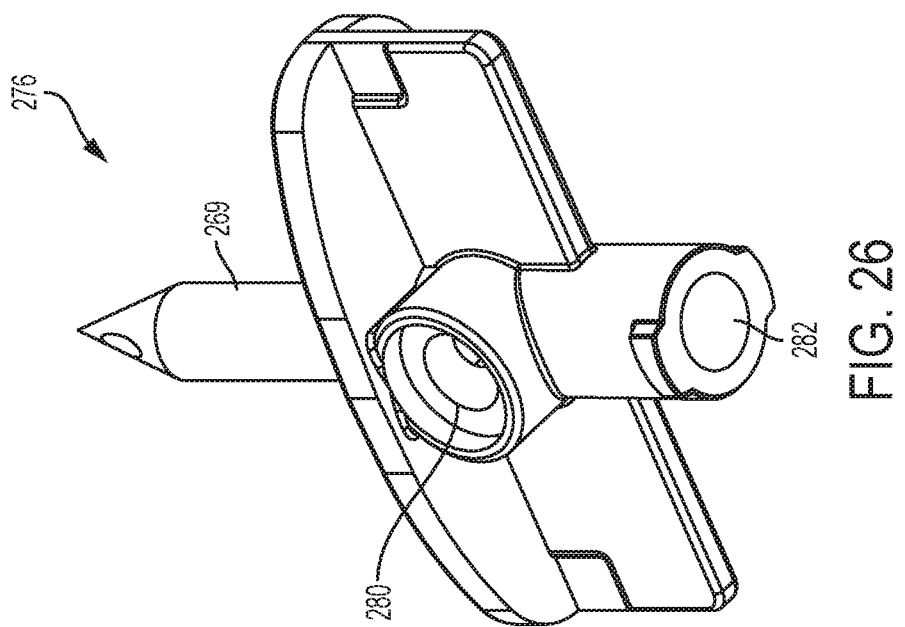
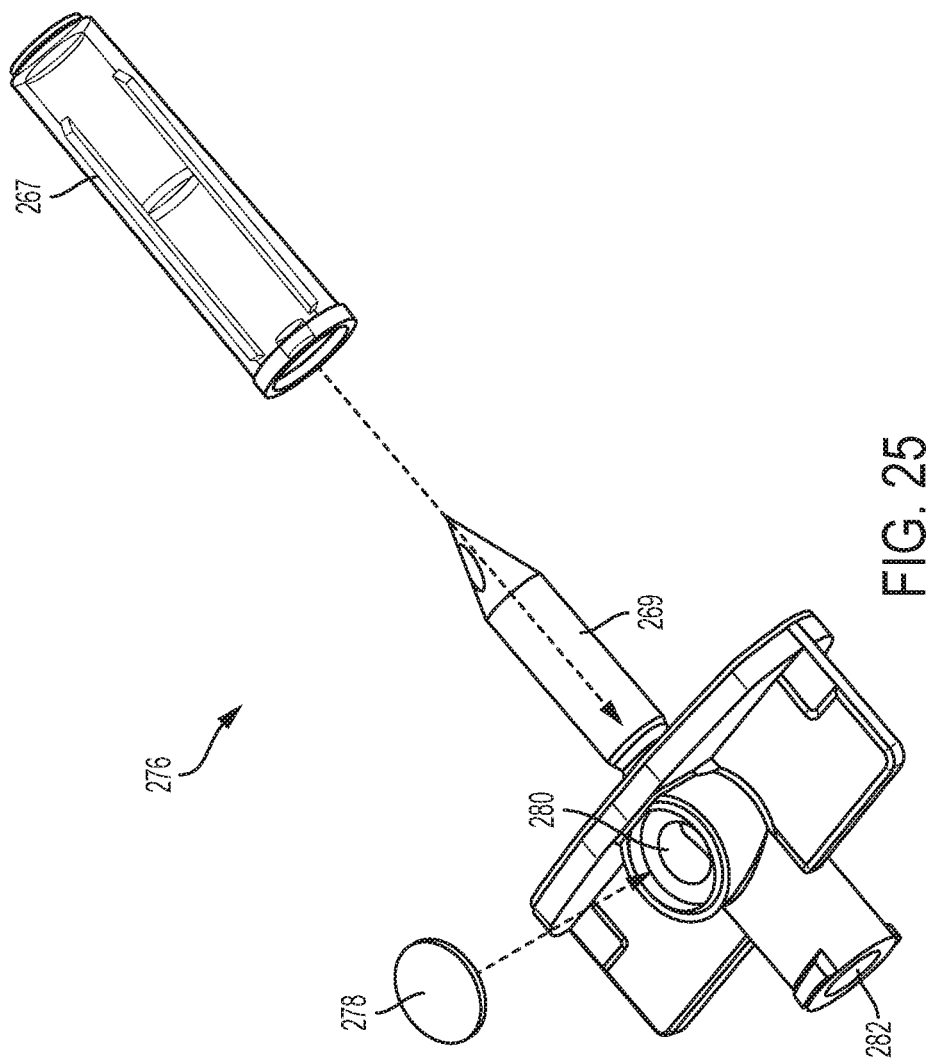

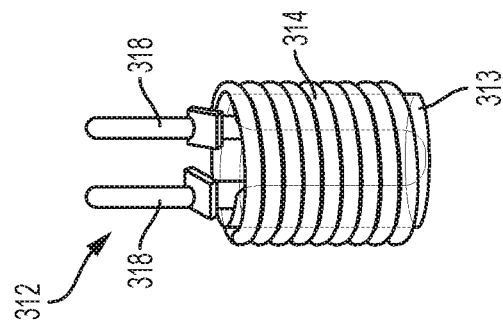
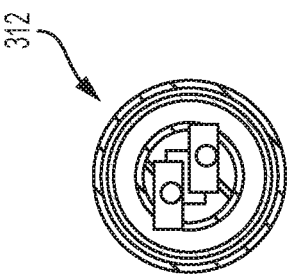
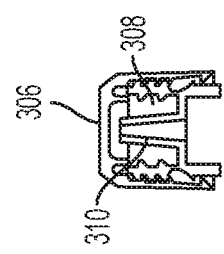
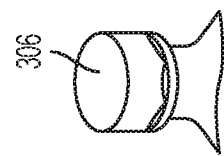
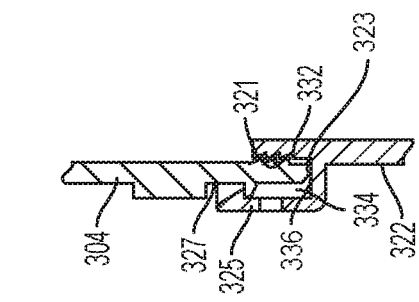
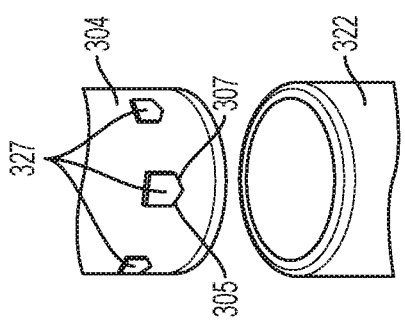
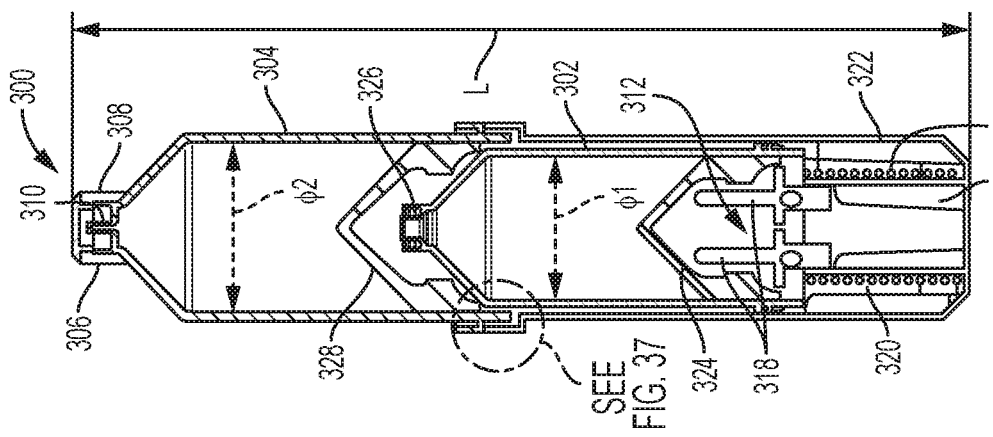

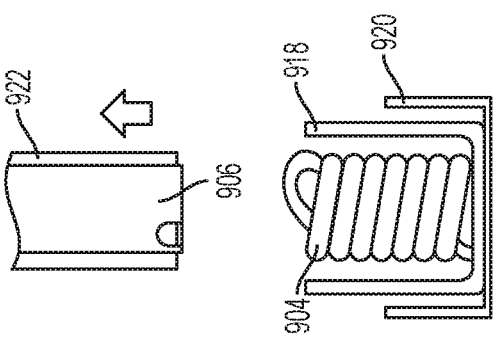
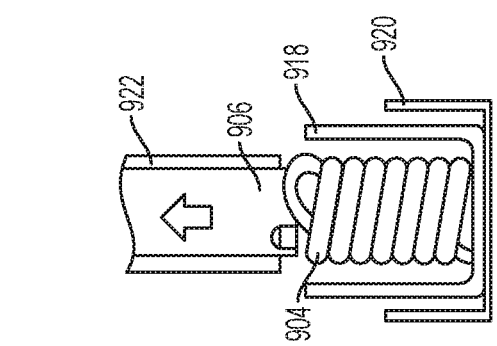
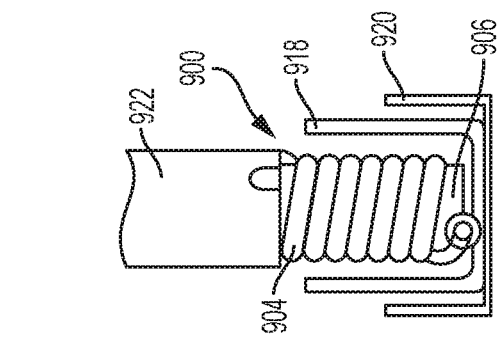
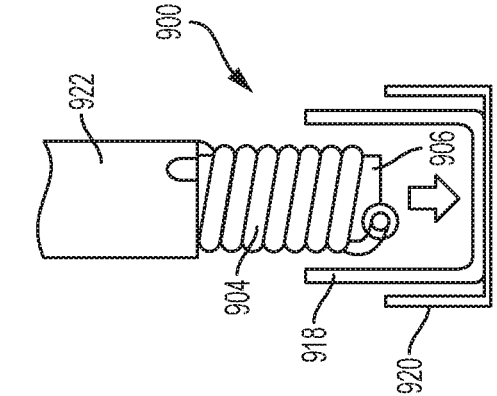
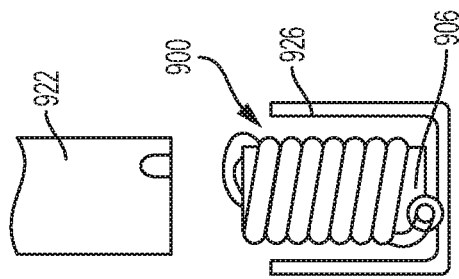
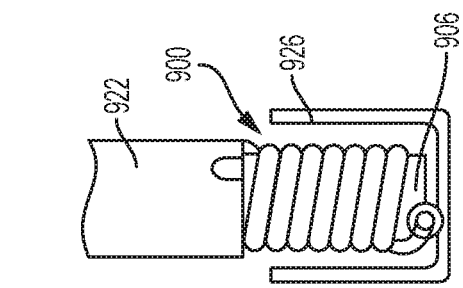
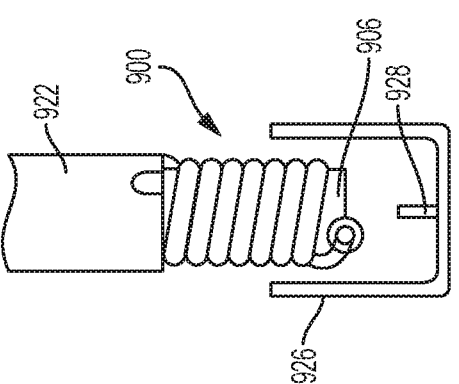

NESTED SYRINGE ASSEMBLY

CROSS REFERENCE TO RELATED APPLICATIONS

This application is a 371 national phase application of PCT International Application No. PCT/US2016/061495, filed Nov. 11, 2016, and claims the benefit under 35 USC § 119(e) of U.S. Provisional Application No. 62/254,905, filed Nov. 13, 2015, entitled "NESTED SYRINGE ASSEMBLY," the disclosures of which are herein incorporated by reference in their entirety.

BACKGROUND

The present disclosure is related generally to a packaging system for storing and shipping an injection device. More particularly, the present disclosure is directed to a packaging system for storing and shipping a single-patient single use disposable (SP-SUDs) injection device. Still more particularly, the present disclosure is related to a nested packaging system for storing and shipping a SP-SUDs including a set of syringes each of which is designed to be filled with a dose of fluid to be injected into a patient.

Single-Patient Single Use Disposables (SP-SUDs) are now commonplace in medical use once it was verified that using a sterile wear instrument once per patient was a better practice, versus cleaning and using the same instrument multiple times across several patients. A SP-SUD that has been sold and certified as sterile is provided in a sterile package. The package remains sealed prior to use. Sterile packaged SP-SUDs are becoming more commonplace as medical professionals and surgeons are looking for convenient and time saving packaging for sterilized devices.

Syringe injection systems are among the medical devices that have been packaged for SP-SUDs use. Such syringe injection systems have been in use in medical procedures for many years. Many such syringes are operated manually by advancing a plunger extension in operative connection with an internal plunger to pressurize the fluid within the syringe. In numerous medical injection procedures, however, accurate control and/or high pressures are required that cannot be achieved via manual syringe operation. A number of syringes and powered injectors for use therewith have, therefore, been developed for use in medical procedures such as angiography, computed tomography and NMR/MRI. For example, U.S. Pat. No. 5,383,858 discloses a front-loading syringe and powered injector in both pressure jacket and jacketless embodiments.

Despite these advances, however, conventional sterile packaged SP-SUD syringe injection systems are bulky. These large packages take up extra room in production inventory, shipping, hospital or clinic shelves prior to use, and in landfills after final disposal. Thus, as set forth with particularity in the appended claims, the present disclosure provides a compact packaging system for storing and shipping injection devices.

BRIEF SUMMARY

In one aspect, a nested syringe assembly is provided. The nested syringe assembly, comprises a first syringe having a cylindrical body defining an inner diameter; and a second syringe having a cylindrical body defining an outer diameter, wherein the outer diameter of the second syringe is less than the inner diameter of the first syringe, and wherein at least a portion of the cylindrical body of the second syringe is disposed within the cylindrical body of the first syringe.

In another aspect, the nested syringe assembly further comprises a first plunger seal assembly positioned within the cylinder body of the first syringe; and a second plunger seal assembly positioned within the cylinder body of the second syringe.

In another aspect, the nested syringe assembly, wherein the first plunger seal assembly positioned within the cylinder body of the first cylinder comprises: a seal ring; a snap ring positioned within the seal ring; and an engagement ring positioned within the seal ring.

In another aspect, the nested syringe assembly further comprises a plunger engagement mechanism.

In another aspect, the plunger engagement mechanism is in snap fit engagement with the snap ring.

In another aspect, the nested syringe assembly further comprises at last one resilient element configured to engage a piston of an injector.

In another aspect, the nested syringe assembly further comprises a key element defined by the engagement ring.

In another aspect, the first or second plunger seal assembly is compression set inside the first or second cylinder.

In another aspect, the nested syringe assembly further comprises at least one engagement feature, such as at least one lug, provided about the cylindrical body of either the first syringe or the second syringe, wherein the at least one engagement feature is configured to couple the first or second syringe to an injector port.

In another aspect, the at least one engagement feature comprises at least one tapered surface configured to contact a guide in a corresponding injector port for self-oriented alignment of the first or second syringe when the first or second syringe is inserted into the injector port.

In one aspect, a nested syringe assembly is provided. The nested syringe assembly comprises: a first syringe having a cylindrical body defining an inner diameter and terminating in a first tip; a second syringe having a cylindrical body defining an outer diameter and terminating in a second tip, wherein the outer diameter of the second syringe is less than the inner diameter of the first syringe, and wherein at least a portion of the cylindrical body of the second syringe is disposed within the proximal end of the cylindrical body of the first syringe; a base cap coupled to the proximal end of the cylindrical body of at least one of the first syringe and the second syringe, wherein at least a portion of the second syringe is disposed in the base cap; and a tip cap coupled to the tip of the first syringe.

In another aspect, the nested syringe assembly further comprises a flexible tube assembly disposed within the base cap.

In another aspect, the nested syringe assembly further comprises at least one fluid connector assembly disposed within the base cap.

In another aspect, the first syringe is in thread engagement with the base cap.

In another aspect, the first syringe is in thread engagement with the second syringe.

In another aspect, the second syringe is in thread engagement with the base cap.

In another aspect, the second syringe is in snap fit engagement with the base cap.

In another aspect, the first syringe is in snap fit engagement with the second syringe.

In another aspect, the nested syringe assembly further comprises an O-ring seal between the first syringe and the base cap.

In another aspect, the nested syringe assembly further comprises an O-ring seal between the second syringe and the base cap.

In another aspect, the second syringe comprises an interface diameter that is the same as the inner diameter of the first syringe.

In another aspect, the first and second syringes are positioned relative to each other with the first tip and the second tip directed in the same direction.

In another aspect, the first and second syringes are positioned relative to each other with the first tip and the second tip directed in the opposite direction.

In one aspect, a method of manufacturing a nested syringe assembly is provided, the method comprising: inserting a first plunger seal assembly within a cylinder body of a first syringe; inserting a second plunger seal assembly within a cylinder body of a second syringe; inserting at least a portion of the second syringe into a base cap; and coupling at least one of the first syringe and the second syringe to the base cap. In another aspect, the method may comprise inserting at least a portion of the cylinder body of the second syringe within the cylinder body of the first syringe.

In another aspect, the method comprises inserting a flexible tube assembly in the base cap.

In another aspect, the method comprises inserting at least one fluid connector assembly in the base cap.

In another aspect, the method comprises coupling a tip cap on a tip of the first syringe.

In another aspect, the addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 5 is a section view of the nested syringe assembly comprising the nested inner and outer syringes shown in FIG. 1, according to one aspect of the present disclosure.

FIG. 6 is a detail view of the tip cap engaged with features on the outer syringe, according to one aspect of the present disclosure.

FIG. 10 illustrates the outer syringe and a plunger seal assembly before (shown in solid line) and after (shown in phantom line) insertion into the cylindrical body of the outer syringe, according to one aspect of the present disclosure.

FIG. 11 is an exploded view of the plunger seal assembly shown in FIG. 10, according to one aspect of the present disclosure.

FIG. 12 illustrates a perspective section view of the plunger seal overmold assembly of the outer syringe shown in FIG. 10, according to one aspect of the present disclosure.

FIG. 13 illustrates a planar section view of the plunger seal assembly of the outer syringe shown in FIG. 10, according to one aspect of the present disclosure.

FIG. 17 illustrates the inner syringe and a plunger seal assembly before and after (shown in phantom) insertion into the inner syringe, according to one aspect of the present disclosure.

FIG. 18 is an exploded view of the plunger seal assembly shown in FIG. 17, according to one aspect of the present disclosure.

FIG. 19 illustrates a perspective section view of the plunger seal overmold assembly of the inner syringe shown in FIG. 17, according to one aspect of the present disclosure.

FIG. 20 illustrates a planar section view of the plunger seal assembly of the inner syringe shown in FIG. 17, according to one aspect of the present disclosure.

FIG. 25 is an exploded view of the fluid connector assembly, according to one aspect of the present disclosure.

FIG. 26 is a detailed view of the fluid connector, according to one aspect of the present disclosure.

FIG. 33 is a section view of a first configuration of a nested syringe assembly comprising an inner syringe nested within an outer syringe, according to one aspect of the present disclosure.

FIG. 34 illustrates a frangible tip cap of the nested syringe assembly configuration shown in FIG. 33, according to one aspect of the present disclosure.

FIG. 35 is a section view of the frangible tip cap shown in FIG. 34 illustrating the internal seal structure, according to one aspect of the present disclosure.

FIG. 36 is a detail view of one end of the outer syringe relative to the frangible base cap, according to one aspect of the present disclosure.

FIG. 37 is a detail section view of the thread and seal between the outer syringe and a frangible base cap, according to one aspect of the present disclosure.

FIG. 38 illustrates a flexible tube coiled about a collar with spikes located on bosses, according to one aspect of the present disclosure.

FIG. 39 is a section view through the base cap, according to one aspect of the present disclosure.

FIG. 55 illustrates attachment of the ends of a flexible tube to a collar held in a mandrel and to a moving arm, according to one aspect of the present disclosure.

FIG. 56 illustrates winding the flexible tube about the collar held in the mandrel, according to aspect of the present disclosure.

FIG. 57 illustrates a flexible tube sub-assembly wound about the collar, according to one aspect of the present disclosure.

FIG. 58 illustrates a plurality of flexible tube sub-assemblies ready for assembly in a base cap, according to one aspect of the present disclosure.

FIGS. 59-62 illustrate a process of assembling a wound flexible tube into a chamber defined by a base cap, according to one aspect of the present disclosure, where:

FIG. 59 Illustrates insertion of a flexible tube sub-assembly inside a chamber (retaining feature) defined in the base cap by a machine tool holder (e.g., gripper, chuck), according to one aspect of the present disclosure.

FIG. 60 Illustrates the flexible tube sub-assembly fully inserted into the chamber defined by the base cap, according to one aspect of the present disclosure.

FIG. 61 illustrates extraction of the collar from the flexible tube sub-assembly while the machine tool holder pushes against the wound flexible tube, according to one aspect of the present disclosure.

FIG. 62 illustrates the wound flexible tube fully assembled inside the chamber without the collar, according to one aspect of the present disclosure.

FIGS. 63-65 illustrate a process of assembling a flexible tube sub-assembly in a base cap, according to one aspect of the present disclosure, where:

FIG. 63 Illustrates insertion of a flexible tube sub-assembly into a base cap comprising a boss feature by a machine tool holder, according to one aspect of the present disclosure.

FIG. 64 illustrates the flexible tube sub-assembly fully inserted inside the base cap, according to one aspect of the present disclosure.

FIG. 65 illustrates the flexible tube sub-assembly inserted inside the base cap and the machine collar 906 retracted from the base cap, according to one aspect of the present disclosure.

FIG. 70 illustrates a first step in the loading sequence where the inner syringe of the nested syringe assembly is engaged with a locking mechanism through a first port of the fluid injector to releasably lock the inner syringe with the fluid injector into self-orienting alignment with the locking mechanism, according to one aspect of the present disclosure.

FIG. 71 illustrates a second step in the loading sequence where the outer syringe of the nested syringe assembly is engaged with a locking mechanism through a second port of the fluid injector to releasably lock the outer syringe with the fluid injector into self-orienting alignment with the locking mechanism, according to one aspect of the present disclosure.

FIG. 72 illustrates a first step in the unloading sequence where the outer syringe is subjected to a counterclockwise torque to unlock the outer syringe from the locking mechanism of the injector, according to one aspect of the present disclosure.

FIG. 73 illustrates a second step in the unloading sequence where the outer syringe is removed from the injector after being unlocked from the locking mechanism of the injector, according to one aspect of the present disclosure.

FIG. 74 is illustrates a third step in the unloading sequence where the outer syringe is located over the inner syringe, according to one aspect of the present disclosure.

FIG. 75 illustrates a fourth step in the unloading where the outer syringe is rotated into locking engagement with the inner syringe such that torque applied top the outer syringe is transmitted to the inner syringe to unlock the nested syringe assembly from the locking mechanism of the injector, according to one aspect of the present disclosure.

DETAILED DESCRIPTION

Figure 2:
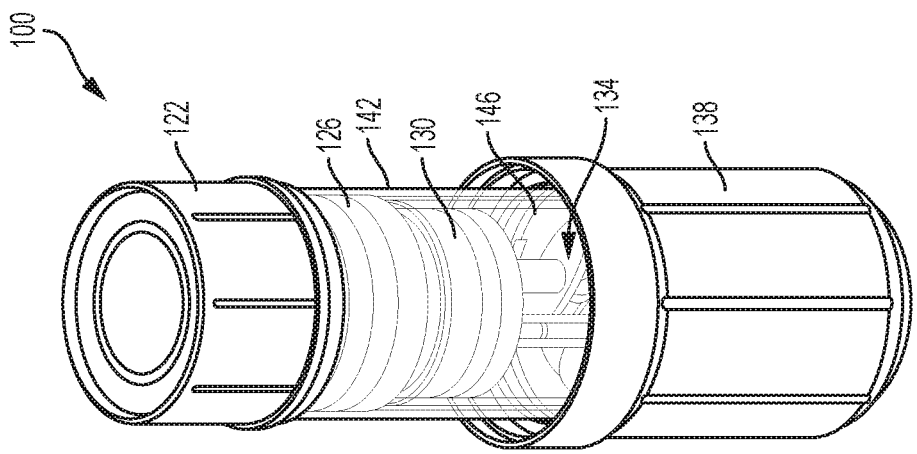
FIG. 2 is a perspective view of the nested syringe assembly comprising the nested inner and outer syringes shown in FIG. 1, according to one aspect of the present disclosure.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the spirit or scope of the subject matter presented here.

Before explaining the various aspects of the nested syringe assembly in detail, it should be noted that the various aspects disclosed herein are not limited in their application or use to the details of construction and arrangement of parts illustrated in the accompanying drawings and description. Rather, the disclosed devices may be positioned or incorporated in other embodiments, variations and modifications thereof, and may be practiced or carried out in various ways. Accordingly, aspects of the nested syringe assembly disclosed herein are illustrative in nature and are not meant to limit the scope or application thereof. Furthermore, unless otherwise indicated, the terms and expressions employed herein have been chosen for the purpose of describing the various aspects of the nested syringe assembly for the convenience of the reader and are not to limit the scope thereof. In addition, it should be understood that any one or more of the components of the nested syringe assembly, expressions thereof, and/or examples thereof, can be combined with any one or more of the other components, expressions thereof, and/or examples thereof, without limitation.

Also, in the following description, it is to be understood that terms such as front, back, inside, outside, top, bottom and the like are words of convenience and are not to be construed as limiting terms. As used herein, the term "proximal" when used to describe a portion of a syringe is generally used to indicate the portion of the syringe closer to the injector and the term "distal" when used to describe a portion of a syringe is generally used to indicate the portion of the syringe closer to the patient. Terminology used herein is not meant to be limiting insofar as devices described herein, or portions thereof, may be attached or utilized in other orientations. The various aspects of the nested syringe assembly will be described in more detail with reference to the drawings.

Figure 1:
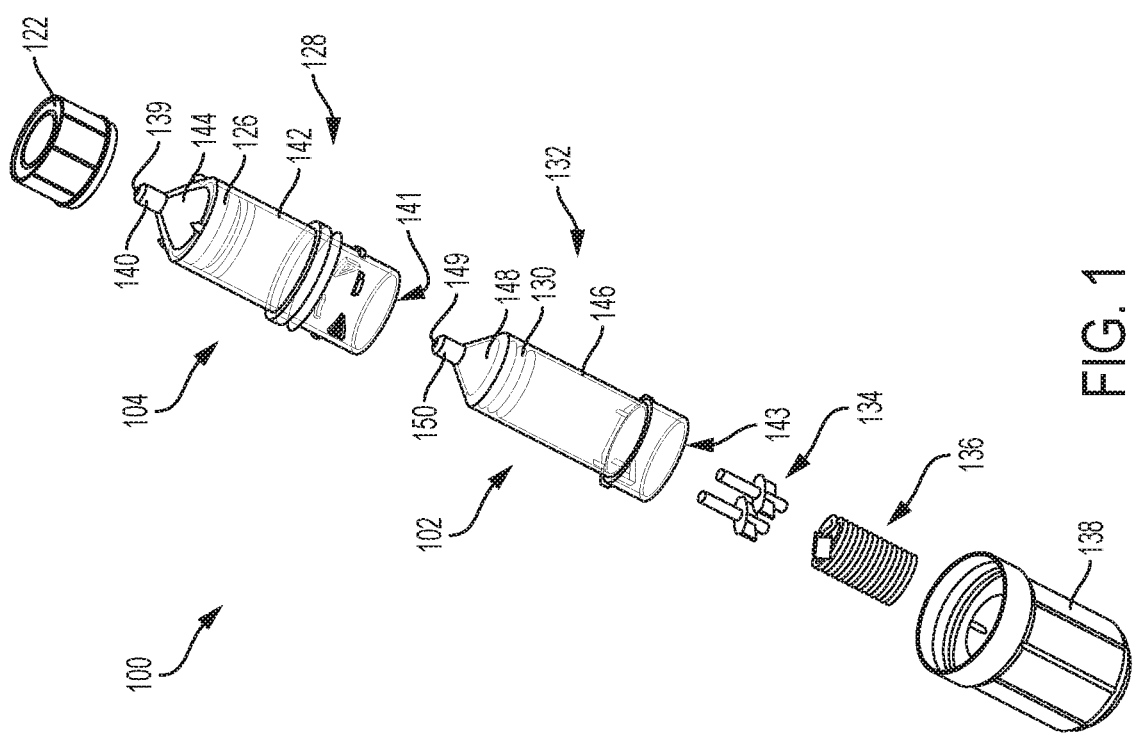
FIG. 1 is an exploded view of a nested syringe assembly comprising nested inner and outer syringes, according to one aspect of the present disclosure.

FIG. 1 is an exploded view of the nested syringe assembly 100 comprising a nested pair of inner and outer syringes 102, 104, according to one aspect of the present disclosure. The exploded view provides a clear illustration of the components of the nested syringe assembly 100. As shown, the nested syringe assembly 100 comprises a tip cap 122, an outer syringe 104 with a plunger seal assembly 126 positioned therein, an inner syringe 102 with a plunger seal assembly 130 positioned therein, a fluid connector assembly 134 including at least one spike, a wound flexible tube assembly 136, and a base cap 138. The nested syringe assembly 100 may further include a prime tube (flexible tube with a filter on the end) (not shown) for use when priming the syringe and tubing prior to an injection procedure.

Figure 4:
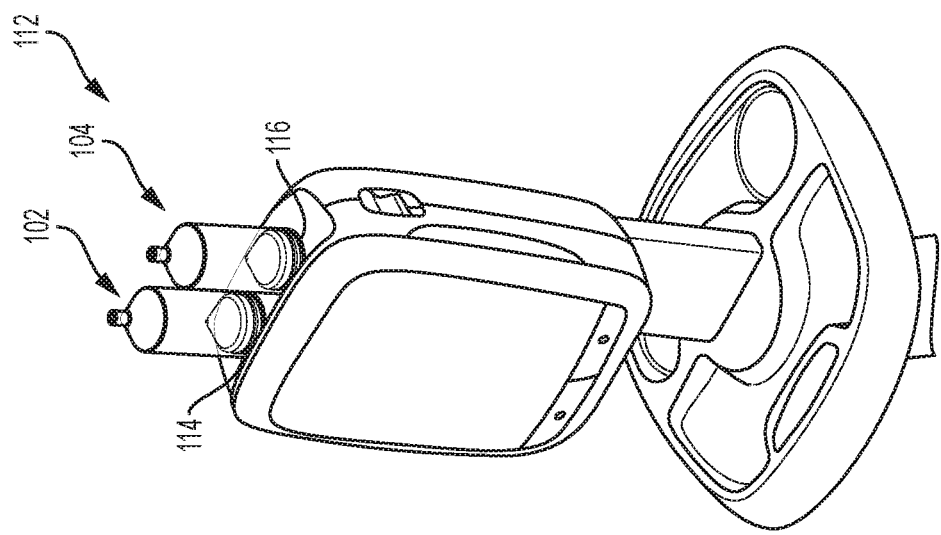
FIG. 4 illustrates an injector comprising the nested inner and outer syringes shown in FIG. 1 loaded on the injector, according to one aspect of the present disclosure.

The outer syringe 104 comprises a housing 128 (tube, barrel), that includes a cylindrical body 142, a conical portion 144 at a distal end, an injector interface 141 at a proximal end, and terminates in a distal tip 140 defining an orifice 139 for expelling fluids at a fluid delivery end of the housing 128. The tip 140 includes a threaded luer fitting or other suitable fitting, which is configured to engage the tip cap 122 and a corresponding fitting on tube assembly 136. The outer syringe plunger seal assembly 126 is positioned inside the bore of the housing 128 and partially within the conical portion 144 at the distal end of the housing 128. The outer syringe plunger seal assembly 126 fits tightly inside the bore of the cylindrical body 142 and can be pulled and pushed inside the cylindrical body 142 by a plunger drive piston allowing the outer syringe 104 to take in and expel fluids through the orifice 139 at the fluid delivery end of the housing 128. As described in more detail herein in connection with FIGS. 11 and 13, the plunger seal assembly 126 comprises snap and key features to engage a plunger drive piston (extension or stem) of the injector 112 (FIG. 4). The plunger drive piston pushes into engagement with the plunger seal assembly 126. Once engaged, the plunger drive piston pulls on the plunger seal assembly 126 to take fluids into the orifice 139. The plunger drive piston then pushes on the plunger seal assembly 126 to expel the fluids through the orifice 139 at the fluid delivery end of the housing 128.

The inner syringe 102 comprises a housing 132 (tube, barrel) that includes a cylindrical body 146, a conical portion 148 at a distal end, an injector interface 143 at a proximal end, and terminates in a distal tip 150 defining an orifice 149 for expelling fluids at a fluid delivery end of the housing 132. The tip 150 includes a threaded luer fitting or other suitable fitting configured to engage a corresponding fitting on tube assembly 136. The inner syringe plunger seal assembly 130 is positioned inside the housing 132 and partially within the conical portion 148 of the housing 132. The inner syringe plunger seal assembly 130 fits tightly inside the cylindrical body 146 and can be pulled and pushed inside the cylindrical body 146 allowing the inner syringe 102 to take in and expel fluids through the orifice 149 at the open end of the tube. As described in more detail below in connection with FIGS. 18 and 20, the plunger seal assembly 130 comprises snap and key features to engage a plunger drive piston (extension or stem) of the injector 112 (FIG. 4). The plunger drive piston pushes into engagement with the plunger seal assembly 130. Once engaged, the plunger drive piston pulls on the plunger seal assembly 130 to take fluids into the orifice 149 of the housing 132. The plunger drive piston pushes on the plunger seal assembly 130 to expel the fluids through the orifice 149 at the open end of the housing 132.

The nested syringe assembly 100 may be assembled in accordance with the following procedure. The flexible tube assembly 136, which may be wound or coiled to reduce space, is inserted into the base cap 138. The fluid connector assembly 134 is located into the wound flexible tube assembly 136. The inner syringe 102 is then inserted over the fluid connector 134 and the wound flexible tube 136 assemblies and is located within the base cap 138. The outer syringe 104 is located over the inner syringe 102 and is coupled to base cap 138 by tread engagement. The tip cap 122 is then coupled to the tip 140 of the outer syringe 104 by thread engagement. It will be appreciated that in addition to thread engagement, the various components may be connected using a variety of engagement means such as frictional, snap fit, socket, among others.

The nested syringe assembly 100 comprises a tip cap 122 and a base cap 138 to form the nested syringe assembly 100. The inner syringe has a housing with an outer diameter that is smaller than the inner diameter (e.g., bore diameter) of the outer syringe 104 housing 108 such that at least a portion of the inner syringe can be slidably received within the bore of the outer syringe 104. Although not shown in FIG. 1, the nested syringe assembly 100 may further comprise a frangible tip cap and a frangible base cap 138. These features are described in detail hereinbelow.

Although the housings 128, 132 of the inner and outer syringes 102, 104 are generally cylindrical, in other aspects of the present disclosure, the housings 128, 132 may be tapered. Furthermore, although the shape of the housings 128, 132 are shown to be substantially circular, other geometric configurations are contemplated to be within the scope of the present disclosure. Such geometric configurations include oval, square, rectangular, or other polygonal configurations. Details of the nested syringe assembly 100 includes variations thereof are disclosed hereinbelow.

FIG. 2 is a perspective view of a nested syringe assembly 100 comprising the nested inner and outer syringes 102, 104, according to one aspect of the present disclosure. The nested syringe assembly 100 provides a compact package with reduced shipping volume and lower sterilization costs. The inner and outer syringes 102, 104 are contained between a tip cap 122 and a base cap 138. The inner syringe 102 is slidably received within at least a portion of the housing of the outer syringe 104.

Figure 3:
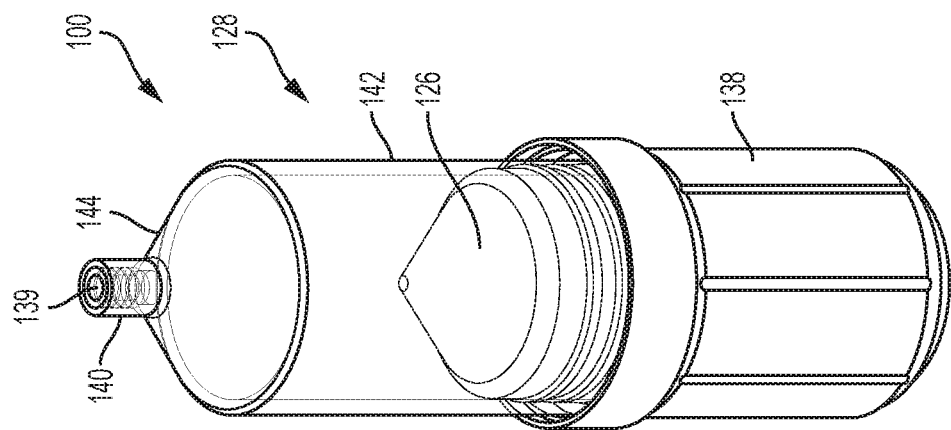
FIG. 3 illustrates a nested syringe assembly comprising an inner syringe nested within an outer syringe with the tip cap removed, according to one aspect of the present disclosure.

FIG. 3 illustrates the nested syringe assembly 100 shown in FIGS. 1 and 2, with the tip cap 122 removed. The inner syringe 102 as shown in FIG. 1, is located below the plunger seal assembly 126.

FIG. 4 illustrates an injector 112 comprising the nested inner and outer syringes 102, 104 shown in FIG. 1 loaded onto respective ports 114, 116 of the injector 112, according to one aspect of the present disclosure. The nested configuration of the syringe set 100 shown in FIG. 1, enables the user to initially install the inner syringe 102 of the nested assembly 100 into a first port 114 of the injector 112, remove the outer syringe 104 from the nested assembly 100, and insert the outer syringe 104 on a second port 116 of the injector 112.

Once the inner and outer syringes 102, 104 are inserted on the respective first and second ports 114, 116, the syringes 102, 104 can be connected with the tube assembly 136 and filled with suitable fluids from fluid connector assemblies connected to respective containers of medical fluid. For example, in one aspect, the outer syringe 104 may be filled with a saline fluid and the inner syringe 102 may be filled with a contrast fluid, such as a contrast imaging agent suitable for a CT, MRI or other suitable medical imaging process. The injector 112 is configured to inject or dispense the fluid medium contained in each of the inner and outer syringes 102, 104 in a controlled manner as may be required by medical procedures such as angiography, computed tomography and NMR/MRI. For example, U.S. Pat. No.

5,383,858 discloses a front-loading syringe and powered injector in both pressure jacket and jacketless embodiment.

FIG. 5 is a section view of the nested syringe assembly 100 comprising the nested inner and outer syringes 102, 104 shown in FIG. 4, according to one aspect of the present disclosure. The tip cap 122 is shown in thread engagement with the tip 140 of the outer syringe 104. The outer syringe plunger seal assembly 126 is located within the distal conical portion 144 of the housing 128. The cylindrical body 142 of the outer syringe 104 is shown in thread engagement with the base cap 138 to form a sealed system that maintains sterility of the inner portions of the assembly 100. The inner syringe 102 is slidably received within the bore of the cylindrical body 142 of the outer syringe 104. The tip 150 of the inner syringe 102 housing 132 and a portion of the conical portion 148 is partially received within the outer syringe plunger seal assembly 126. The cylindrical body 146 of the inner syringe 102 housing 132 is slidably disposed within the base cap 138. The inner syringe plunger seal assembly 130 is disposed within the distal conical portion 144 of the inner syringe 102. The fluid connector 134 and the wound flexible tube assembly 136 are located within a chamber 111 defined by the base cap 138. The fluid connector 134 comprises at least one spike 119 suitable for piercing a cap or septum of a fluid bottle or fluid bag. The wound flexible tube assembly 136 comprises a flexible tube 121 and fluid couplers 123. The nested syringe assembly 100 may further include a prime tube (flexible tube with a filter on the end) (not shown) for use when priming the syringe and tubing prior to an injection procedure. In one aspect, a shrink wrap seal 113 may be around the nested syringe assembly 100. In another aspect, the nested syringe assembly 100 may be contained within a flexible sterile package. After removal, the cap may also be act as a disposal "bin" for the spike and patient line luer caps.

FIG. 6 is a detail view of the tip cap 122 engaged with features 152 on the distal end of outer syringe 104, according to one aspect of the present disclosure. A plurality of engagement features 152 are located at the juncture between the cylindrical body 142 and the conical portion 144 of the outer syringe 104 housing 128. The engagement features 152 engage with serrated teeth 154 formed on a wall of the tip cap 122, for example to prevent accidental removal of tip cap 122 during shipping. This may also provide evidence of tampering, as the frangible ring on the lower end of the cap is broken off by the serrated engagement features when the cap is removed.

Figure 9:
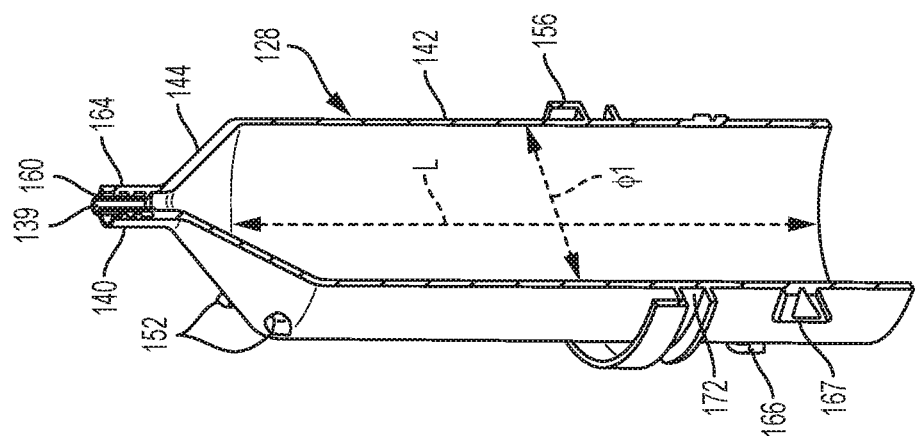
FIG. 9 is a section view of the outer syringe shown in FIG. 7 illustrating the internal volume dimensions of the outer syringe, according to one aspect of the present disclosure.
Figure 8:
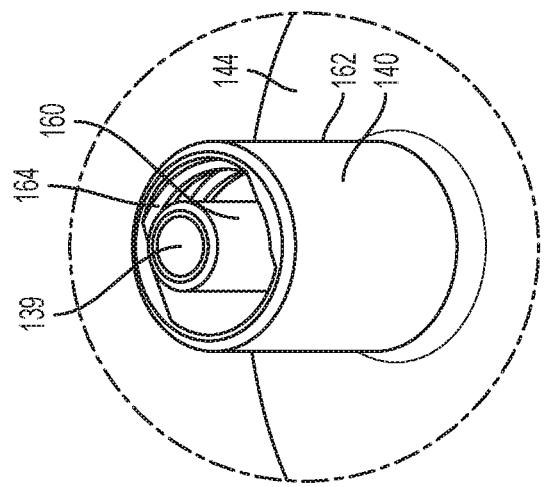
FIG. 8 is a detail of the syringe tip shown in FIG. 7 illustrating the sealing surface on an inner portion of the outer syringe tip, according to one aspect of the present disclosure.
Figure 7:
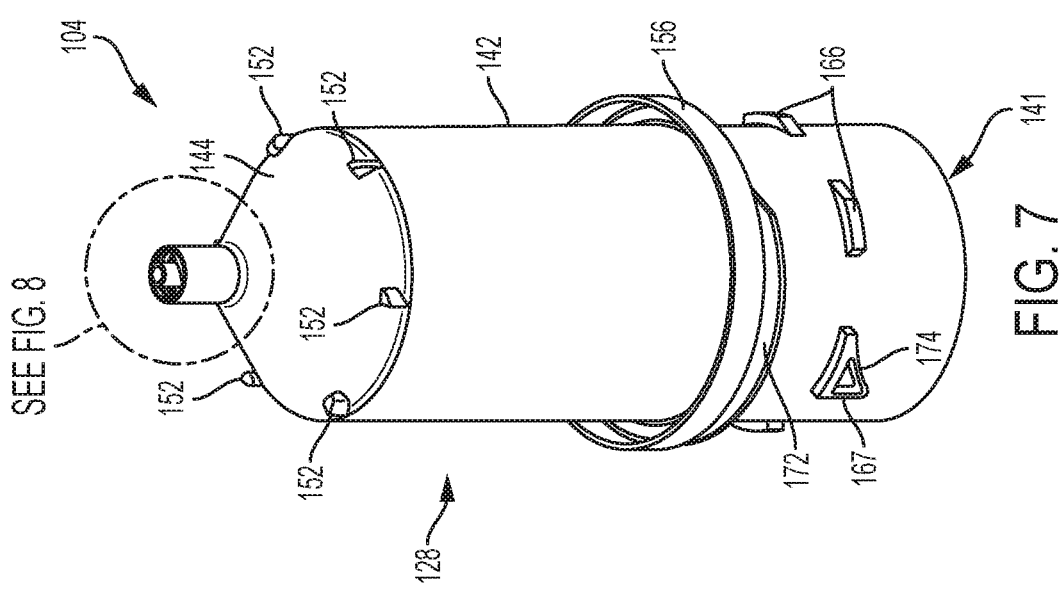
FIG. 7 is a perspective view of the outer syringe illustrating sealing surfaces on the housing of the outer syringe, according to one aspect of the present disclosure.

FIGS. 7-9 provide detailed illustrations of one aspect of the outer syringe 104. FIG. 7 is a perspective view of the outer syringe 104 illustrating sealing surfaces on the housing 128 of the outer syringe 104, according to one aspect of the present disclosure. One sealing feature 156 is formed on the cylindrical body 142 of the outer syringe 104. A groove 172 in the sealing feature 156 is configured to thread engage with a corresponding screw thread 158 formed inside the base cap 138 (FIG. 5). Also shown in FIG. 7 are the engagement features 152 that engage the serrated teeth 154 on the inner wall of the tip cap 122 (FIG. 6). Engagement features, such as lugs 166, 167 are provided about the outer wall of the cylindrical body 142 to couple the outer syringe 104 to one of the injector 112 (FIG. 2) ports. The tapered surfaces 174 on the engagement features 167 are configured to contact guides in a corresponding injector port when the outer syringe 104 is inserted into the injector port to self-orient the syringe 104 within the injector port and to axially eject the syringe 104 upon rotation within the port.

FIG. 8 is a detailed view of the tip 140 portion of the outer syringe 104 housing 128, according to one aspect of the present disclosure. The tip 140 comprises a threaded luer fitting comprising an outer cylindrical wall 162 and an inner cylindrical wall 160, which defines a sealing surface, and threads 164 formed on an inner portion of the outer cylindrical wall 162. The threads 164 also can be employed to couple the tip cap 122 (FIGS. 3-5) to the tip 140 by thread engagement or to the tube set 136. The orifice 139 is provided to transmit fluid into and out of the outer syringe 104.

FIG. 9 is a section view of the outer syringe 104 shown in FIG. 7 illustrating the internal volume dimensions of the outer syringe 104, according to one aspect of the present disclosure. The cylindrical body 142 of the outer syringe 104 has an internal bore diameter φ1 ranging from about 45 mm to about 48 mm and a length L ranging from about 100 mm to about 155 mm. The bore volume of the outer syringe 104 is about 150 mL and may range from about 50 mL to about 200 mL. This section view also shows the threads 164 defined by an interior portion of the outer cylindrical wall 162 of the tip 140 for coupling the tip cap 122 or tube set 136 by thread engagement to the tip 140. The inner cylindrical wall 160 that defines a sealing feature also is shown.

FIG. 10 illustrates the outer syringe 104 and a plunger seal assembly 126 before (shown in solid line) and after (shown in phantom line) insertion into the cylindrical body 142 of the outer syringe 104, according to one aspect of the present disclosure. The plunger seal assembly 126 is inserted into the open end 168 at the proximal end 141 of the cylindrical body 142 and is pushed in the direction shown by the arrow 170 into engagement with the internal wall of the conical portion 144 as shown in phantom line. The plunger seal assembly 126 has an outer diameter suitable for sealed engagement with the bore diameter φ1 of the cylindrical body 142. In one example, the outer diameter of the plunger seal assembly 126 is about 46.84 mm, without limitation. Accordingly, a Silicone lubricant may be applied to the interior portion of the cylindrical body 142 to reduce the insertion and kinetic friction between the plunger seal assembly 126 and an inner wall of the cylindrical body 142 as the plunger seal assembly is reciprocally moved within the cylindrical body 142 during fluid aspiration and delivery.

FIG. 11 is an exploded view of the plunger seal assembly 126 of the outer syringe 104 shown in FIG. 10, according to one aspect of the present disclosure. FIG. 12 illustrates a perspective section view of the plunger seal overmold assembly 176 shown in FIG. 11, according to one aspect of the present disclosure. FIG. 13 illustrates a planar section view of the plunger seal assembly 126 shown in FIG. 10, according to one aspect of the present disclosure.

With reference now to FIGS. 10-13, the plunger seal assembly 126 comprises a plunger seal overmold assembly 176, a snap ring 178, and an engagement ring 180. The plunger seal overmold assembly 176 comprises a seal ring 182 co-molded with a seal cone 184. The seal cone 184 comprises one or more sealing surfaces 185, 187 defined on an exterior portion and annular flanges 188, 196 defined on an interior portion.

With reference now to FIGS. 11-13, the plunger seal assembly 126 can be assembled in accordance with the following procedure. First, the plunger seal snap ring 178 is inserted into the plunger seal overmold assembly 176 in the direction shown by the arrow 186 until an annular flange 183 defined by the snap ring 178 engages an annular flange 188 defined by an interior wall 192 of the seal ring 182. Second, when the snap ring 178 is properly positioned on the annular flange 188, the engagement ring 180 is inserted into the seal ring 182 in the direction shown by the arrow 194 until an annular flange 195 defined by the engagement ring 180 engages an annular flange 196 defined by the interior wall 192 of the seal ring 182. It will be appreciated that the diameters of the sealing surfaces 185, 187 and the base 200 of the engagement ring 180 may be the same. Although, the disclosure is not limited in this context.

As shown in FIGS. 11 and 13, the engagement ring 180 comprises a circular base 200. A wall portion 204 of the engagement ring 180 extends from the circular base 200 in the longitudinal direction. As shown, the engagement ring 180 is not engaged with the snap ring 178. However, as additional force is applied in the direction of the arrow 194 the engagement ring 180 engages the snap ring 178 when the engagement ring 180 is fully inserted into the seal ring 182.

Figure 16:
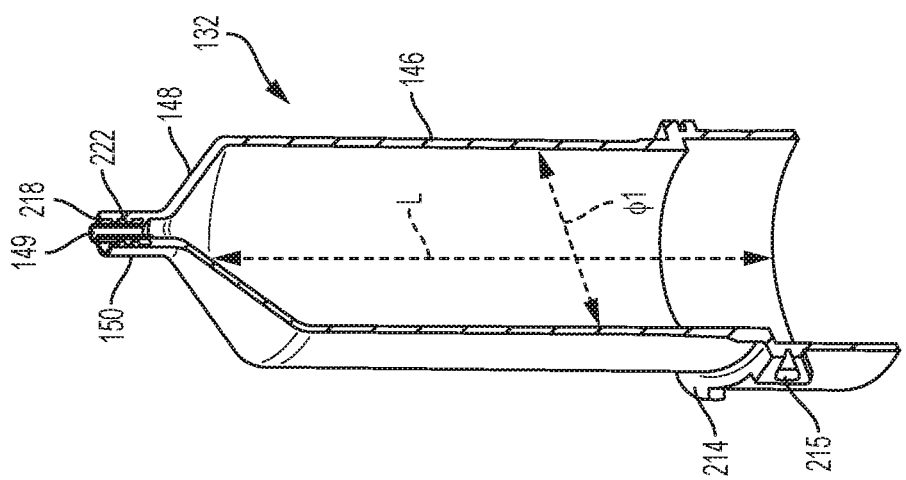
FIG. 16 is a section view of the inner syringe shown in FIG. 14 illustrating the internal volume dimensions of the inner syringe, according to one aspect of the present disclosure.
Figure 15:
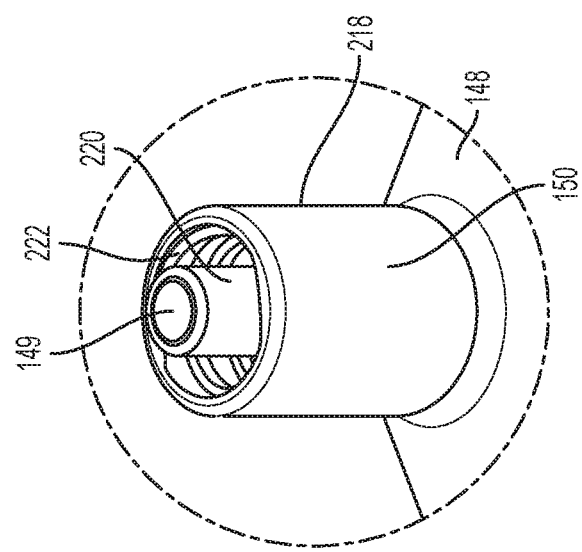
FIG. 15 is a detail of the syringe tip shown in FIG. 14 illustrating the sealing surface on an inner portion of the inner syringe tip, according to one aspect of the present disclosure.
Figure 14:
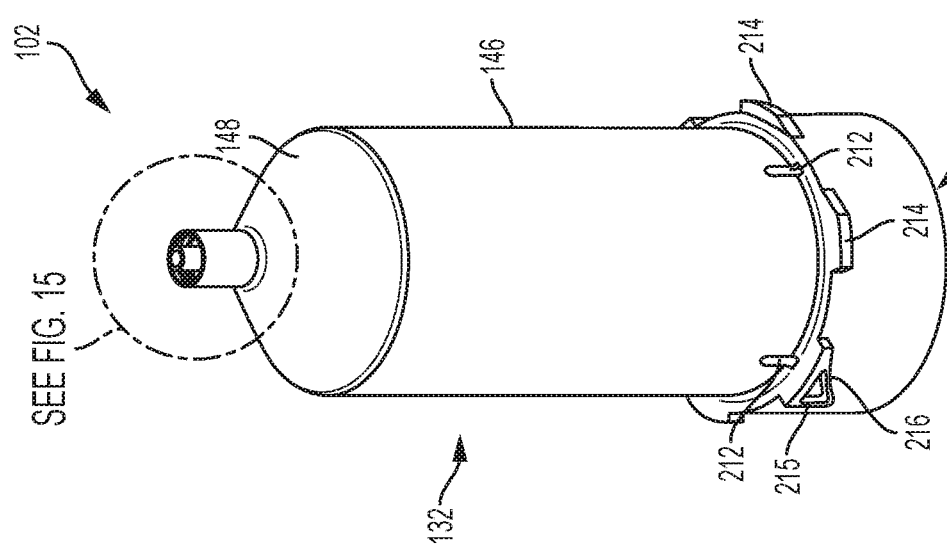
FIG. 14 is a perspective view of the inner syringe illustrating sealing surfaces on an outer portion of the inner syringe and an inner surface of the inner syringe tip, according to one aspect of the present disclosure.

FIGS. 14-16 provide detailed illustrations of the inner syringe 102. FIG. 14 is a perspective view of the inner syringe 102 illustrating sealing surfaces on the housing 132 of the inner syringe 102, according to one aspect of the present disclosure. Compression features 212 are located near the proximal end of the cylindrical body 146 of the inner syringe 102 to provide a friction fit with the inner surface of the outer syringe 104 (FIG. 5) once the outer syringe 104 is inserted over the inner syringe 102. Engagement features 214, 215 are formed about the outer circumference of the cylindrical body 146 to facilitate releasable coupling of the inner syringe 102 to one of the injector 112 (FIG. 2) ports. The tapered surfaces 216 on the engagement features 215 are configured to contact guides in a corresponding injector port when the inner syringe 102 is inserted into the injector port to further facilitate self-oriented coupling of the proximal end 143 of the inner syringe 102 to the injector 112 port.

FIG. 15 is a detailed view of the tip 150 portion of the inner syringe 102 housing 132, according to one aspect of the present disclosure. The tip 150 comprises a threaded luer fitting comprising an outer cylindrical wall 218, an inner cylindrical wall 220, which defines a sealing surface, and threads 222 formed on an inner portion of the outer cylindrical wall 218.

FIG. 16 is a section view of the inner syringe 102 shown in FIG. 14 illustrating the internal volume dimensions of the inner syringe 102, according to one aspect of the present disclosure. The cylindrical body 146 of the inner syringe 102 has a bore diameter φ1 ranging from about 39 mm to about 42 mm and a length L ranging from about 66 mm to about 100 mm. The bore volume of the inner syringe 102 ranges from about 50 mL to about 150 mL and in certain aspects may be about 100 mL. This section view also shows the threads 222 defined by an inner portion of the outer cylindrical wall 218 of the tip 150

FIG. 17 illustrates the inner syringe 102 and a plunger seal assembly 130 before (shown in solid line) and after (shown in phantom line) insertion into the cylindrical body 146 of the inner syringe 102, according to one aspect of the present disclosure. The plunger seal assembly 130 is inserted into the open end 224 of the proximal end of cylindrical body 146 and is pushed in the direction shown by the arrow 226 into engagement with the internal wall of the conical portion 148 as shown in phantom line. The plunger seal assembly 130 has an outer diameter suitable for sealed engagement with the bore diameter φ1 of the cylindrical body 146. In one example, the outer diameter of the plunger seal assembly 130 is about 41.00 mm, without limitation. Accordingly, a Silicone lubricant may be applied to the interior portion of the cylindrical body 146 to reduce the insertion and kinetic friction between the plunger seal assembly 130 and an inner wall of the cylindrical body 146 as the plunger seal assembly is reciprocally moved within the cylindrical body 142 during fluid aspiration and delivery.

FIG. 18 is an exploded view of the plunger seal assembly 130 of the inner syringe 102 shown in FIG. 17, according to one aspect of the present disclosure. FIG. 19 illustrates a perspective section view of the plunger seal overmold assembly 228 shown in FIG. 17, according to one aspect of the present disclosure. FIG. 20 illustrates a planar section view of the plunger seal assembly 130 shown in FIG. 17, according to one aspect of the present disclosure.

With reference now to FIGS. 17-20, the plunger seal assembly 130 comprises a plunger seal overmold assembly 228, a snap ring 230, and an engagement ring 232. The plunger seal overmold assembly 228 comprises a seal ring 234 co-molded with a seal cone 236. The seal cone 236 comprises one or more sealing surfaces 235, 237 defined on an exterior portion and annular flanges 238, 240 defined on an interior portion to reduce or prevent compression set over a long period of time.

With reference now to FIGS. 18-20, the plunger seal assembly 130 can be assembled in accordance with the following procedure. First, the plunger seal snap ring 230 is inserted into the plunger seal overmold assembly 228 in the direction shown by the arrow 242 until an annular flange 244 defined by the snap ring 230 engages an annular flange 246 defined by an interior wall 248 of the seal ring 234. Second, when the snap ring 230 is properly positioned on the annular flange 246, the engagement ring 232 is inserted into the seal ring 234 in the direction shown by the arrow 250 until an annular flange 245 defined by the engagement ring 232 engages an annular flange 252 defined by the interior wall 248 of the seal ring 234. It will be appreciated that the diameters of the sealing surfaces 235, 237 and the base 254 of the engagement ring 232 may be the same. Although, the disclosure is not limited in this context.

As shown in FIGS. 18 and 20, the engagement ring 232 comprises a circular base 254. A wall portion 258 of the engagement ring 232 extends from the circular base 254 in the longitudinal direction. The engagement ring 232 engages the snap ring 230 when the engagement ring 232 is fully inserted into the seal ring 234.

Figure 22:
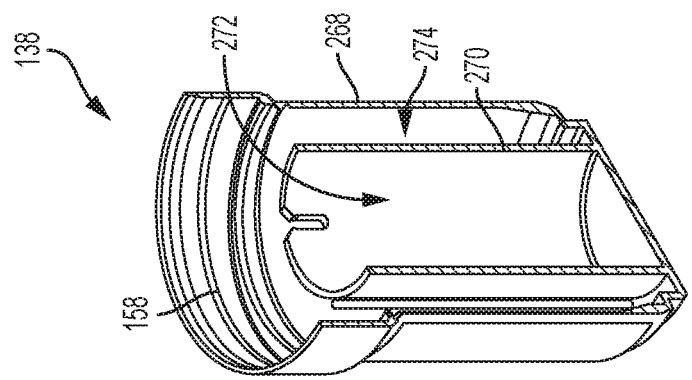
FIG. 22 is a section view of the base cap, according to one aspect of the present disclosure.
Figure 21:
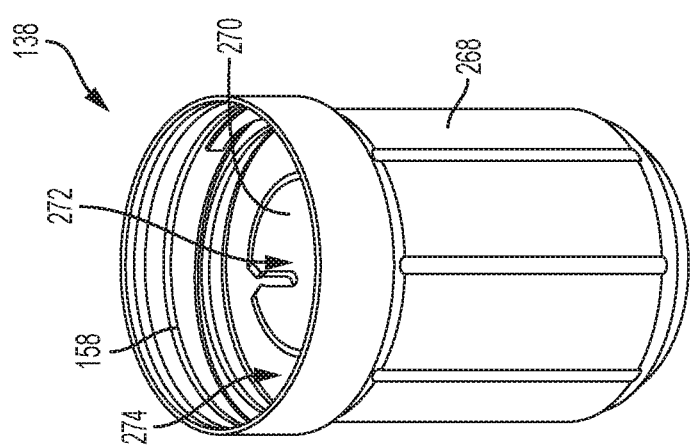
FIG. 21 is a perspective view of the base cap, according to one aspect of the present disclosure.
Figure 24:
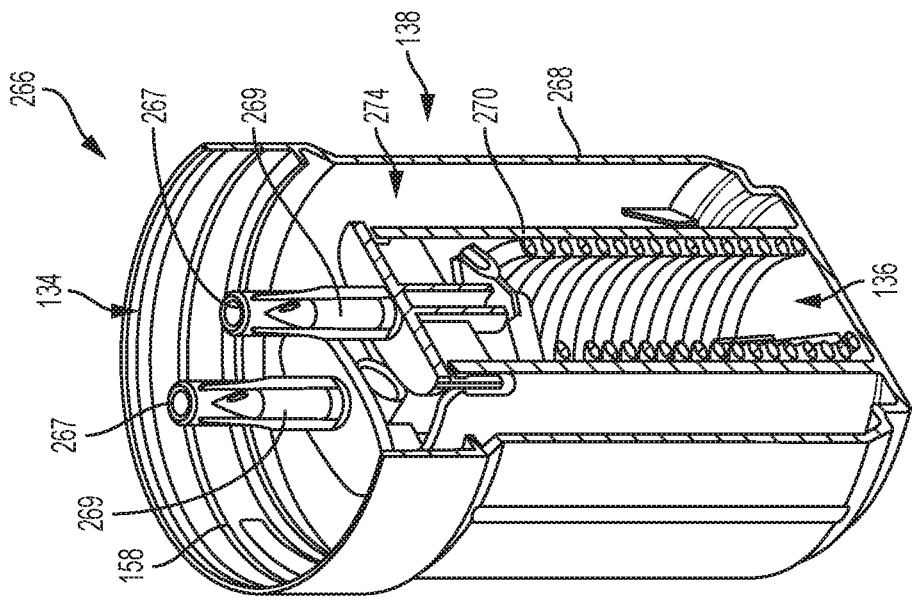
FIG. 24 is a partial section view of the base cap assembly shown in FIG. 21, according to one aspect of the present disclosure.
Figure 23:
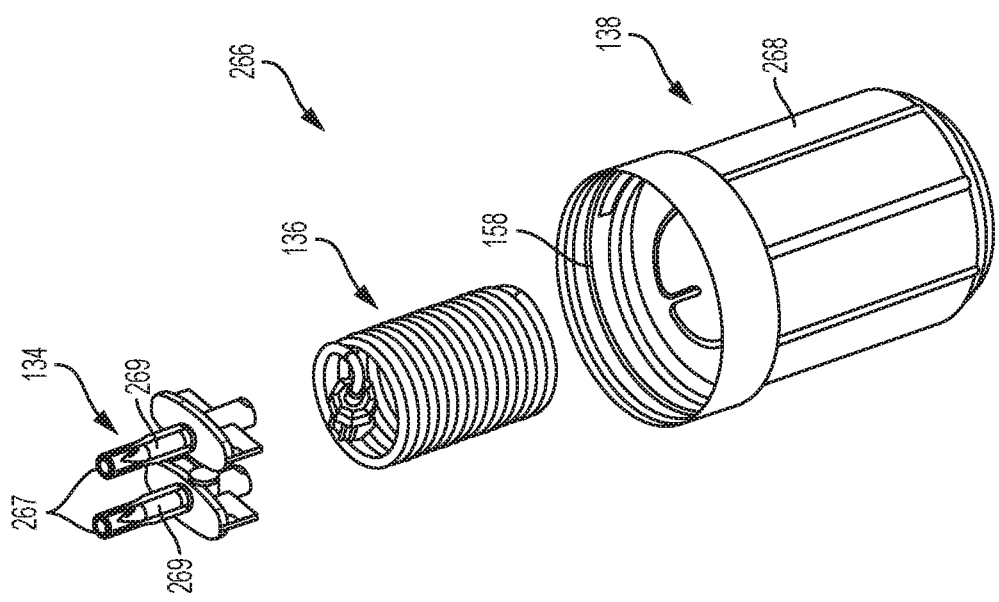
FIG. 23 is an exploded view of a base cap assembly, according to aspect of the present disclosure.

FIG. 21 is a perspective view of the base cap 138, according to one aspect of the present disclosure. FIG. 22 is a section view of the base cap 138, according to one aspect of the present disclosure. With reference to FIGS. 21 and 22, the base cap 138 comprises an outer wall 268 and an inner wall 270. The upper interior portion of the outer wall 268 comprises screw threads 158 to engage the sealing feature 156 on the outer portion of the cylindrical body 142 of the outer syringe 104. The inner wall 270 defines an opening 272 suitable for receiving a fluid connector assembly 134 and tube assembly 136 as illustrated in FIGS. 23 and 24. An annular opening 274 is defined between the outer wall 268 and the inner wall 270. The annular opening 274 is suitable for receiving at least one of the cylindrical body of the inner syringe 102 and the cylindrical body of the outer syringe 104 (FIG. 1).

FIG. 23 is an exploded view of a base cap assembly 266, according to an aspect of the present disclosure. The base cap assembly 266 comprises a base cap 138, a wound flexible tube assembly 136, and a fluid connector assembly 134 with caps 267 positioned over the spikes 269. FIG. 24 is a partial section view of the base cap assembly 266 shown in FIG. 23, according to an aspect of the present disclosure. With reference to both FIGS. 23 and 24, the wound flexible tube assembly 136 is nested inside an opening 272 defined by the inner wall 270. The fluid connector assembly 134 is then positioned over the wound flexible tube assembly 136. The nested syringe assembly 100 may further include a prime tube (flexible tube with a filter on the end)(not shown) for use when priming the syringe and tubing prior to an injection procedure. As will be apparent, other arrangements of the fluid connector assembly 134 and tube assembly 136 within opening 272 are possible. The proximal end of at least one of the inner syringe 102 and outer syringe 104 (FIG. 1) is located over the inner wall 270 in the space 274 defined between the outer wall 268 and the inner wall 270.

FIG. 25 is an exploded view of a fluid connector 276, according to one aspect of the present disclosure. The fluid connector 276 includes a cap 267 slidably disposed over the piercing spike 269. FIG. 26 is a detailed view of the fluid connector 276, according to one aspect of the present disclosure. With reference now to both FIGS. 25 and 26, the fluid connector 276 includes a piercing spike 269 to pierce a septum or elastomeric stopper of a fluid container or bottle to place a fluid line or channel passing through the spike 269 of the fluid connector 276 in fluid connection with the container or bottle. The fluid connector 276 also may include a check ball or other check valve and air filter in fluid connection with an air line or vent line passing through the spike 269. As used herein, the term "spike" refers generally to an extending section which tapers over at least a portion thereof to a generally pointed end suitable for piercing. The fluid connector 276 is used to connect a fluid source to the syringe. For example, the fluid connector 276 may be used to connect the inner syringe 102 to a contrast fluid bottle and the outer syringe 104 to a saline fluid bottle, or vice versa. The spike 269 is in fluid communication with first and second ports 280, 282. As shown in FIG. 25, a seal 278 is placed over one of the fluid ports 280. In other embodiments, an air filter may be placed over port 280 to allow air flow into the container and equalize pressure during withdrawal of fluid from the container. The filter may allow air to pass into the container while preventing pathogenic contaminants from entering the container. Fluid port 282 may be threadably connected directly to luer connector tip 140, 150 during filing or may be connected to tip 140, 150 by an intermediate tubing section, thereby providing fluid communication between the fluid container and the interior of the syringe.

Figure 28:
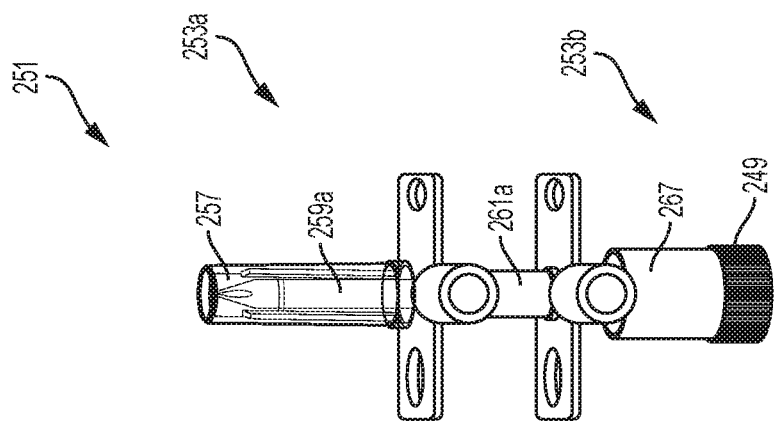
FIG. 28 is an assembled view of the matable fluid connector shown in FIG. 27 in a mated configuration, according to one aspect of the present disclosure.
Figure 27:
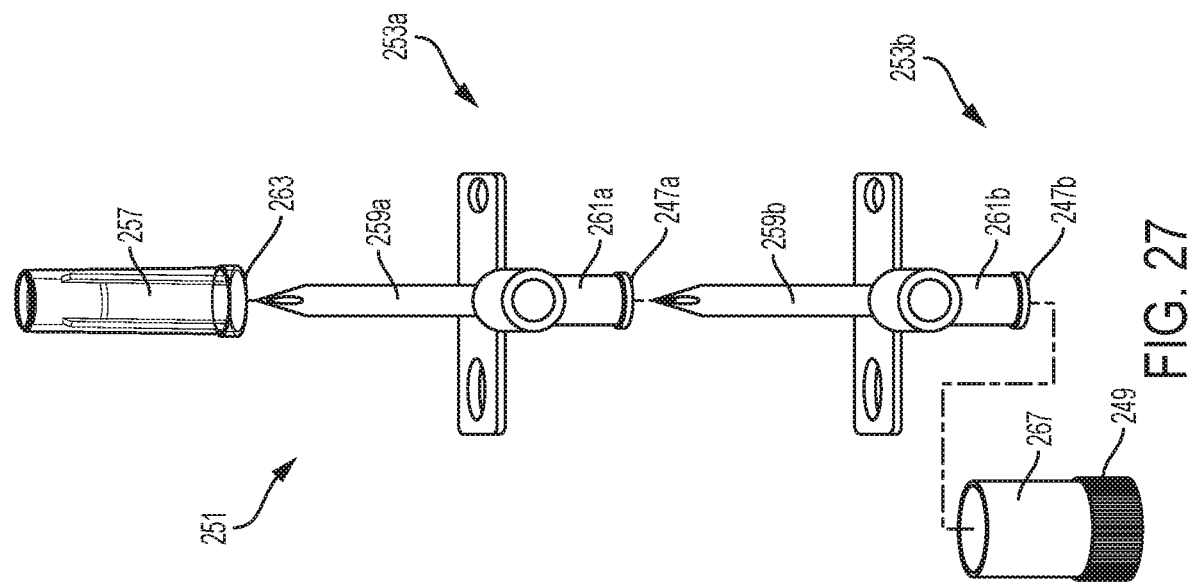
FIG. 27 is an exploded view of a matable fluid connector assembly, according to one aspect of the present disclosure.

FIG. 27 is an exploded view of a matable fluid connector assembly 251, according to one aspect of the present disclosure. In one aspect, the matable fluid connector assembly 251 comprises a first fluid connectors 253a and a second fluid assembly 253b. The first and second fluid connectors 253a, 253b are structurally identical and interchangeable. FIG. 28 is an assembled view of the matable fluid connector 251 shown in FIG. 27 in a mated configuration, according to one aspect of the present disclosure. With reference to FIGS. 27-28, the first fluid connector 253a comprises a cap 257, a spike 259a, and a fluid port 261a in fluid communication with the spike 259a. The cap 257 defines an opening 263 for receiving the spike 259a of the first fluid connector 253a. The fluid port 261a defines an opening 247a for receiving a spike 259b from the second fluid connector 253b. The second fluid connector 253b comprises a fluid port 261b in fluid communication with the spike 259b. The fluid port 261b includes a protective cap 249 that is removed prior to use and a fluid port coupling 267 that is fluidically coupled to the second fluid port 261b. The first and second fluid connectors 253a, 253b are mated by insertion along the dashed lines. Once the first and second fluid connectors 253a, 253b are mated, they form the compact fluid connector assembly 251 shown in FIG. 28. The structural similarity of the first and second fluid connectors 253a, 253b makes them interchangeable from an assembly perspective.

Figure 30:
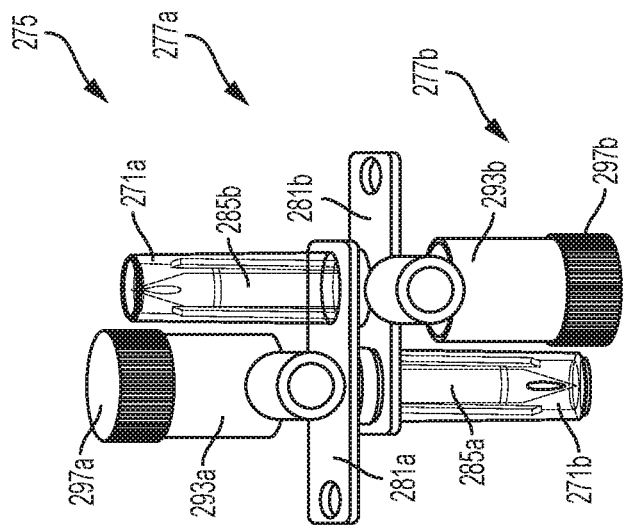
FIG. 30 is an assembled view of the matable fluid connector shown in FIG. 29 in a mated configuration, according to one aspect of the present disclosure.
Figure 29:
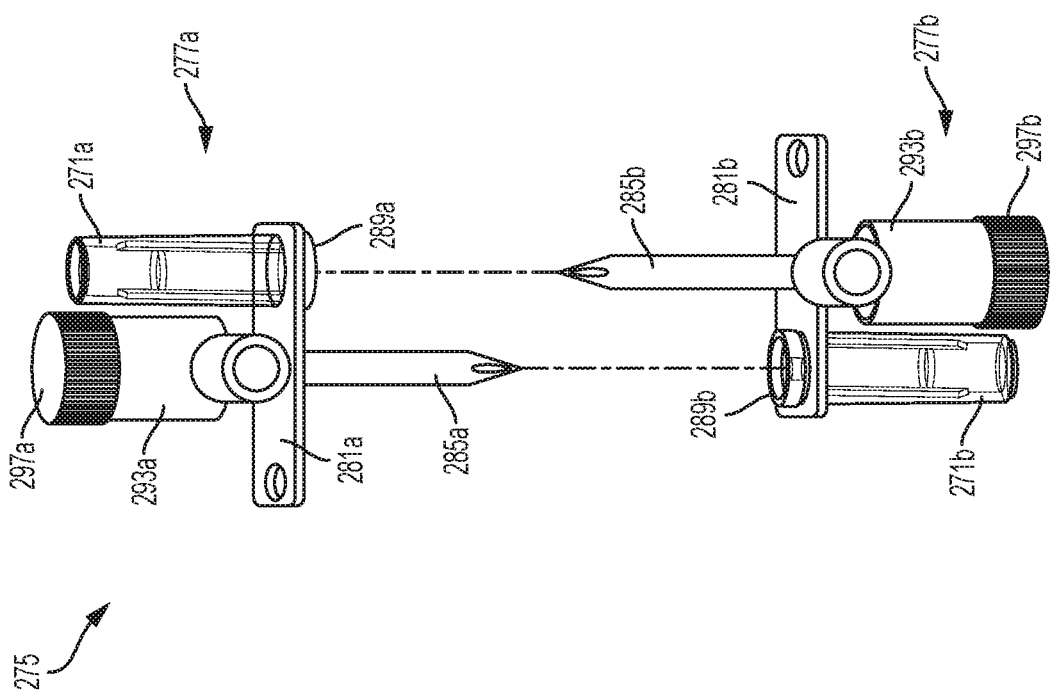
FIG. 29 is an exploded view of a matable fluid connector assembly, according to one aspect of the present disclosure.

FIG. 29 is an exploded view of a matable fluid connector assembly 275, according to one aspect of the present disclosure. In one aspect, the matable fluid connector assembly 275 comprises a first fluid connector 277a and a second fluid connector 277b. The first and second fluid connectors 277a, 277b are structurally identical and interchangeable. FIG. 30 is an assembled view of the matable fluid connector 275 shown in FIG. 29 in a mated configuration, according to one aspect of the present disclosure. With reference to FIGS. 29-30, the first fluid connector 277a comprises a cap 271a integrally formed or attached to a flange 281a. The fluid port coupling 293a comprises a protective cap 297a which is removed prior to use. A spike 285a is coupled to and is in fluid communication with the fluid port coupling 293a. The cap 271a defines an opening for receiving a spike 285b of the second fluid connector 277b. The second fluid connector 277b is structurally identical to the first fluid connector 277a and also includes a cap 271b formed integrally with or connected to a flange 281b. The fluid port coupling 293b comprises a protective cap 297b that is removed prior to use. The cap 271b defines an opening 289b to receive the spike 285a of the first fluid connector 277a. The first and second fluid connectors 277a, 277b are mated by insertion along the dashed lines. Once the first and second fluid connectors 277a, 277b are mated, they form the compact fluid connector assembly 275 shown in FIG. 30. The structural similarity of the first and second fluid connectors 277a, 277b makes them interchangeable from an assembly perspective.

Figure 32:
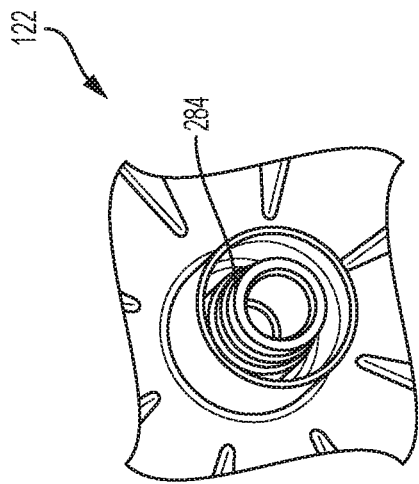
FIG. 32 is a detail view of the tip cap, according to one aspect of the present disclosure.
Figure 31:
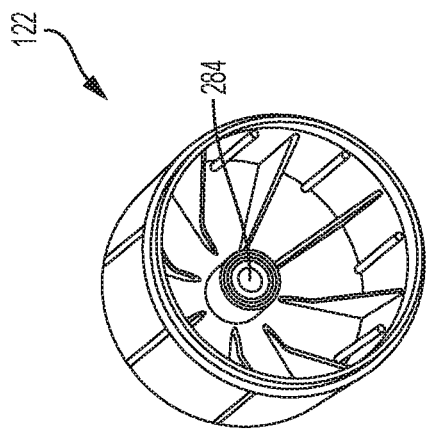
FIG. 31 is a perspective view of the tip cap, according to one aspect of the present disclosure.

FIG. 31 is a perspective view of the tip cap 122, according to one aspect of the present disclosure. FIG. 32 is a detail view of the tip cap 122, according to one aspect of the present disclosure. The tip cap 122 comprises a threaded fitting 284 suitable for thread engagement with the luer connector tip 140 of the outer syringe 104 (FIGS. 7-9).

FIG. 33 is a section view of a first configuration of a nested syringe assembly 300 comprising an inner syringe 302 nested at least partially within an outer syringe 304, according to one aspect of the present disclosure. The nested syringe assembly 300 also comprises a frangible tip cap 306 with a threaded seal 308 shown in more detail in FIG. 34 and in section view in FIG. 35 and a base cap 322. The proximal end of outer syringe 304 is in thread engagement with the inner syringe 302. The inner syringe 302 may be employed to inject contrast. The inner syringe 302 may have a bore diameter $\varphi 1$ of about 43 mm and defines a volume of about 80 mL. The outer syringe 304 may be employed to inject saline fluid. The outer syringe 304 may have a bore diameter $\varphi 2$ of about 50 mm and defines a volume of about 130 mL. In one aspect, the overall length L of the nested syringe assembly 300 is about 260 mm and there may be an overlap of about 33 mm between the inner and outer syringes 302, 304. In another aspect, the inner syringe 302 and the outer syringe 304 may have the same diameter.

The frangible tip cap 306 is in thread engagement with the tip 310 of the outer syringe 304. The tip 310 defines a threaded luer fitting suitable for fluidically coupling the outer syringe 304 to a fluid container or bottle through a fluid connector assembly 312 and for connecting to flexible tubing system 314.

The fluid connector assembly 312 comprises a flexible tube 314 with luer fittings wound about a collar 313 and a fluid connector 316 comprising piercing spikes 318 suitable for puncturing fluid containers or bottles. The fluid connector assembly 312 is positioned inside an opening 320 defined by a frangible base cap 322. FIG. 38 illustrates the flexible tube 314 coiled about a collar 313 or bobbin with piercing spikes 318 located on bosses, according to one aspect of the present disclosure. The nested syringe assembly 300 may further include a prime tube (flexible tube with a filter on the end) (not shown) for use when priming the syringe and tubing prior to an injection procedure. FIG. 39 is a section view through the base cap 322, according to one aspect of the present disclosure, showing the fluid connector assembly 312 positioned inside the opening 320 defined by the frangible base cap 322.

An inner syringe plunger assembly 324 is disposed within the bore of the inner syringe 302. The inner syringe 302 is slidably disposed inside the base cap 322 and forms an annular snap joint with the base cap 322. The inner syringe 302 comprises a tip 326 comprising a threaded luer fitting suitable for fluidically coupling the inner syringe 302 to a fluid container or bottle through the fluid connector assembly 312 and for connecting to flexible tubing system 314, stored within a chamber 320 defined in the base cap 322.

An outer syringe plunger assembly 328 is slidably disposed within the bore 330 of the outer syringe 304. As shown in FIG. 37, the outer syringe 304 is inserted into the opening 334 defined by the base cap 322, according to one aspect of the present disclosure. As shown in FIG. 36, injector port alignment features 327 are provided about the circumference of the outer syringe 304. The alignment features 327, such as protruding lugs, facilitate self-oriented positioning the outer syringe 304 into an injector port in the proper orientation. Although not shown, similar alignment features may be provided about the circumference of the housing of the inner syringe 302 to facilitate self-oriented positioning the inner syringe 302 into an injector port in the proper orientation. The alignment features 327 may comprise at least one tapered surface 305, 307. In the example shown in FIG. 36, the alignment features 327 comprise two tapered surface 305, 307, for example.

As shown in detail in FIG. 37, the base cap 322 comprises external threads 332 to engage internal threads 321 of the outer syringe 304. The internal threads 321 of the outer syringe 304 engage the external threads 332 of the base cap 322 to sealingly connect the outer syringe 304 to the base cap 322. Alternatively, the base cap 322 and the outer syringe 304 form an annular snap joint or may connect using a bayonet type fit. A protruding component 325, e.g., a hook, stud or bead is deflected briefly during the joining operation and catches either a protrusion or depression 327 (undercut) formed in the outer syringe 304 mating component. The outer syringe 304 is rotated into thread engagement with the base cap 322 until the bottom edge 323 of the syringe contacts a seat 336 and the protruding component 325 snaps onto the depression 327 to connect and hermetically seal the outer syringe 304 to the base cap 322.

Figure 40:
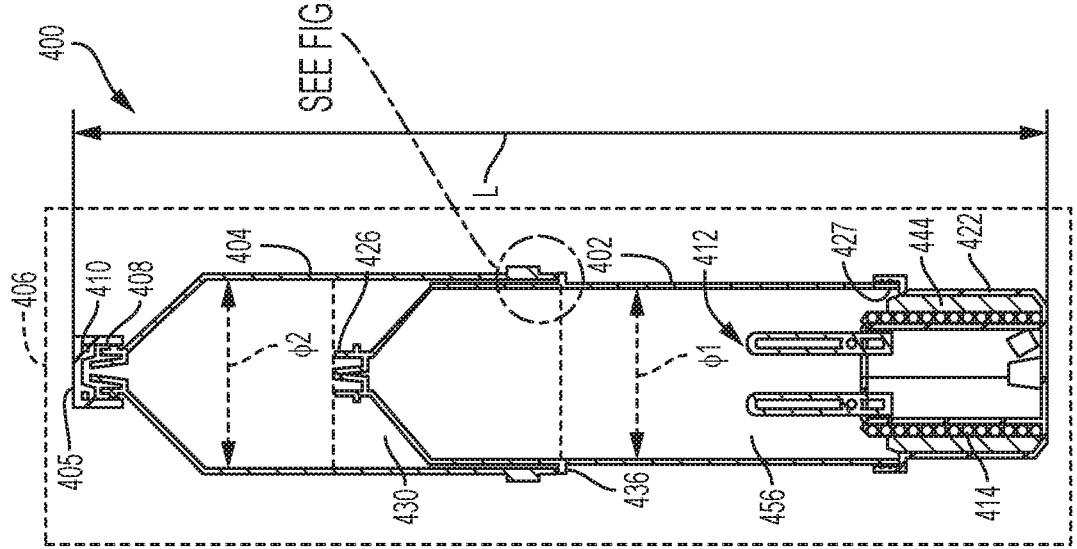
FIG. 40 is a section view of another configuration of a nested syringe assembly comprising an inner syringe nested within an outer syringe located within a sealed bag, according to one aspect of the present disclosure.

FIG. 40 is a section view of another configuration of a nested syringe assembly 400 comprising an inner syringe 402 nested at least partially within an outer syringe 404 located within a sealed bag 406, according to one aspect of the present disclosure. The nested syringe assembly 400 also comprises a frangible tip cap 405 with a threaded seal 408 and a base cap 422. The inner syringe 402 may be employed to inject contrast fluid. The inner syringe 402 may have a bore diameter φ1 of about 43 mm and defines a volume of about 130 mL. The outer syringe 404 may be employed to inject saline fluid. The outer syringe 404 may have a bore φ2 of about 50 mm and defines a volume of about 180 mL. In one aspect, the overall length L of the nested syringe assembly 400 is about 252 mm and there may be an overlap of about 60 mm between the inner and outer syringes 402, 404. The nested syringe assembly 400 within sealed bag 406 provides a compact package for easy storage and shipping.

The frangible tip cap 405 is in thread engagement with the tip 410 of the outer syringe 404. The tip 410 defines a threaded luer fitting suitable for fluidically coupling the outer syringe 404 to a fluid container or bottle through a fluid connector assembly 412 and for connecting to flexible tubing system 414, stored within a chamber 420 defined in the base cap 422.

An inner syringe plunger assembly (not shown) may be disposed within a proximal opening 456 defined by the inner syringe 402 barrel or tube. The inner syringe 402 is slidably disposed inside the base cap 422 and is snap fitted to the base cap 422. The inner syringe 402 comprises a tip 426 comprising a threaded luer fitting suitable for fluidically coupling the inner syringe 402 to a fluid container or bottle through the fluid connector assembly 412 and for connecting to flexible tubing system 414. The inner syringe 402 is positioned within a seal edge 427 defined about the circumference of the base cap 422 and can be in thread engagement or snap engagement with the base cap 422. As shown in FIG. 40, the inner syringe 402 is in thread engagement with the base cap 422. In other aspects, for example, a protruding component, e.g., a hook, stud or bead, provided on the base cap 422 may be deflected briefly during the joining operation to catch either a protrusion or depression (undercut) formed in the inner syringe 402 mating component.

Figure 41:
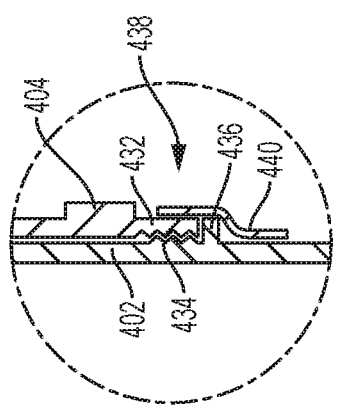
FIG. 41 illustrates a detail view of a threaded joint between inner and outer syringes and a tamper evident heat seal disposed thereon, according to one aspect of the present disclosure.

An outer syringe plunger assembly (not shown) may be disposed within a proximal opening 430 defined by the outer syringe 404 barrel or tube. The outer syringe 404 includes internal threads 432 to engage external threads the 434 formed on inner syringe 404 to form a hermitic seal therebetween. As shown in FIG. 41, the outer syringe 404 is threaded over the inner syringe 402 until the outer syringe 404 contacts an edge 436 located just beneath the external threads 434 of the inner syringe 402. Accordingly, the inner syringe 402 is in thread engagement with the outer syringe 404 to form a threaded joint 438. A tamper evident seal 440 may be positioned over the threaded joint 438. Although, not shown, injector port alignment features may be provided about the circumference of the housing of the inner and outer syringes 402, 404. The alignment features assist in positioning the inner and outer syringes 402, 404 into the injector ports in the proper orientation.

Figure 42:
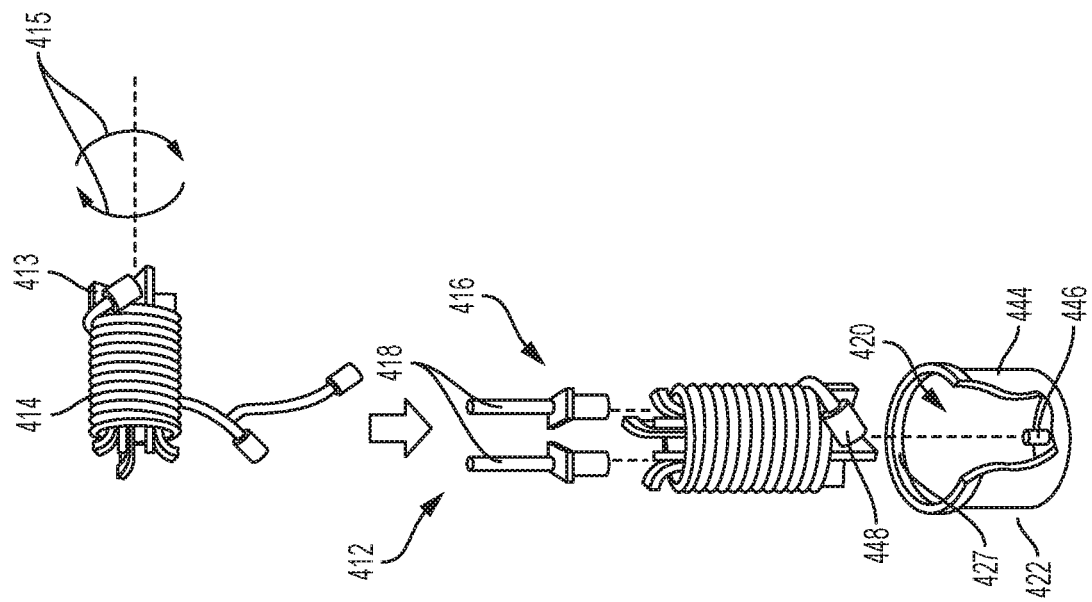
FIG. 42 illustrates a flexible tube assembled about a cruciform, with spikes installed on bosses, and inserted into a frangible base cap.

FIG. 42 illustrates a flexible tube 414 assembled about a cruciform 413, with piercing spikes 418 installed on bosses, and inserted into a frangible base cap 422. The fluid connector assembly 412 comprises a flexible tube 414 with luer fittings wound about the cruciform 413 (or collar, bobbin, etc.), as shown by the arrows 415, and a fluid connector 416 comprising piercing spikes 418 suitable for puncturing fluid containers or bottles. The fluid connector assembly 412 is positioned inside a chamber 420 defined by an internal wall 444 in the frangible base cap 422. A protruding feature 446 (boss element) can be provided in the base of the chamber 420 to align the fluid connector assembly 412 during the assembly procedure. The flexible tube 414 comprises at least one luer fitting 448 to fluidically couple the syringe 402, 404 to the fluid supply or to a patient catheter. The nested syringe assembly 400 may further include a prime tube (flexible tube with a filter on the end) (not shown) for use when priming the syringe and tubing prior to an injection procedure.

Figure 43:
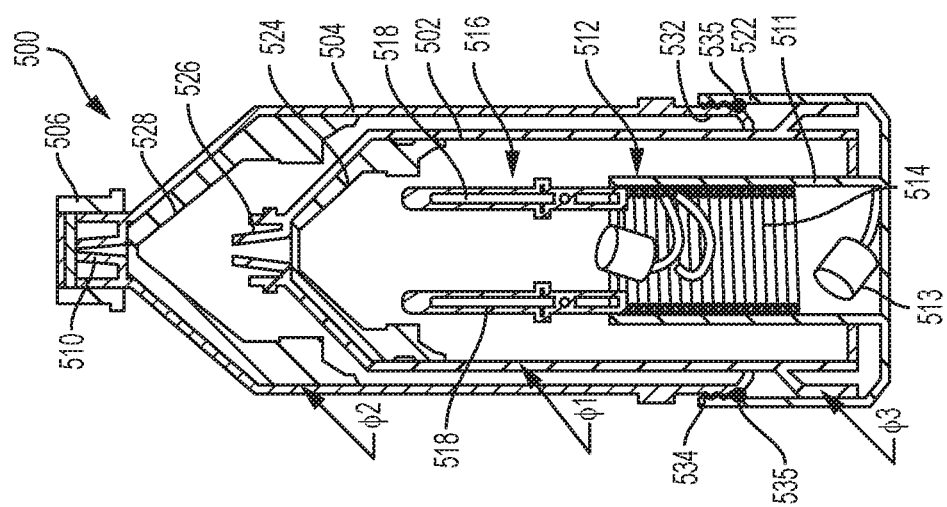
FIG. 43 is a section view of another configuration of a nested syringe assembly comprising an inner syringe nested within an outer syringe with the same interface diameters, according to one aspect of the present disclosure.

FIG. 43 is a section view of another configuration of a nested syringe assembly 500 comprising an inner syringe 502 at least partially nested within an outer syringe 504 with the same interface diameters, according to one aspect of the present disclosure. The nested syringe assembly 500 also comprises a frangible tip cap 506 with either a friction fit or threaded seal and a base cap 522. The inner syringe 502 may be employed to inject contrast fluid. The inner syringe 502 may have a bore diameter φ1 of about 41 mm and defines a volume of about 118 mL. The outer syringe 504 may be employed to inject saline fluid. The outer syringe 504 may have a bore diameter φ2 of about 50 mm and defines a volume of about 180 mL. The inner syringe 502 also has an interface diameter φ3 that is the same as the bore diameter φ2 of the outer syringe 504, e.g., about 50 mm. In one aspect, the overall length L of the nested syringe assembly 500 is about 160 mm and there may be substantial overlap between the inner and outer syringes 502, 504. The overall diameter of the nested syringe assembly 500 is about 65 mm.

The frangible tip cap 506 is in thread engagement with the tip 510 of the outer syringe 504. The tip 510 defines a threaded luer fitting suitable for fluidically coupling the outer syringe 504 to a fluid container or bottle through a fluid connector assembly 512 and for connecting to flexible tubing system 514 stored within a chamber 511 defined in the base cap 522.

The inner syringe 502 is slidably disposed inside the base cap 522 and the interface diameter of the inner syringe 502 is in friction fit with an interior wall of the base cap 522. The inner syringe 502 comprises a tip 526 comprising a threaded luer fitting suitable for fluidically coupling the inner syringe 502 to a fluid container or bottle through the fluid connector assembly 512 and for connecting to flexible tubing system 514.

The outer syringe 504 is in thread engagement with the base cap 522 by way of external threads 534 on the outer syringe 504 barrel and internal threads 532 on an internal wall of the base cap 522. The outer syringe 504 also includes an O-ring seal 535 disposed about the outer circumference of the outer syringe 504 to sealingly engage an inner surface of the base cap 522. As shown in FIG. 39, the outer syringe 504 is threaded inside the base cap 522. Although, not shown, injector port alignment features may be provided about the circumference of the housing of the inner and outer syringes 502, 504. The alignment features facilitate positioning the inner and outer syringes 502, 504 into the injector ports in the proper orientation.

An inner syringe plunger assembly 524 is disposed within the bore of the inner syringe 502 and an outer syringe plunger assembly 528 is disposed within the bore of the outer syringe 504. The inner and outer syringe plunger assemblies 524, 528 are assembled in a distal end of the syringe barrels and are compression set as shown in FIG. 43.

Figure 44:
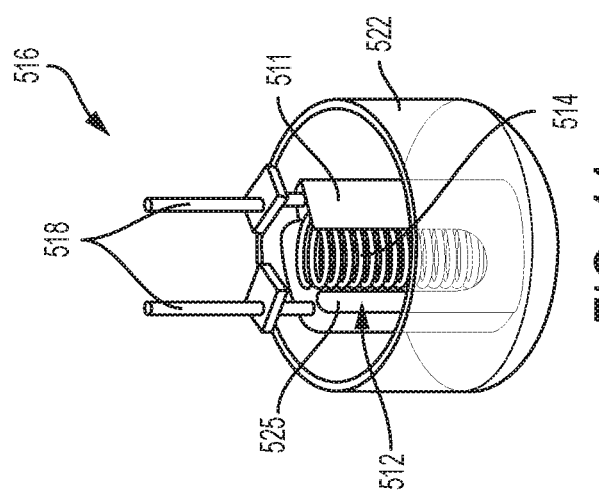
FIG. 44 illustrates a detail view of a frangible base cap with a flexible tube positioned within the frangible base cap, according to one aspect of the present disclosure.

A fluid connector assembly 512 is disposed in the chamber 511 defined in the base cap 522. The flexible tube 514 is wound about a collar 513 or bobbin and comprises at least one fluid connector 516 comprising piercing spikes 518 suitable for puncturing fluid containers or bottles. FIG. 44 illustrates the flexible tube 514 wound about a collar 513 and positioned within the chamber 511 in the base cap 522. An aperture 525 is provided in a wall of the chamber 511 to provide access to the fluid connector assembly 512.

Figure 45:
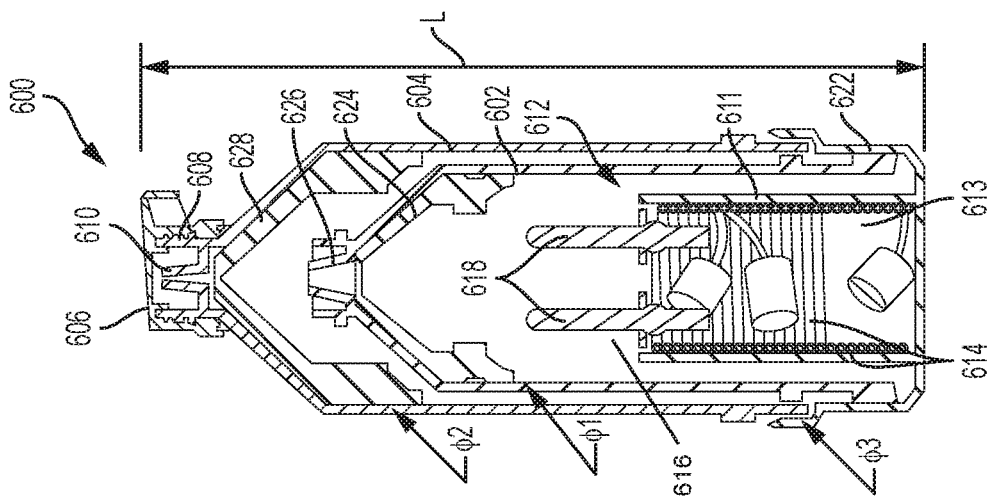
FIG. 45 is a section view of another configuration of a nested syringe assembly comprising an inner syringe nested within an outer syringe, according to one aspect of the present disclosure.

FIG. 45 is a section view of another configuration of a nested syringe assembly 600 comprising an inner syringe nested 602 at least partially within an outer syringe 604, according to one aspect of the present disclosure. The nested syringe assembly 600 also comprises a frangible tip cap 606 with a threaded seal 608 and a base cap 622. The inner syringe 602 may be employed to inject contrast fluid. The inner syringe 602 may have a bore diameter φ1 of about 41 mm and defines a volume of about 80 mL. The outer syringe 604 may be employed to inject saline fluid. The outer syringe 604 may have a bore diameter φ2 of about 50 mm and defines a volume of about 130 mL. In one aspect, the overall length L of the nested syringe assembly 600 is about 152 mm and there may be substantial overlap between the inner and outer syringes 602, 604. The overall diameter φ3 of the nested syringe assembly 600 is about 58 mm.

Figure 47:
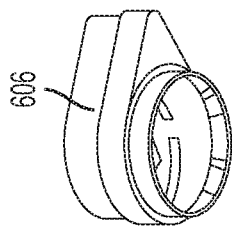
FIG. 47 illustrates a detailed perspective view of the tear drop shaped tip cap, according to one aspect of the present disclosure.
Figure 46:
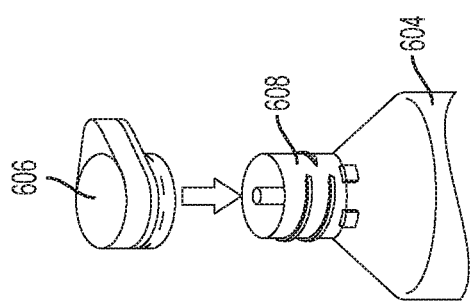
FIG. 46 illustrates a tip cap having a tear drop configuration positioned relative to the outer syringe, according to one aspect of the present disclosure.

As shown in FIGS. 45-47, the frangible tip cap 606 has a tear drop form to provide a better grip. The frangible tip cap 606 is in thread engagement with the tip 610 of the outer syringe 604. The tip 610 defines a threaded luer fitting suitable for fluidically coupling the outer syringe 604 to a fluid container or bottle through a fluid connector assembly 612 and for connecting to flexible tubing system 614 stored within a chamber 611 defined in the base cap 622.

With reference now back to FIG. 45, the inner syringe 602 is slidably disposed inside the base cap 622 and is in friction fit with an interior wall of the base cap 622. The inner syringe 602 comprises a tip 626 comprising a threaded luer fitting suitable for fluidically coupling the inner syringe 602 to a fluid container or bottle through the fluid connector assembly 612 and for connecting to flexible tubing system 614.

Figure 50:
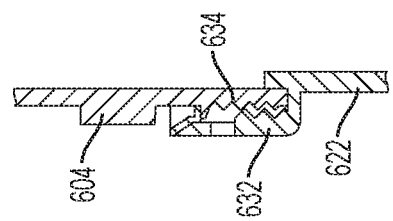
FIG. 50 illustrates a detailed view of a threaded connection between the outer syringe and the frangible base cap, according to one aspect of the present disclosure.
Figure 48:
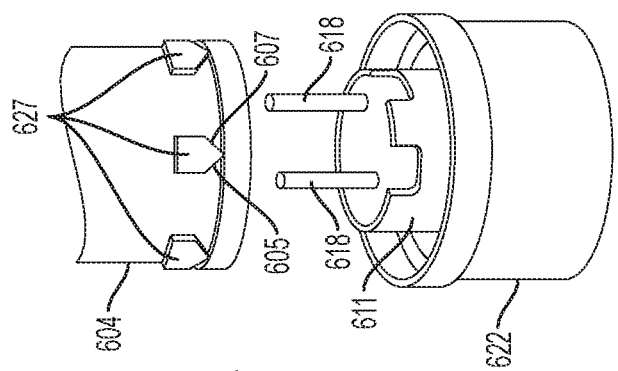
FIG. 48 is a detail view of the outer syringe positioned relative to the frangible base cap, according to one aspect of the present disclosure.

As shown in FIGS. 45 and 50, the outer syringe 604 is in thread engagement with the base cap 622 by way of external threads 634 on the outer syringe 604 and internal threads 632 on an internal wall of the base cap 622. FIG. 50 illustrates a detailed view of the threaded connection between the outer syringe 604 and the frangible base cap 622. The outer syringe 604 is threaded inside the base cap 622. Optionally, the base cap 622 may comprise an annular snap fit joint to couple the outer syringe 604. As shown in FIG. 48, injector port alignment features 627 are provided about the circumference of the outer syringe 604 barrel. The alignment features 627 facilitate positioning the outer syringe 604 into the injector ports in the proper orientation. Although not show, similar alignment features are provided on the outer barrel of the inner syringe 602 to facilitate positioning the inner syringe 602 into the injector ports in the proper orientation. The alignment features 627 comprise at least one tapered surface 605, 607. In the example illustrated in FIG. 48, the alignment features 627 comprise two tapered surfaces 605, 607, for example.

An inner syringe plunger assembly 624 is disposed within the bore of the inner syringe 602 and an outer syringe plunger assembly 628 is disposed within the bore of the outer syringe 604. The inner and outer syringe plunger assemblies 624, 628 are assembled in a proximal end of the syringe barrels and are compression set as shown in FIG. 45.

Still with reference to FIG. 45, a fluid connector assembly 612 is disposed in the chamber 611 defined in the base cap 622. The flexible tube 614 is wound about a collar 613 or bobbin and comprises at least one fluid connector 616 comprising piercing spikes 618 suitable for puncturing fluid containers or bottles. FIG. 45 illustrates the flexible tube 614 wound about the collar 613 and positioned within the chamber 611 in the base cap 622. The flexible tube 614 further comprises a plurality of luer fittings to fluidically couple the inner and outer syringes 602, 604 to a fluid source and with a patient catheter.

Figure 49:
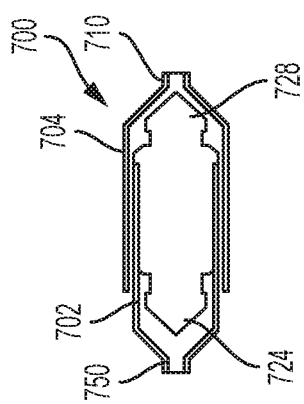
FIG. 49 illustrates yet another configuration of a nested syringe assembly comprising an inner syringe nested within an outer syringe, according to one aspect of the present disclosure.

FIG. 49 illustrates yet another configuration of a nested syringe assembly 700 comprising an inner syringe 702 nested within an outer syringe 704, according to one aspect of the present disclosure. As shown in FIG. 49, the nested syringes 702, 704 are oriented such that the tips 710, 750 point in opposite directions. An inner syringe plunger assembly 724 is disposed within the bore of the inner syringe 702 and an outer syringe plunger assembly 728 is disposed within the bore of the outer syringe 704.

Figure 51:
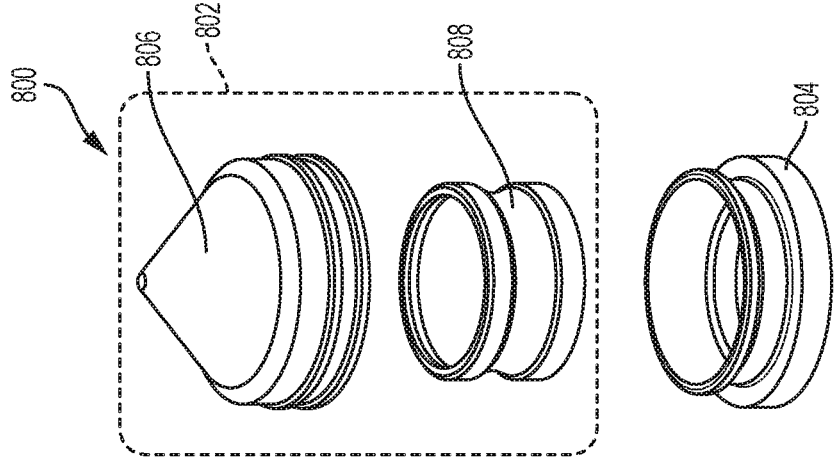
FIG. 51 is an exploded view of an expanding plunger seal assembly, according to one aspect of the present disclosure.

FIG. 51 is an exploded view of an expanding plunger seal assembly 800, according to one aspect of the present disclosure. The expanding plunger seal assembly 800 comprises a co-molded plunger seal overmold assembly 802 and an engagement ring 804. The co-molded plunger seal overmold assembly 802 comprises a co-molded plunger cap 806 or seal cone and a plunger seal 808. The engagement ring 804 comprises a plurality of snap features 808 and ramps 819, 820 that engage the inner wall of the plunger seal 808.

Figure 52:
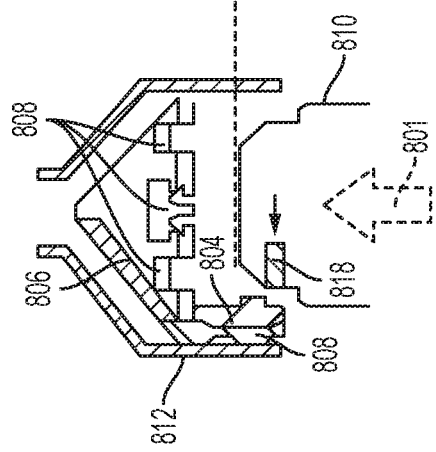
FIG. 52 is a section view of the expanding plunger seal assembly prior to engagement by a piston drive head, according to one aspect of the present disclosure.

FIG. 52 is a section view of the expanding plunger seal assembly 800 prior to engagement by a piston drive head 810, according to one aspect of the present disclosure. The expanding plunger seal assembly 800 is assembled inside the syringe 812 bore with the engagement ring 804 loosely disposed therein. Upon activation, for example, during an injection procedure, piston drive head 810 pushes the expanding plunger seal assembly 800 into the distal conical end of the syringe in the direction indicated by the arrow 801. The piston drive head 810 includes an engagement pin 818.

Figure 53:
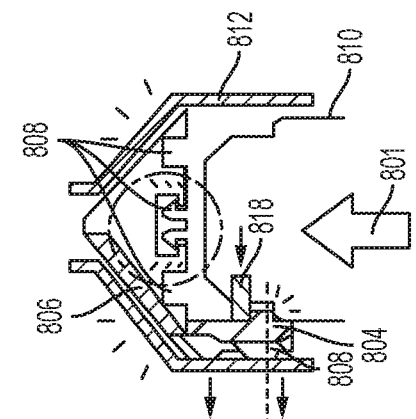
FIG. 53 is a section view of the expanding plunger seal assembly shown in FIG. 51 after engagement by the piston drive head, according to one aspect of the present disclosure.

FIG. 53 is a section view of the expanding plunger seal assembly 800 shown in FIG. 51 after engagement by the piston drive head 810, according to one aspect of the present disclosure. The piston drive head 810 engages and pushes the engagement ring 804 which snaps into connection with the plunger cap 806. As the piston drive head 810 is advanced distally in the direction indicated by the arrow 801, the engagement pin 818 engages the engagement ring 804 to compress set the plunger seal 808 against the inner wall 820 of the syringe 812.

Figure 54:
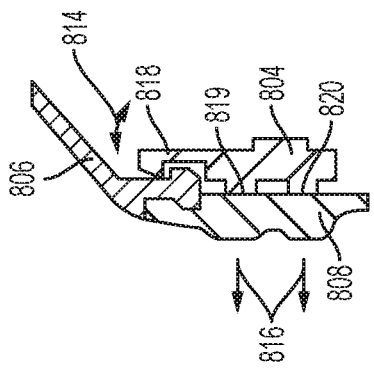
FIG. 54 illustrates a detail section view of the expanding plunger seal assembly in compression set inside the syringe, according to one aspect of the present disclosure.

FIG. 54 illustrates a detail section view of the expanding plunger seal assembly 800 in compression set inside the syringe 812, according to one aspect of the present disclosure. The section view shows the engagement ring 804 snap fit into the plunger cap 806 in the direction shown by the arrow 814 and the plunger seal 808 expanding in the direction shown by the arrows 816. The plunger seal 808 expands about 0.7 mm per side. Ramps 818, 820 move up behind the plunger seal 808 to expand the plunger seal 808 outwardly in the direction shown by the arrows 816.

Figure 56:
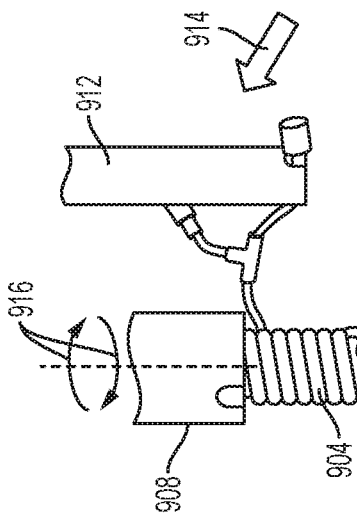
FIGS. 55-58 illustrate a sequence of steps for producing a coiled flexible tube sub-assembly, according to one aspect of the present disclosure, where.
Figure 58:
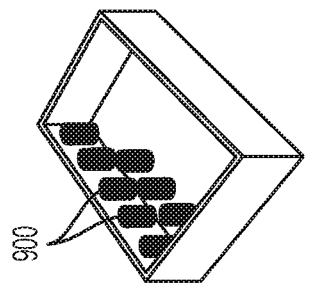
Figure 55:
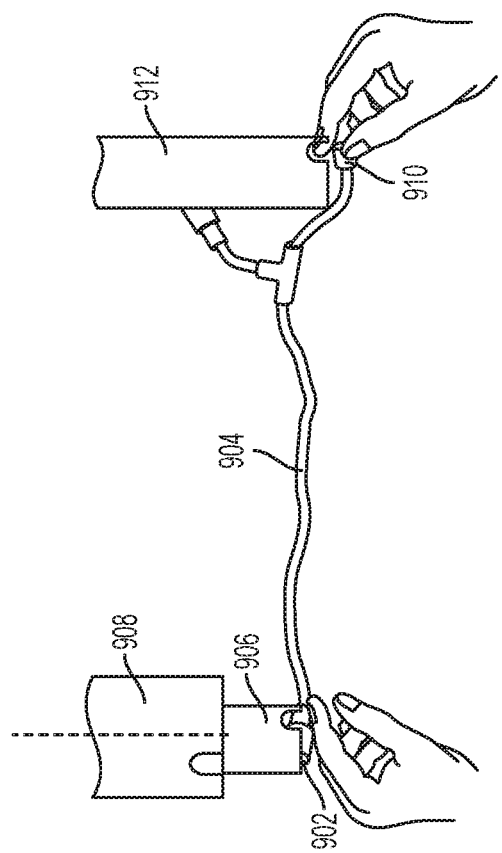
Figure 57:
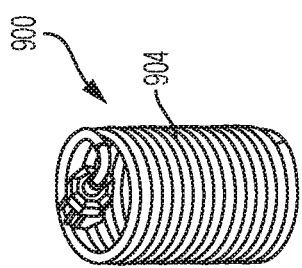

FIGS. 55-58 illustrate a sequence of steps for producing a flexible tube sub-assembly 900, according to one aspect of the present disclosure. As shown in FIG. 55, one end 902 of a flexible tube 904 is attached to a collar 906 (bobbin or cruciform) held in a mandrel 908. Another end 910 of the flexible tube 904 is attached to a moving arm 912. FIG. 56 illustrates the procedure of winding the flexible tube 904 about the collar 906 held in the mandrel 908, according to aspect of the present disclosure. The moving arm 912 moves in the direction indicated by the arrow 914 while the mandrel 908 rotates in the direction indicated by the arrows 916. FIG. 57 illustrates a flexible tube sub-assembly 900 wound about the collar 906, according to one aspect of the present disclosure. FIG. 58 illustrates a plurality of wound flexible tube sub-assemblies 900 ready for final assembly in a base cap, according to one aspect of the present disclosure.

FIGS. 59-62 illustrate a process of assembling a wound flexible tube into a chamber 918 defined by a base cap 920, according to one aspect of the present disclosure. FIG. 59 Illustrates insertion of a flexible tube sub-assembly 900 inside a chamber 918 (retaining feature) defined in the base cap 920 by a machine tool holder 922 (e.g., gripper, chuck), according to one aspect of the present disclosure. FIG. 60 illustrates the flexible tube sub-assembly 900 fully inserted into the chamber 924 defined by the base cap 920, according to one aspect of the present disclosure. FIG. 61 illustrates extraction of the collar 906 from the flexible tube sub-assembly 900 while the machine tool holder 922 pushes against the wound flexible tube 904, according to one aspect of the present disclosure. FIG. 62 illustrates the wound flexible tube 904 fully assembled inside the chamber 924 without the collar 906, according to one aspect of the present disclosure.

FIGS. 63-64 illustrate a process of assembling a flexible tube sub-assembly 900 in a base cap, according to one aspect of the present disclosure. FIG. 63 Illustrates insertion of a flexible tube sub-assembly 900 into a base cap 926 comprising a boss 928 feature by a machine tool holder 922 (e.g., gripper, chuck), according to one aspect of the present disclosure. FIG. 64 illustrates the flexible tube sub-assembly 900 fully inserted inside the base cap 926, according to one aspect of the present disclosure. FIG. 65 illustrates the flexible tube sub-assembly 900 inserted inside the base cap and the machine collar 906 retracted from the base cap 926, according to one aspect of the present disclosure.

Figure 66:
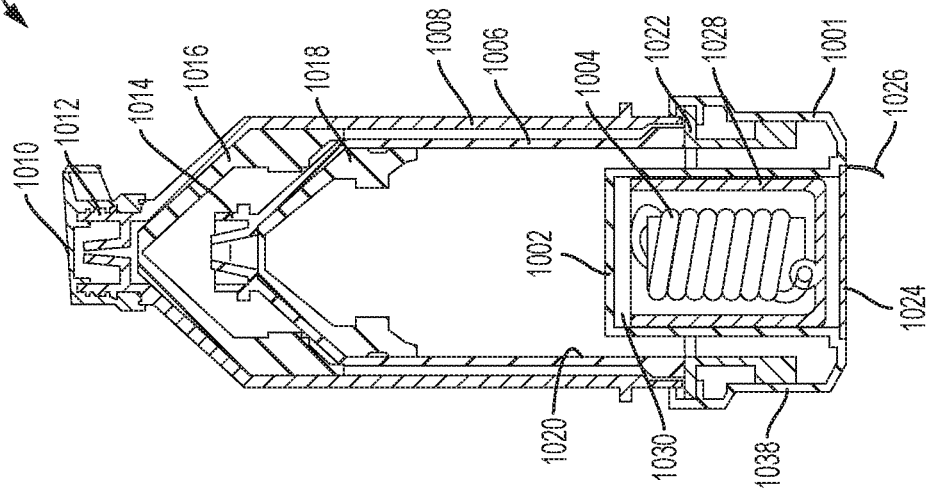
FIG. 66 is a section view of another configuration of a nested syringe assembly comprising a removable base cap containing ready to use sterile components, according to one aspect of the present disclosure.

FIG. 66 is a section view of another configuration of a nested syringe 1000 assembly comprising a removable base cap 1001 containing ready to use sterile components 1004, according to one aspect of the present disclosure. The nested syringe 1000 comprises an inner syringe 1006 and an outer syringe 1008. The inner syringe 1006 is nested within the outer syringe 1008 via connection to the outer plunger seal assembly 1016. A tip cap 1010 is threadably connected to a tip 1012 of the outer syringe 1008. The inner syringe 1006 also comprises a tip 1014. The tip 1014 of the inner syringe 1006 may comprise a threaded luer fitting or other device to secure the inner syringe 1006 within the outer syringe 1008. A plunger seal assembly 1016 is located within the outer syringe 1008 and another plunger seal assembly 1018 is located within the inner syringe 1006. A drip flange 1022 is provided about the outer surface of the inner syringe 1006. The drip flange 1022 extends radially outwardly from the outer surface of the inner syringe 1006.

The removable base cap 1001 is inserted at the proximal end of the inner syringe 1006. The removable base cap 1001 is frictionally fitted to an outer wall 1038 of the inner syringe 1006. The removable base cap 1001 isolates the sterile components 1004 from the inner wall surface interior surface 1020 of the inner syringe 1006. This may serve to protect the inner surface 1020 from scratching during shipping, for example. A chamber 1002 is defined by the removable base cap 1001. The chamber defines a space 1030 suitable to receive the sterile components 1004 contained within a container or chamber 1028. The sterile components 1004 may comprise a tube assembly, for example. The removable base cap 1001 is sealed with a peel off label 1024 to maintain the components 1004 located within the removable base cap 1001 sterile until they are ready to use. A tab 1026 may be provided to facilitate removal of the peel off label 1024.

Figure 67:
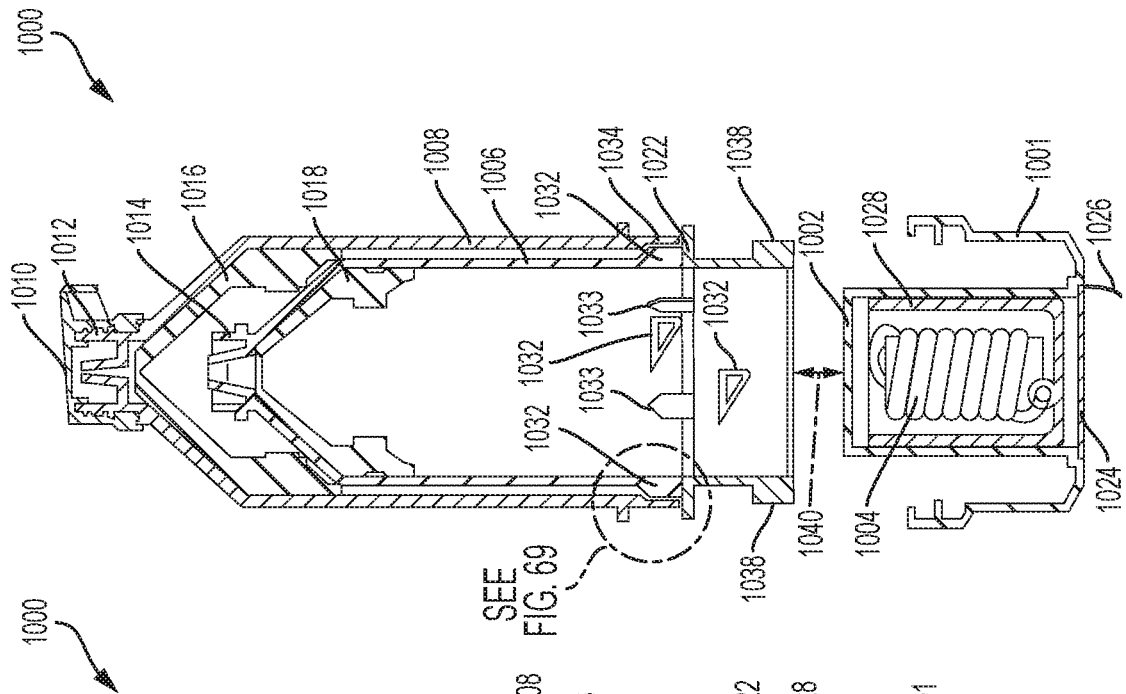
FIG. 67 is a section view of the nested syringe assembly shown in FIG. 66 with the removable base cap removed, according to one aspect of the present disclosure.

FIG. 67 is a section view of the nested syringe assembly 1000 shown in FIG. 66 with the removable base cap 1001 removed, according to one aspect of the present disclosure. Accordingly, the removable base cap 1001 can be slidably inserted and removed as shown by the arrow 1040. As previously discussed, the removable base cap 1001 is frictionally engaged with the outer wall 1038 portion of the inner syringe 1006, for example. Also shown in FIG. 67, lugs 1032, 1033 are provided on outer surface of the inner syringe 1006. The lugs 1032, 1033 engage corresponding engagement features 1034 provided on an inner surface of the outer syringe 1008. The engagement features 1034 of the outer syringe 1008 engage the lugs 1032, 1033 (teeth or key) of the inner syringe 1006 to transmit torque from the outer syringe 1008 to the inner syringe 1006. This functionality is further explained in connection with FIGS. 70-75, which illustrate a sequence of steps for loading and unloading the nested syringe assembly to an injector.

Figure 68:
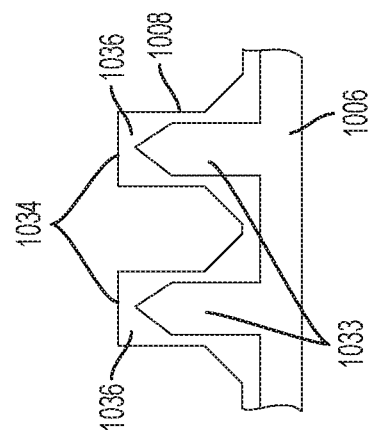
FIG. 68 is detail view of a torque engagement feature with mounting lugs keyed to engagement features to transmit torque from the outer syringe to the inner syringe, according to one aspect of the present disclosure.
Figure 69:
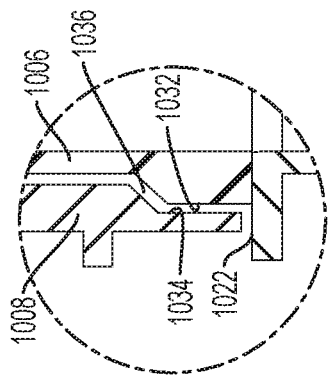
FIG. 69 is another detail view of the torque engagement feature shown in FIG. 68, according to one aspect of the present disclosure.

FIG. 68 is detail view of a torque engagement feature with lugs 1033 keyed to engagement features 1034 to transmit torque from the outer syringe 1008 to the inner syringe 1006, according to one aspect of the present disclosure. FIG. 69 is another detail view of the torque engagement feature shown in FIG. 68, according to one aspect of the present disclosure. The lugs 1033 on the inner syringe 1006 are keyed to the engagement features 1034 on the outer syringe via a space 1036 defined by the outer syringe 1008.

Figure 70:
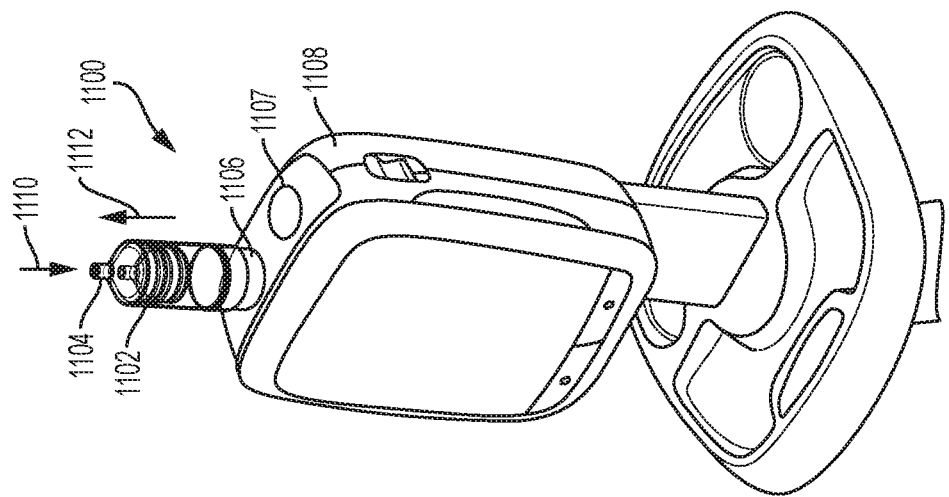

FIGS. 70-75 illustrate a sequence of steps for loading and unloading a nested syringe assembly 1100 to an injector 1108, according to one aspect of the present disclosure, where:

FIG. 70 illustrates a first step in the loading sequence where the inner syringe 1102 of the nested syringe assembly 1100 is engaged with a locking mechanism through a first port 1106 of the fluid injector 1108 to releasably lock the inner syringe 1102 with the fluid injector 1108 into self-orienting alignment with the locking mechanism, according to one aspect of the present disclosure. The inner syringe 1102 is nested within an outer syringe 1104. The nested syringe assembly 1100 is inserted into the first port 1106 of the injector 1108 by applying an insertion force 1110 towards the injector 1108 to engage the inner syringe 1004 with the fluid injector 1108 into self-orienting alignment with the locking mechanism of the fluid injector 1108. The configuration of lugs provided on the inner syringe 1102 enables the inner syringe 1102 to be loaded into the first port 1106 with no or little applied torque. This is made possible by a spring loaded plate within the first port 1106 that rotates when it engages the lugs of the inner syringe 1102. Once the inner syringe 1102 is locked into the locking mechanism of the fluid injector 1108, the outer syringe 1104 is removed from the nested configuration by applying a force 1112 in the direction away from the injector 1108.

Figure 71:
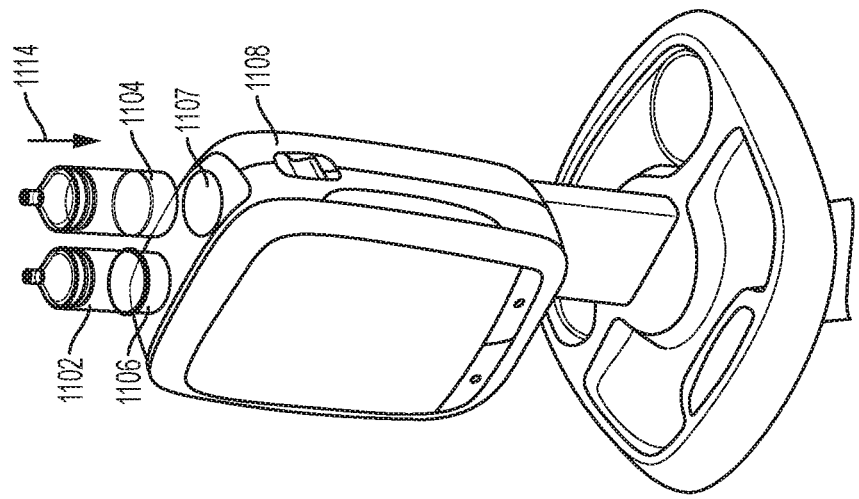
FIGS. 70-75 illustrate a sequence of steps for loading and unloading a nested syringe assembly to an injector, according to one aspect of the present disclosure, where.
Figure 72:
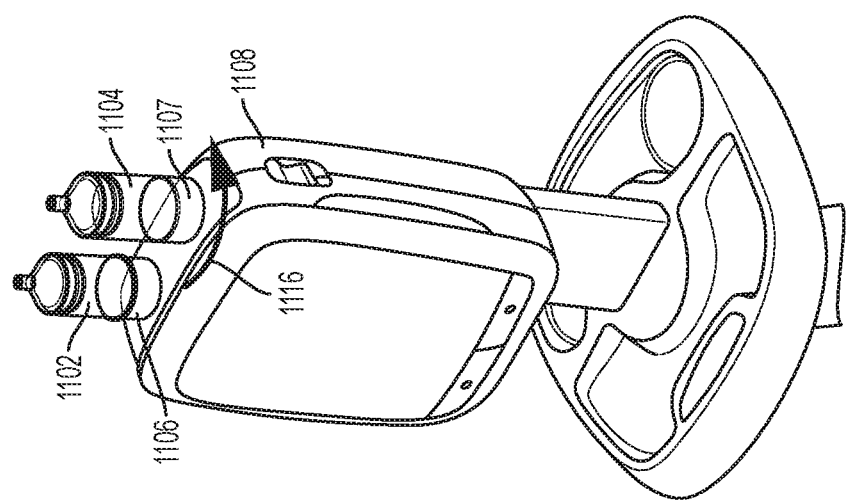

FIG. 71 illustrates a second step in the loading sequence where the outer syringe 1104 of the nested syringe assembly 1100 is engaged with a locking mechanism through a second port 1107 of the fluid injector 1108 to releasably lock the outer syringe 1104 with the fluid injector 1108 into self-orienting alignment with the locking mechanism, according to one aspect of the present disclosure. The outer syringe 1104 is inserted in the second port 1107 by applying an insertion force 1114 towards the injector 1108. As discussed in connection with FIG. 70, the configuration of lugs provided on the outer syringe 1104 enables the outer syringe 1104 to be loaded into the second port 1107 with no or little applied torque. This is made possible by a spring loaded plate within the second port 1107 that rotates when it engages the lugs of the outer syringe 1104. Once the outer syringe 1104 is loaded into FIG. 72 illustrates a first step in the unloading sequence where the outer syringe 1104 is subjected to a counterclockwise torque 1116 to unlock the outer syringe 1104 from the locking mechanism of the injector 1108, according to one aspect of the present disclosure.

Figure 73:
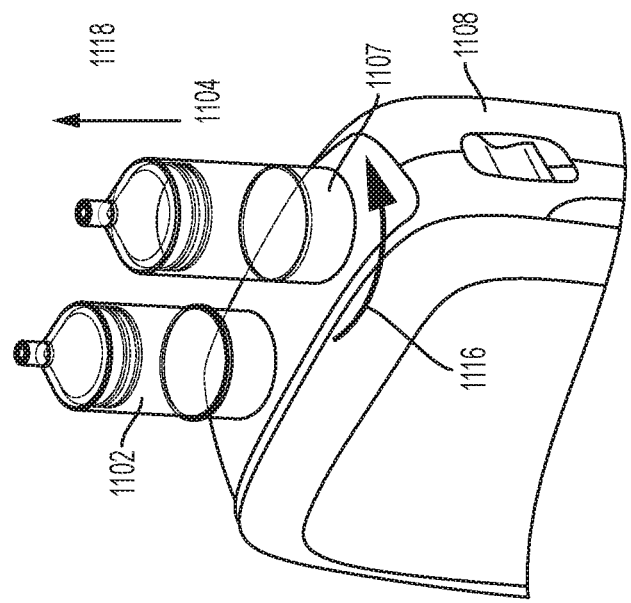

FIG. 73 illustrates a second step in the unloading sequence where the outer syringe 1104 is removed from the injector 1108, according to one aspect of the present disclosure. After unlocking the outer syringe 1104 from the locking mechanism of the injector 1108 by applying a counterclockwise torque 1116 to the outer syringe 1104, a force 1118 is applied to the outer syringe 1104 in a direction away from the injector 1108 to unload the outer syringe 1104 from the second port 1107 of the injector 1108.

Figure 74:
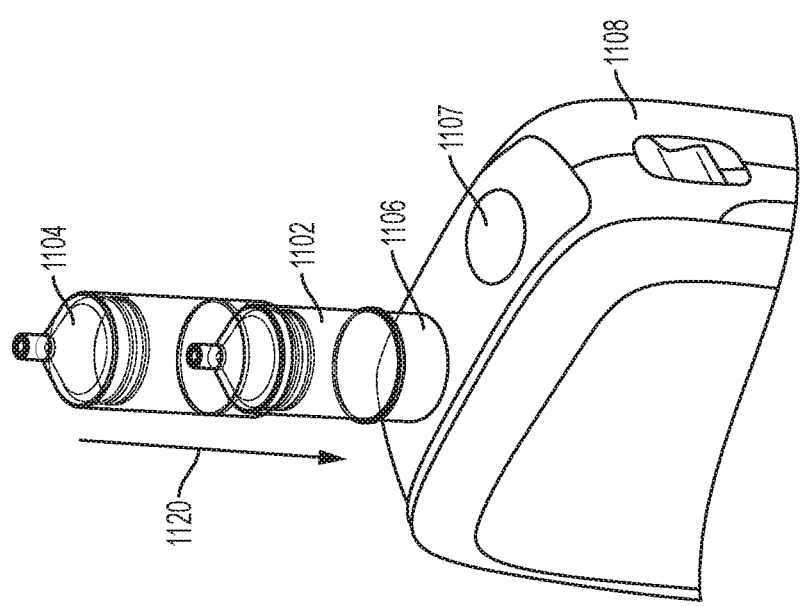

FIG. 74 is illustrates a third step in the unloading sequence where the outer syringe 1104 is located over the inner syringe 1102, according to one aspect of the present disclosure. At this stage of the unloading sequence, reference is made to FIGS. 68 and 69 to illustrate the lugs 1032, 1033 and the engagement features 1034 that are provided on inner and outer syringes 1102, 1104 (but not shown for clarity of disclosure). The lugs 1032, 1033 and the engagement features 1034 are keyed or meshed as the outer syringe 1104 is located over the inner syringe 1102 by applying a force 1120 to the outer syringe 1104 in a direction towards the injector 1108.

Figure 75:
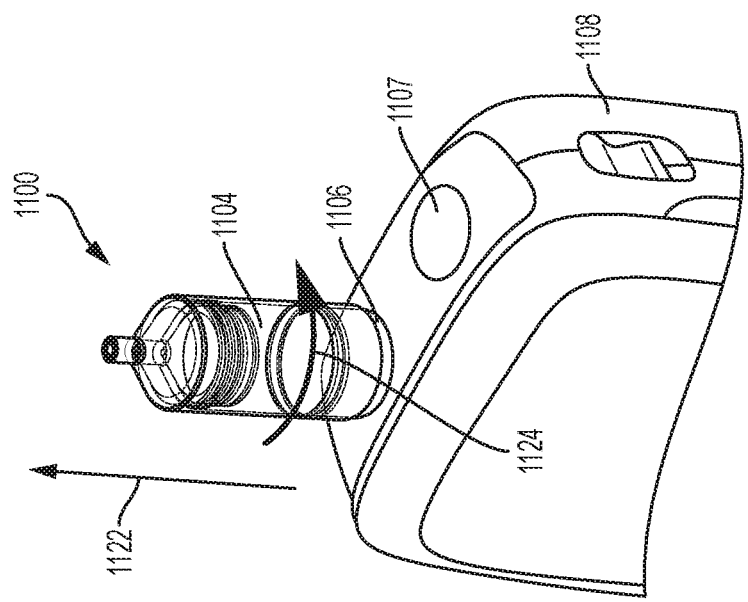

FIG. 75 illustrates a fourth step in the unloading sequence where the outer syringe 1104 is rotated into locking engagement with the inner syringe 1102 such that torque applied top the outer syringe 1104 is transmitted to the inner syringe 1102 to unlock the nested syringe assembly 1100 from the locking mechanism of the injector 1108, according to one aspect of the present disclosure. As described in connection with FIGS. 68, 69, and 74, once the lugs 1032, 1033 and engagement features 1034 are keyed, a counterclockwise torque 1124 applied to the outer syringe 1104 is transmitted to the inner syringe 1102, which is now locked to the outer syringe 1104. Once the counterclockwise torque 1124 is applied to the nested syringe assembly 1100, it can be removed by applying a force 1122 to the nested syringe assembly 1100 in a direction away from the injector 1108 to fully unload the injector 1108.

Figure 76:
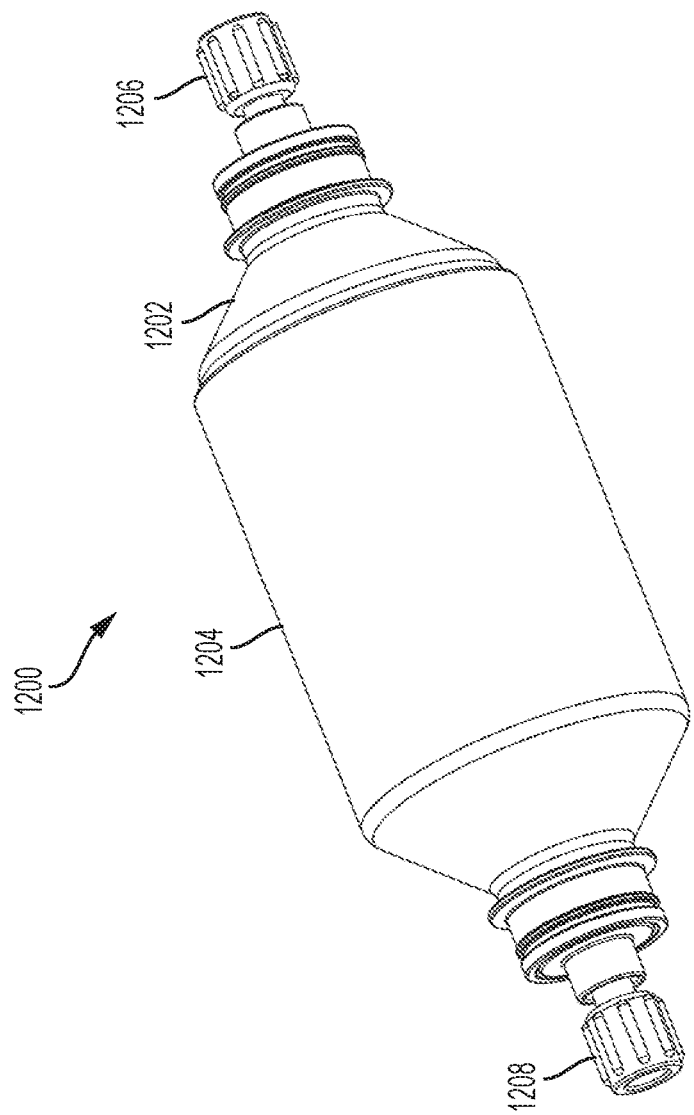
FIG. 76 is a nested syringe assembly comprising an inner syringe nested within an outer syringe, according to one aspect of the present disclosure.

FIG. 76 is a nested syringe assembly 1200 comprising an inner syringe 1202 nested within an outer syringe 1204, according to one aspect of the present disclosure. The inner syringe 1202 and outer syringe 1204 may be a rolling diaphragm syringe in a rolled, compressed configuration as described in International PCT Application No. PCT/US2012/027582, the disclosure of which is incorporated by this reference. Each of the inner and outer syringes 1202, 1204 comprises a tip 1206, 1208. The inner syringe 1202 is slidably inserted into the bore of the outer syringe 1204 and disposed within the bore of the outer syringe 1204 for storage and shipment. In the configuration shown in FIGS. 76-79, the inner and outer syringes 1202, 1204 are oriented such that the tips 1206, 1208 are exposed and point in opposite directions.

Figure 77:
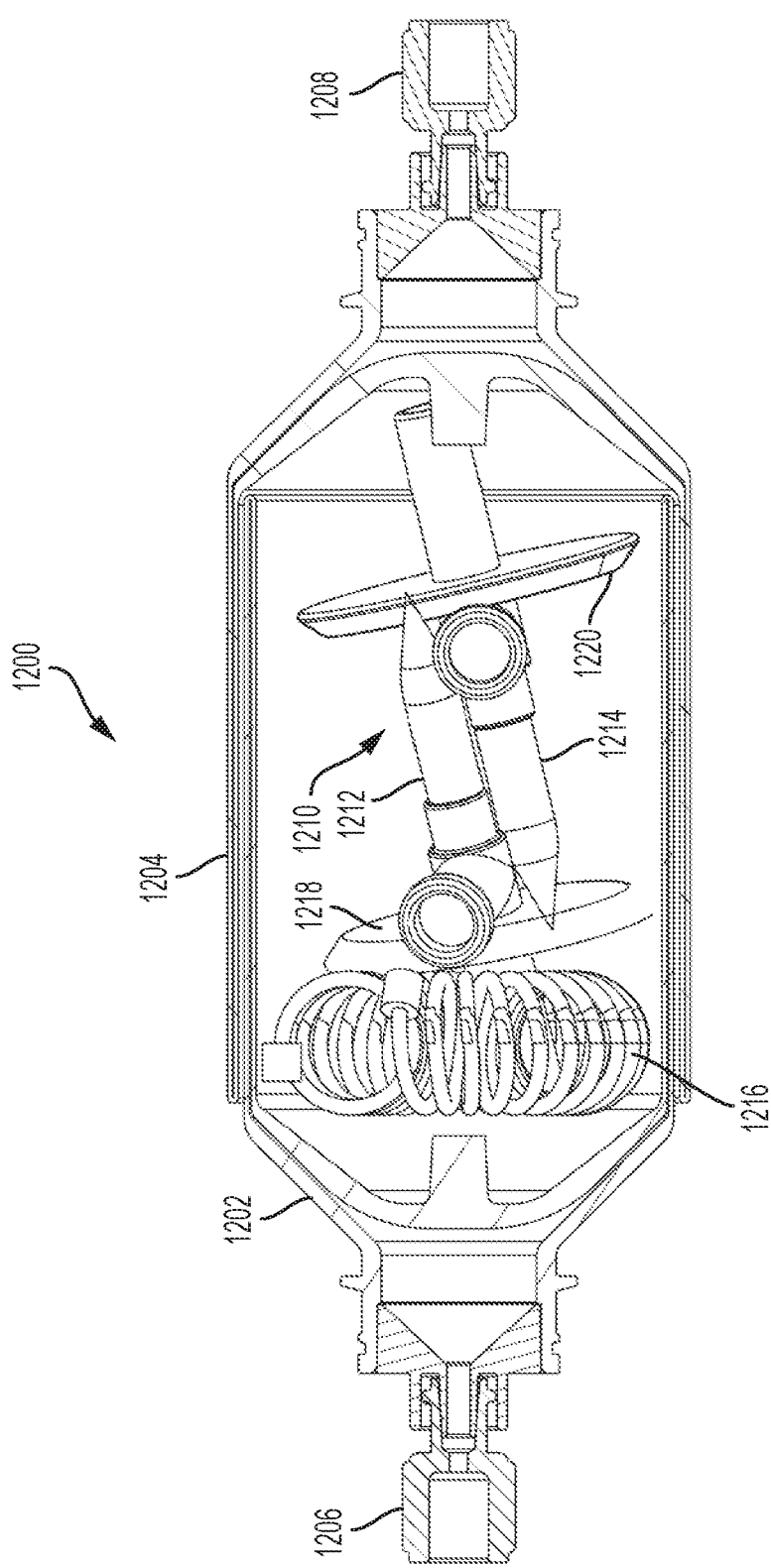
FIG. 77 is a sectional view of the nested syringe assembly shown in FIG. 76, according to one aspect of the present disclosure.
Figure 78:
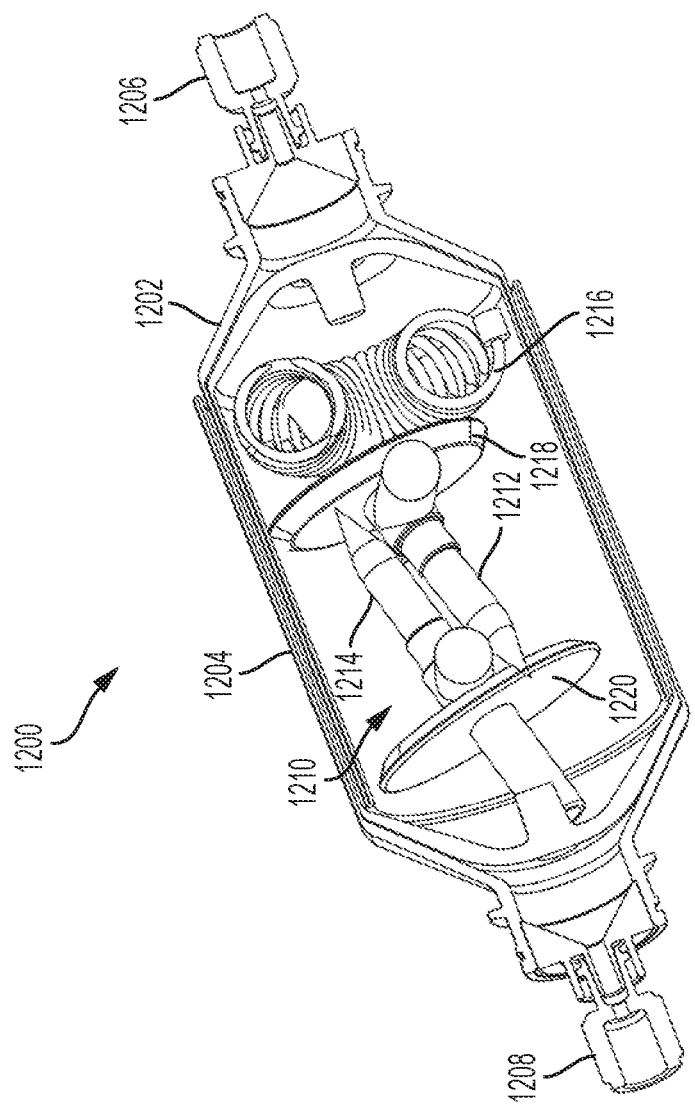
FIG. 78 is a perspective sectional view of the nested syringe assembly shown in FIG. 76, according to one aspect of the present disclosure.
Figure 79:
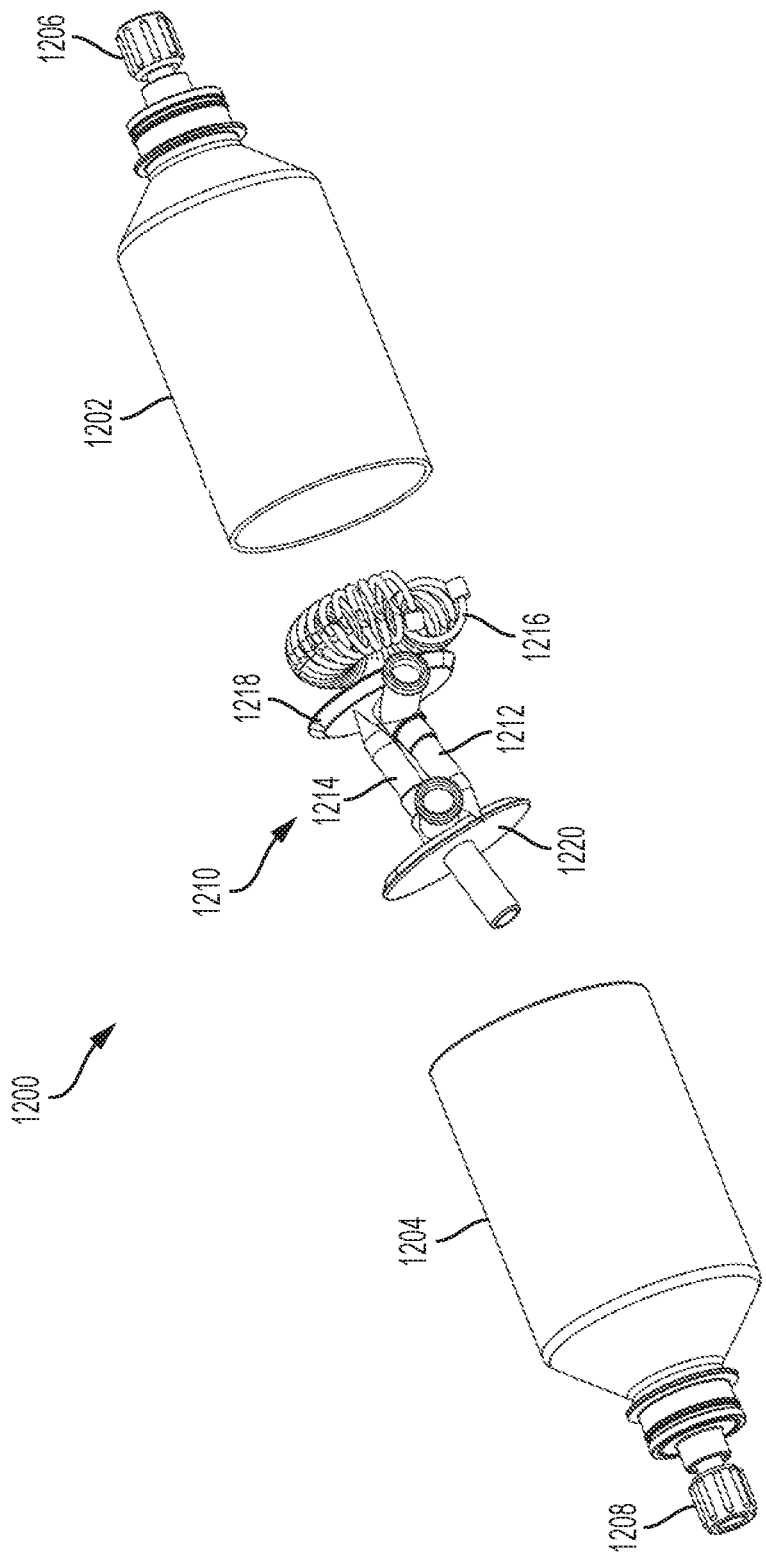
FIG. 79 is an exploded view of the nested syringe assembly shown in FIG. 76, according to one aspect of the present disclosure.

With reference now to FIGS. 77-79, the nested syringe assembly 1200 comprises a fluid connector assembly 1210 positioned within the bore of the inner syringe 1202. The fluid connector assembly 1210 comprises first and second spikes 1212, 1214 suitable for piercing a cap of a fluid bottle and a flexible tube 1216. Each of the first and second spikes 1212, 1214 includes a flange 1218, 1220. The nested syringe assembly 1200 may further include a prime tube (flexible tube with a filter on the end) (not shown) for use when priming the syringe and tubing prior to an injection procedure. In other aspects, the fluid connector assembly 1210 may be sealed is a sterile pouch or flexible container prior to insertion into the nested syringe assembly. For example, in a nested configuration of a pair of rolling diaphragm syringes, the fluid connector assembly 1210 located in an interior portion that need not be sterile as it will not be exposed to any medical fluid, in which case the sterile pouch or flexible container maintains the sterility of the components of fluid connector assembly 1210.

Figure 80:
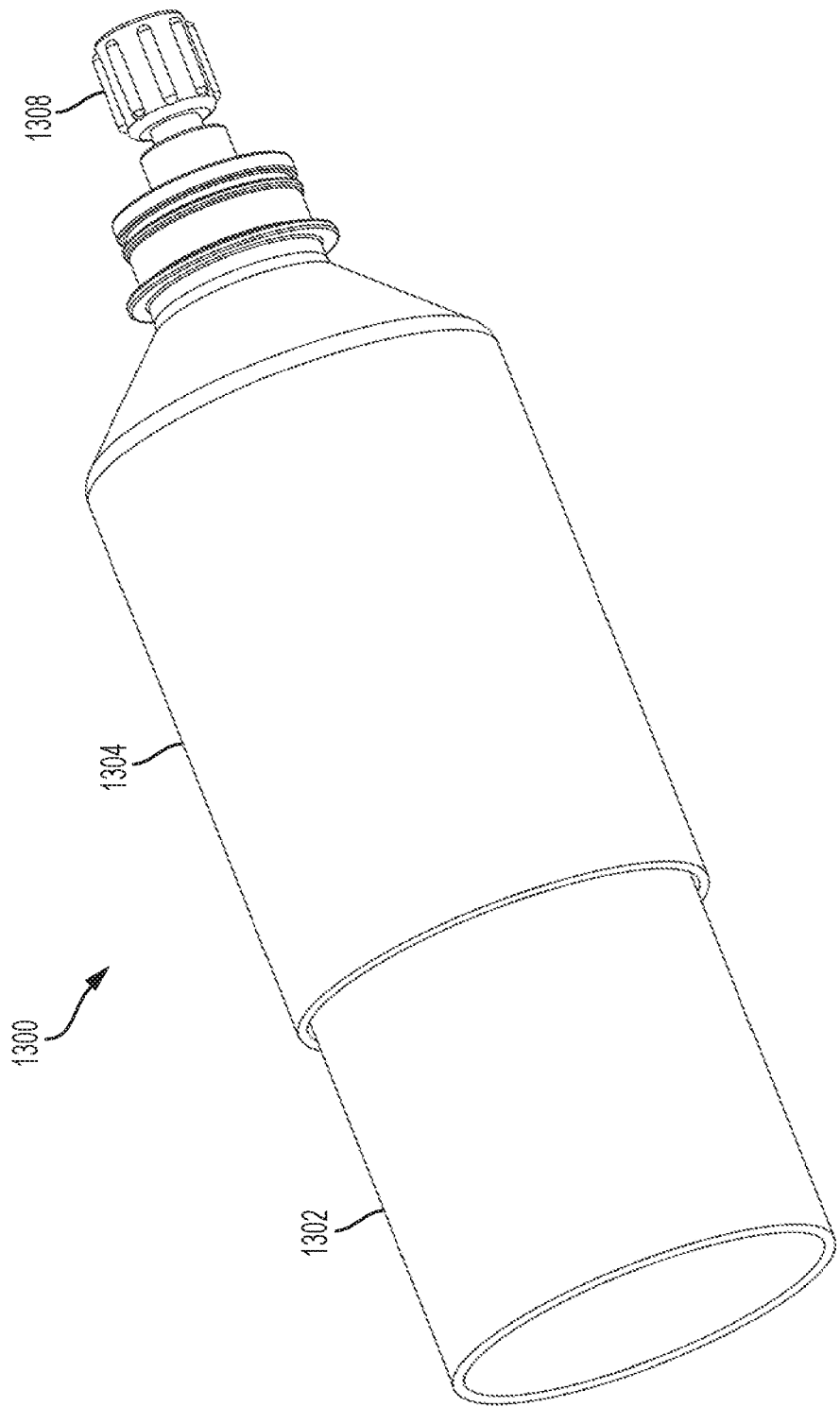
FIG. 80 is a nested syringe assembly comprising an inner syringe nested within an outer syringe, according to one aspect of the present disclosure.

FIG. 80 is a nested syringe assembly 1300 comprising an inner syringe 1302 nested within an outer syringe 1304, according to one aspect of the present disclosure. Each of the inner and outer syringes 1302, 1304 comprises a tip 1306 (not shown in FIG. 80, shown in FIGS. 81-83), 1308. The inner syringe 1302 is slidably inserted into the bore of the outer syringe 1304 and disposed within the bore of the outer syringe 1304 for storage and shipment. In the configuration shown in FIGS. 80-83, the inner and outer syringes 1302, 1304 are oriented such that the tip 1306 of the inner syringe 1302 is disposed within a cavity defined in the outer syringe 1304 and the tip of the outer syringe 1304 is exposed and points in the same direction as the tip 1306 of the inner syringe 1302.

Figure 81:
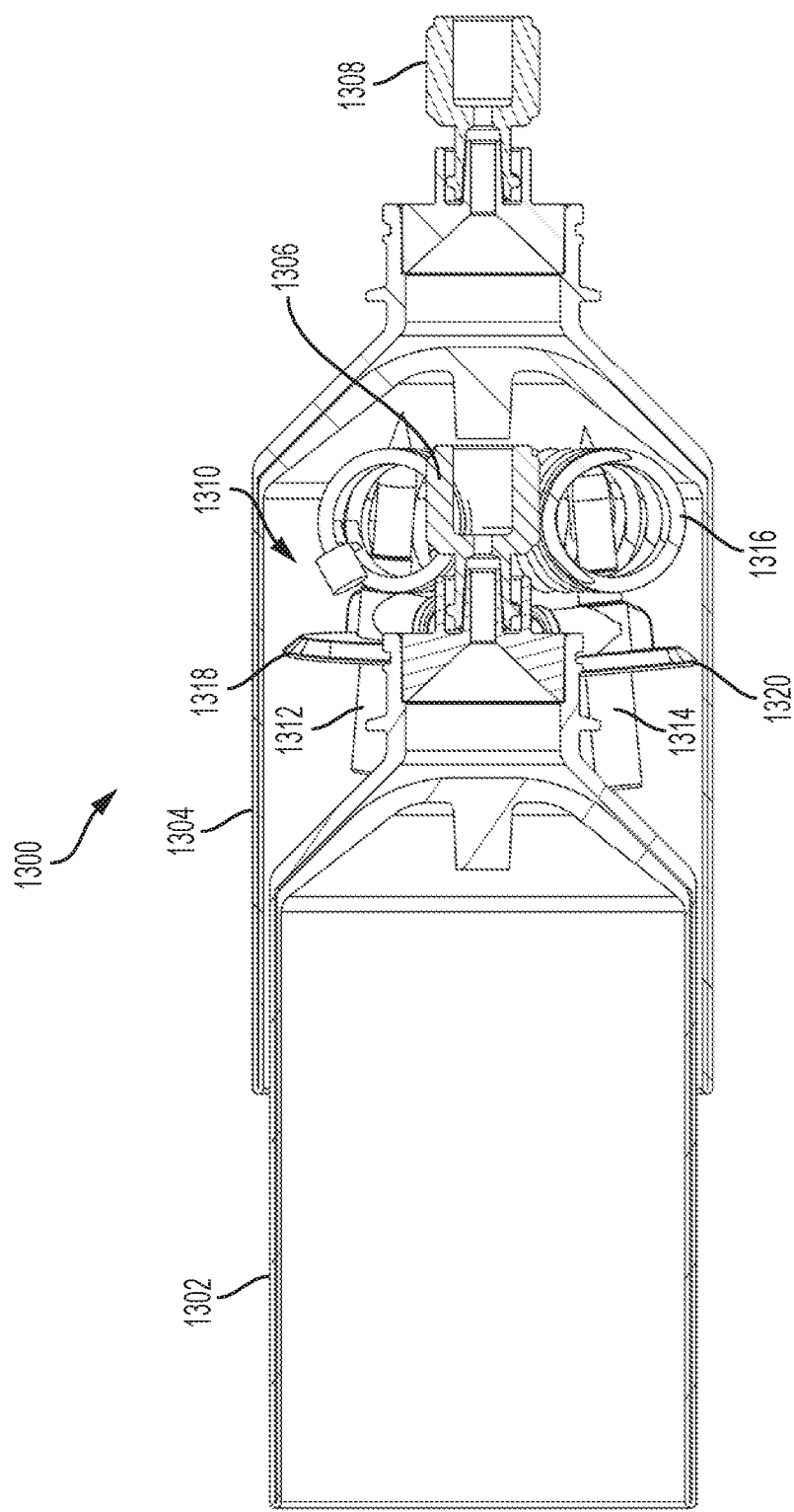
FIG. 81 is a section view of the nested syringe assembly shown in FIG. 80, according to one aspect of the present disclosure.
Figure 82:
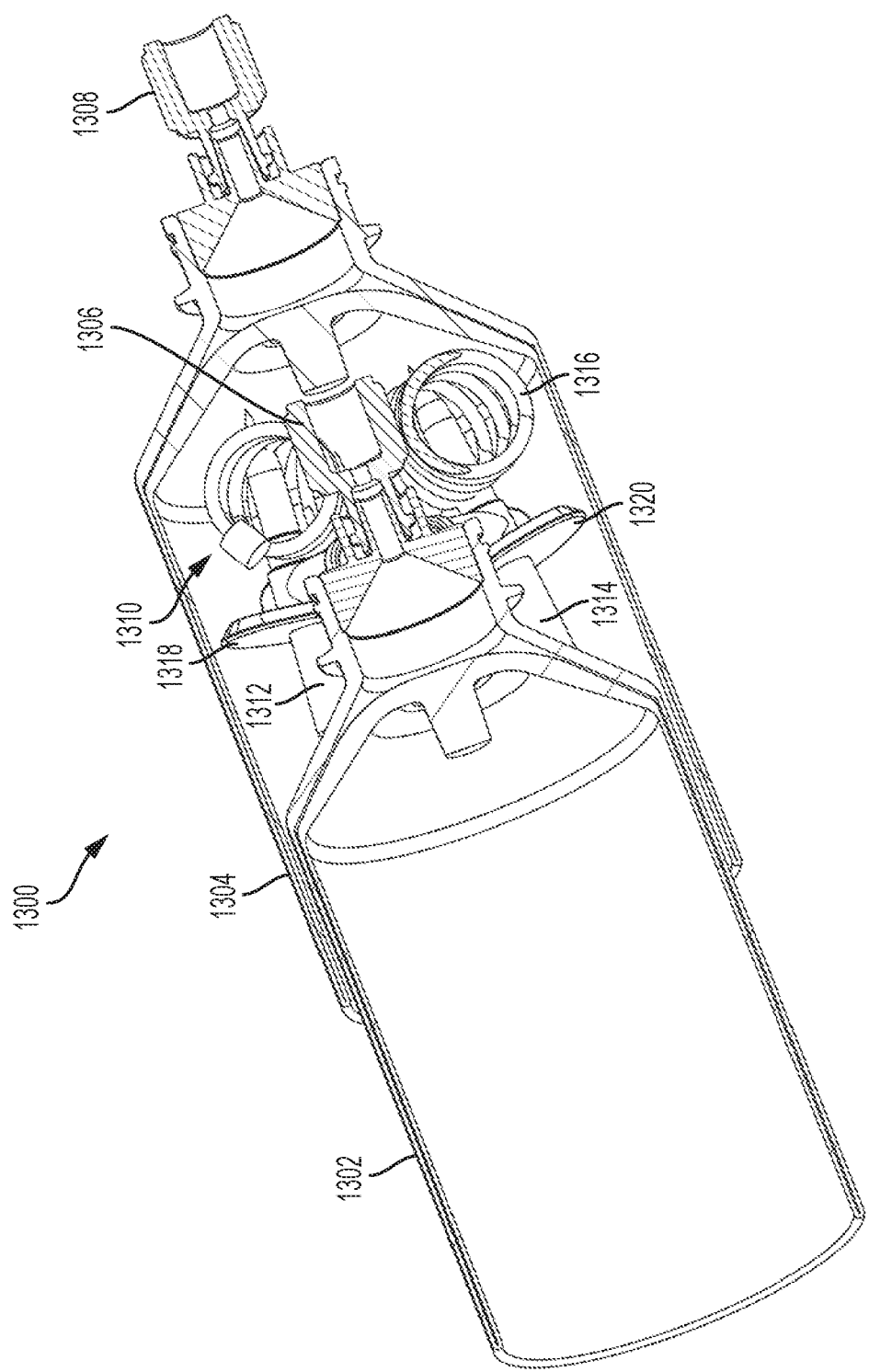
FIG. 82 is a perspective sectional view of the nested syringe assembly shown in FIG. 80, according to one aspect of the present disclosure.
Figure 83:
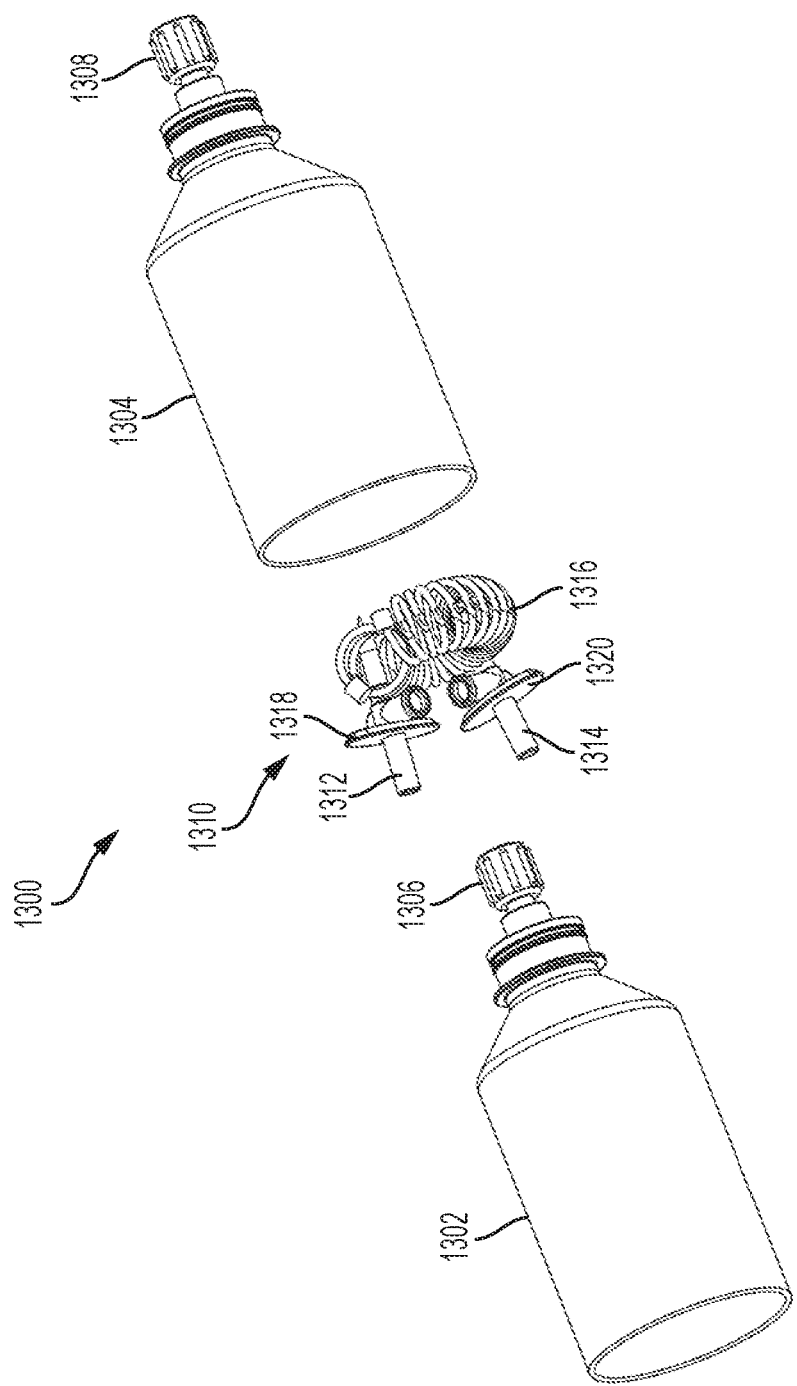
FIG. 83 is an exploded view of the nested syringe assembly shown in FIG. 80, according to one aspect of the present disclosure.

With reference now to FIGS. 81-83, the nested syringe assembly 1300 comprises a fluid connector assembly 1310 positioned within the bore of the outer syringe 1304. The fluid connector assembly 1310 comprises first and second spikes 1312, 1314 suitable for piercing a cap of a fluid bottle and a flexible tube 1316. Each of the first and second spikes 1312, 1314 includes a flange 1318, 1320. In other aspects, the fluid connector assembly 1310 may be sealed is a sterile pouch or flexible container prior to insertion into the nested syringe assembly. For example, in a nested configuration of a pair of rolling diaphragm syringes, the fluid connector assembly 1310 located in an interior portion that need not be sterile as it will not be exposed to any medical fluid, in which case the sterile pouch or flexible container maintains the sterility of the components of fluid connector assembly 1310.

Figure 84:
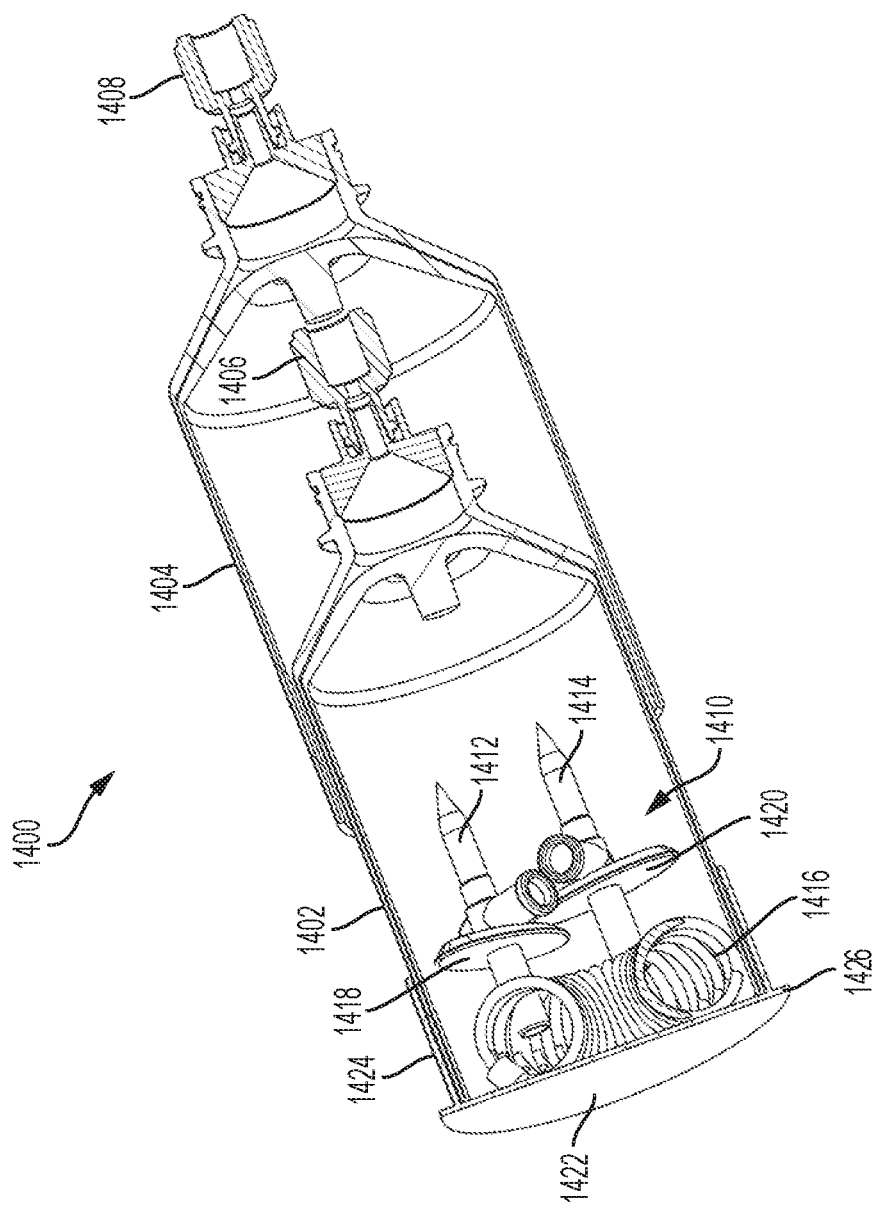
FIG. 84 is a section view of a nested syringe assembly, according to one aspect of the present disclosure.
Figure 85:
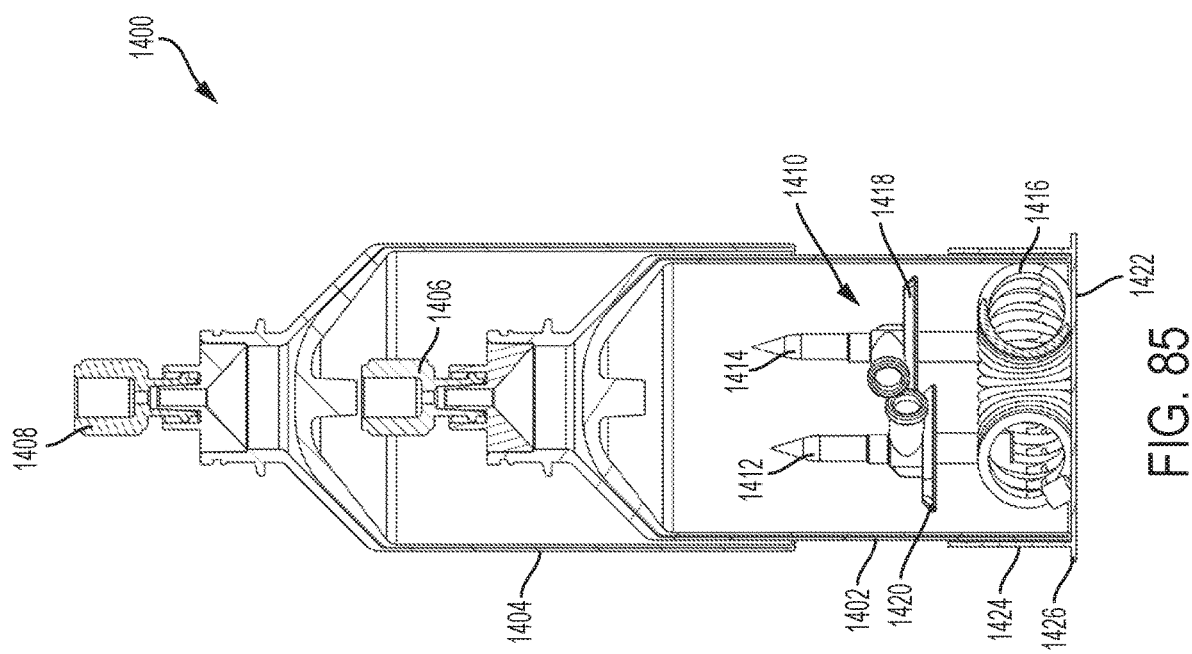
FIG. 85 is another section view of the nested syringe assembly shown in FIG. 84, according to one aspect of the present disclosure.
Figure 86:
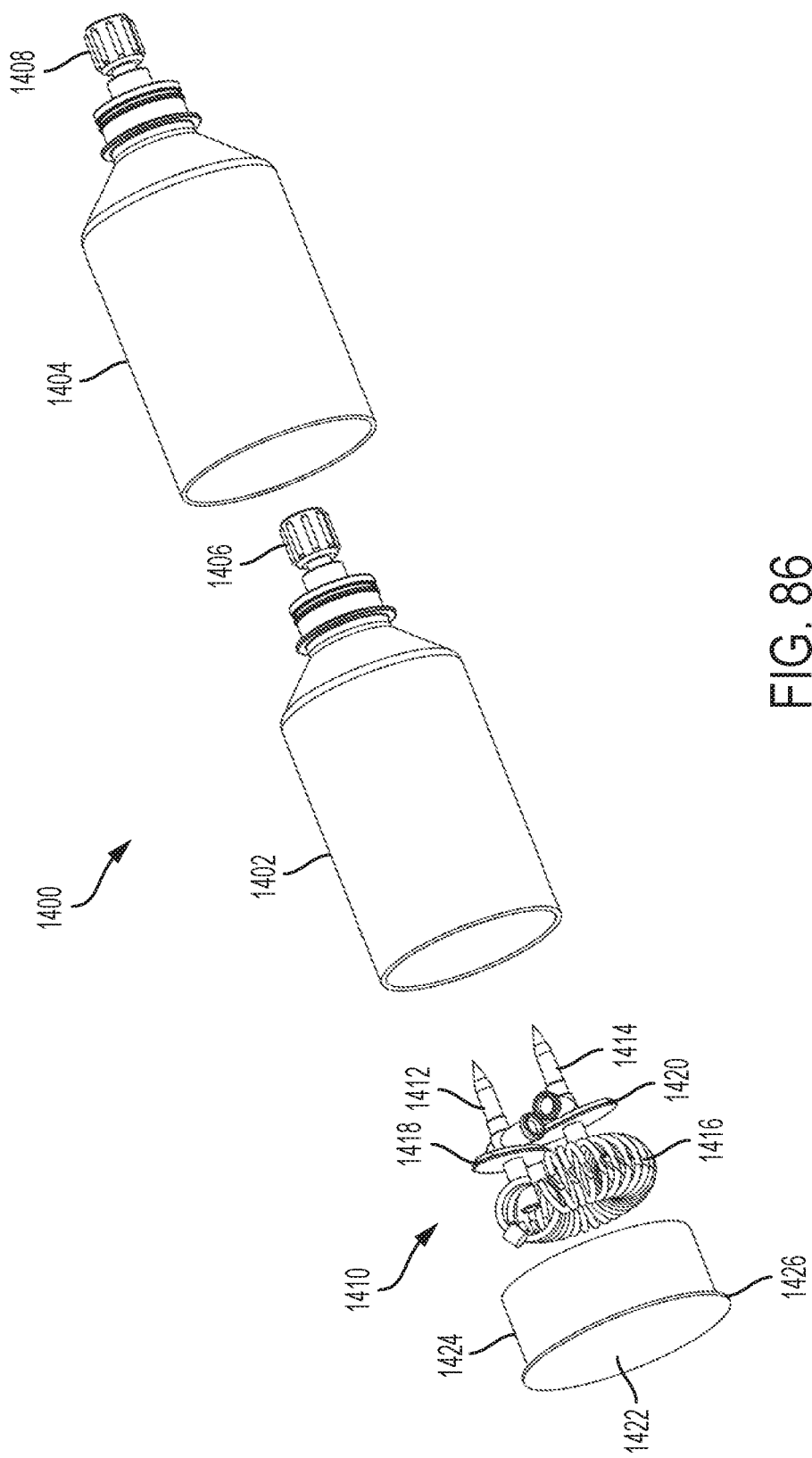
FIG. 86 is an exploded view of the nested syringe assembly shown in FIG. 84, according to one aspect of the present disclosure.

Turning now to FIGS. 84-86, there is shown a nested syringe assembly 1400 comprising an inner syringe 1402 nested within an outer syringe 1404, according to one aspect of the present disclosure. Each of the inner and outer syringes 1402, 1404 comprises a tip 1406, 1408. The inner syringe 1402 is slidably inserted into the bore of the outer syringe 1404 and disposed within the bore of the outer syringe 1404 for shipment and storage. In the configuration shown in FIGS. 84-86, the inner and outer syringes 1402, 1404 are oriented such that the tip 1406 of the inner syringe 1402 is disposed within a cavity defined in the outer syringe 1404 and the tip of the outer syringe 1404 is exposed and points in the same direction as the tip 1406 of the inner syringe 1402. In other aspects, the fluid connector assembly 1410 may be sealed is a sterile pouch or flexible container prior to insertion into the nested syringe assembly. For example, in a nested configuration of a pair of rolling diaphragm syringes, the fluid connector assembly 1410 located in an interior portion that need not be sterile as it will not be exposed to any medical fluid, in which case the sterile pouch or flexible container maintains the sterility of the components of fluid connector assembly 1410.

Still with reference now to FIGS. 84-86, the nested syringe assembly 1400 comprises a fluid connector assembly 1410 positioned within the bore of the inner syringe 1402. The fluid connector assembly 1410 comprises first and second spikes 1412, 1414 suitable for piercing a cap of a fluid bottle and a flexible tube 1416. Each of the first and second spikes 1412, 1414 includes a flange 1418, 1420. An end cap 1422 comprises a sidewall 1424 that is slidably disposed over the outer wall of the inner syringe 1402. The end cap 1422 functions to contain the fluid connector assembly 1410 within the inner bore of the inner syringe 1402. The end cap 1422 comprises a flange 1426 that a diameter that is greater than the diameter of the inner syringe 1402 and/or greater than the diameter of the outer syringe 1404. The flange 1426 enables the nested syringe assembly 1400 to be set upright on a flat surface such that the first and second syringes 1402, 1404 can be removed from the end cap 1422 leaving the fluid connector assembly 1410 in the end cap 1422.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

We claim:

1. A nested syringe assembly, comprising:
   a first syringe comprising a cylindrical body defining an inner diameter, a conical portion at a distal end, and an injector interface at a proximal end for installing the first syringe in a first port of a fluid injector;
   a second syringe comprising a cylindrical body defining an outer diameter, a conical portion at a distal end, and an injector interface at a proximal end for installing the second syringe in a second port of the fluid injector; and
   a flexible tube assembly disposed within a bore of the second syringe,
   wherein the outer diameter of the second syringe is less than the inner diameter of the first syringe, and wherein at least a portion of the cylindrical body of the second syringe is disposed within the cylindrical body of the first syringe.

2. The nested syringe assembly of claim 1, further comprising:
   a first plunger seal assembly positioned within the cylindrical body of the first syringe; and
   a second plunger seal assembly positioned within the cylindrical body of the second syringe.

3. The nested syringe assembly of claim 2, wherein the first plunger seal assembly positioned within the cylindrical body of the first syringe comprises:
   a seal ring;
   a snap ring positioned within the seal ring; and
   an engagement ring positioned within the seal ring.

4. The nested syringe assembly of claim 3, further comprising at least one of a plunger engagement mechanism and a key element defined by the engagement ring.

5. The nested syringe assembly of claim 4, wherein the nested syringe assembly comprises the plunger engagement mechanism, wherein the plunger engagement mechanism is in snap fit engagement with the snap ring.

6. The nested syringe assembly of claim 3, further comprising at least one engagement member configured to reversibly engage a piston of the fluid injector.

7. The nested syringe assembly of claim 3, wherein the first plunger seal assembly or the second plunger seal assembly is compression set inside the first syringe or the second syringe, respectively.

8. The nested syringe assembly of claim 1, further comprising at least one engagement feature provided about the proximal end of the cylindrical body of one or both of the first syringe and the second syringe, wherein the at least one engagement feature is configured to reversibly couple the first syringe or the second syringe to one or both of the first port and the second port of the fluid injector.

9. The nested syringe assembly of claim 8, wherein the at least one engagement feature comprises a tapered surface configured to contact a guide in one or both of the first port and the second port of the fluid injector to self-orient the first syringe or the second syringe within the first port or the second port, when the first syringe or the second syringe is inserted into the first port or the second port, respectively.

10. A nested syringe assembly, comprising:
a first syringe comprising a cylindrical body defining an inner diameter, a conical portion at a distal end terminating in a first tip, and an injector interface at a proximal end for installing the first syringe in a first port of a fluid injector;
a second syringe comprising a cylindrical body defining an outer diameter, a conical portion at a distal end terminating in a second tip, and an injector interface at a proximal end for installing the second syringe in a second port of the fluid injector;
a base cap coupled to the proximal end of the cylindrical body of at least one of the first syringe and the second syringe, wherein at least a portion of the second syringe is disposed in the base cap;
a tip cap coupled to the first tip of the first syringe; and
at least one of a flexible tube assembly and a fluid connector assembly disposed within the base cap,
wherein the outer diameter of the second syringe is less than the inner diameter of the first syringe, and wherein at least a portion of the cylindrical body of the second syringe is disposed within the cylindrical body of the first syringe.

11. The nested syringe assembly of claim 10, wherein the first syringe is in a threaded engagement with the base cap.

12. The nested syringe assembly of claim 10, wherein the first syringe is in a threaded engagement or a snap fit engagement with the second syringe.

13. The nested syringe assembly of claim 10, wherein the second syringe is in a threaded engagement or a snap fit engagement with the base cap.

14. The nested syringe assembly of claim 10, further comprising an O-ring seal between at least one of the first syringe and the base cap and the second syringe and the base cap.

15. The nested syringe assembly of claim 10, wherein a diameter of the injector interface of the second syringe is the same as a diameter of the injector interface of the first syringe.

16. The nested syringe assembly of claim 10, wherein the first syringe and the second syringe are positioned relative to each other with the first tip and the second tip directed in a same direction or the first syringe and the second syringe are positioned relative to each other with the first tip and the second tip directed in an opposite direction.

17. A method of manufacturing a nested syringe assembly, the method comprising:
inserting a first plunger seal assembly within a cylindrical body of a first syringe;
inserting a second plunger seal assembly within a cylindrical body of a second syringe;
inserting at least one of a flexible tube assembly and a fluid connector assembly into a base cap;
inserting at least a proximal portion of the second syringe into the base cap and at least a distal portion of the second syringe within the cylindrical body of the first syringe;
coupling at least one of the first syringe and the second syringe to the base cap,
wherein the first syringe comprises the cylindrical body defining an inner diameter, a conical portion at a distal end, and an injector interface at a proximal end for installing the first syringe in a first port of a fluid injector, and
the second syringe comprises the cylindrical body defining an outer diameter, a conical portion at a distal end, and an injector interface at a proximal end for installing the second syringe in a second port of the fluid injector, and the outer diameter of the second syringe is less than the inner diameter of the first syringe.

18. The method of claim 17, comprising coupling a tip cap on a tip at the distal end of the first syringe.

* * * * *

UNITED STATES PATENT AND TRADEMARK OFFICE
CERTIFICATE OF CORRECTION

| | | |
|---|---|---|
| PATENT NO. | : 10,835,674 B2 | Page 1 of 1 |
| APPLICATION NO. | : 15/774037 | |
| DATED | : November 17, 2020 | |
| INVENTOR(S) | : Cowan et al. | |

It is certified that error appears in the above-identified patent and that said Letters Patent is hereby corrected as shown below:

In the Specification

In Column 4, Line 64, delete "to aspect" and insert -- to one aspect --, therefor.
In Column 6, Line 29, delete "to aspect" and insert -- to one aspect --, therefor.
In Column 6, Line 39, delete "to one aspect of the present disclosure, where:" and insert -- to one aspect of the present disclosure. --, therefor.
In Column 7, Line 44, delete "FIG. 74 is illustrates" and insert -- FIG. 74 illustrates --, therefor.
In Column 7, Line 49, delete "applied top the outer" and insert -- applied to the outer --, therefor.
In Column 13, Line 14, delete "arrow 194" and insert -- arrow 194, --, therefor.
In Column 15, Line 63, delete "fluid port coupling 267" and insert -- fluid port coupling 293 --, therefor.
In Column 16, Line 10, delete "fluid connector 275" and insert -- fluid connector assembly 275 --, therefor.
In Column 17, Line 29, delete "positioning the outer" and insert -- positioning of the outer --, therefor.
In Column 18, Line 33, delete "hermitic seal" and insert -- hermetic seal --, therefor.
In Column 20, Line 35, delete "positioning the outer" and insert -- positioning of the outer --, therefor.
In Column 21, Lines 50-51, delete "to aspect" and insert -- to one aspect --, therefor.
In Column 23, Lines 18-19, delete "according to one aspect of the present disclosure, where:" and insert -- according to one aspect of the present disclosure. --, therefor.
In Column 24, Line 5, delete "FIG. 74 is illustrates" and insert -- FIG. 74 illustrates --, therefor.
In Column 24, Lines 20-21, delete "applied top the outer" and insert -- applied to the outer --, therefor.
In Column 24, Line 60, delete "sealed is a" and insert -- sealed in a --, therefor.
In Column 25, Line 22, delete "sealed is a" and insert -- sealed in a --, therefor.
In Column 25, Line 45, delete "sealed is a" and insert -- sealed in a --, therefor.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*